United States Patent [19]

Koike et al.

[11] Patent Number: 5,436,242
[45] Date of Patent: Jul. 25, 1995

[54] TETRAHYDROTHIENOPYRIDINE DERIVATIVES, FURO AND PYRROLO ANALOGS THEREOF FOR INHIBITING BLOOD PLATELET AGGREGATION

[75] Inventors: Hiroyuki Koike; Fumitoshi Asai; Atsuhiro Sugidachi, all of Tokyo; Tomio Kimura, Ube; Teruhiko Inoue, Ube; Shigeyoshi Nishino, Ube; Yasunori Tsuzaki, Ube, all of Japan

[73] Assignees: Sankyo Company, Limited, Tokyo; Ube Industries Limited, Ube, both of Japan

[21] Appl. No.: 161,046

[22] Filed: Dec. 1, 1993

Related U.S. Application Data

[62] Division of Ser. No. 941,676, Sep. 8, 1992, Pat. No. 5,288,726.

Foreign Application Priority Data

Sep. 9, 1991 [JP] Japan .................. 3-227875
May 29, 1992 [JP] Japan .................. 4-138529

[51] Int. Cl.$^6$ .................. A61K 31/535; C07D 273/01
[52] U.S. Cl. .................. 514/229.2; 544/65
[58] Field of Search .............. 544/65; 514/229.2, 302; 546/115, 116

[56] References Cited

U.S. PATENT DOCUMENTS

| | | | |
|---|---|---|---|
| 4,051,141 | 9/1977 | Castaigne | 260/294.8 |
| 4,075,215 | 2/1978 | Castaigne | 260/294.8 |
| 4,127,580 | 11/1978 | Braye | 546/114 |
| 4,136,186 | 1/1979 | Frehel et al. | 546/114 |
| 4,458,074 | 7/1984 | Bouscuet et al. | 546/114 |
| 4,464,377 | 8/1984 | Blanchard et al. | 424/256 |
| 4,529,596 | 7/1985 | Aubert et al. | 514/231 |
| 4,740,510 | 4/1988 | Badorc et al. | 514/291 |

FOREIGN PATENT DOCUMENTS 0421861  4/1991  European Pat. Off. .

*Primary Examiner*—Raymond Henley, III
*Assistant Examiner*—Phyllis G. Spivack
*Attorney, Agent, or Firm*—Frishauf, Holtz, Goodman & Woodward

[57] ABSTRACT

Compounds of formula (I):

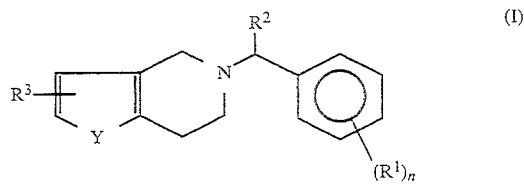

wherein $R^1$ is hydrogen, alkyl, halogen, haloalkyl, hydroxy, alkoxy, haloalkoxy, alkylthio, haloalkylthio, amino, alkanoyl, haloalkanoyl, carboxy, alkoxycarbonyl, carbamoyl, cyano, nitro, alkanesulfonyl, haloalkanesulfonyl or sulfamoyl; $R^2$ is 5,6-dihydro-1,4,2-dioxazin-3-yl; $R^3$ is hydrogen, hydroxy, optionally substituted alkoxy, aralkyloxy, alkanoyloxy, alkenoyloxy, cycloalkylcarbonyloxy, arylcarbonyloxy, alkoxycarbonyloxy, aralkyloxycarbonylxy, phthalidyloxy, (5-methyl-2-oxo-1,3-dioxolen-4-yl)methoxy, (5-phenyl-2-oxo-1,3-dioxolen-4-yl)methoxy, optionally substituted amino or nitro; Y is —NH— or oxygen or sulfur; n is 1 to 5; and tautomers and salts of said compounds of formula (I), have the ability to inhibit blood platelet aggregation, and can thus be used for treatment and prophylaxis of thrombosis and embolisms.

40 Claims, No Drawings

TETRAHYDROTHIENOPYRIDINE DERIVATIVES, FURO AND PYRROLO ANALOGS THEREOF FOR INHIBITING BLOOD PLATELET AGGREGATION

This is a division of application Ser. No. 07/941,676, filed Sep. 8, 1992, now U.S. Pat. No. 5,288,726.

BACKGROUND OF THE INVENTION

The present invention relates to a series of new tetrahydrothieno[3,2-c]pyridine derivatives and furo and pyrrolo analogs of these derivatives, and provides processes for preparing these derivatives as well as methods and compositions using them for inhibiting blood platelet aggregation.

A number of tetrahydrothienopyridine and tetrahydrofuropyridine derivatives is known, and some of these have been disclosed to have the ability to inhibit blood platelet aggregation. For example, U.S. Pat. Nos. 4,051,141, 4,075,215, 4,127,580, 4,464,377 and 4,529,596 all disclose compounds of this type, although not all disclose them for the inhibition of blood platelet aggregation. The closest prior art is believed to be U.S. Pat. No. 4,051,141, which discloses, inter alia, 5-(2-chlorobenzyl)-4,5,6,7-tetrahydrothieno[3,2-c]pyridine and U.S. Pat. No. 4,529,596, which discloses, inter alia, 5-(2-chloro-α-methoxycarbonylbenzyl)-4,5,6,7-tetrahydrothieno[3,2-c]pyridine.

However, there are problems with the prior art compounds referred to above, especially in that many of them require a long time after administration before they manifest their activity. Accordingly, there is a need for new compounds of this type having improved activity and the ability to act faster.

We have now discovered a series of new tetrahydrothieno[3,2-c]pyridine derivatives and furo and pyrrolo analogs of these derivatives which have an improved ability to inhibit the aggregation of blood platelets.

BRIEF SUMMARY OF INVENTION

It is, therefore, an object of the present invention to provide a series of new compounds of this type.

It is a further, and more specific object of the present invention to provide such compounds having valuable inhibitory activity against platelet aggregation.

Other objects and advantages of the present invention will become apparent as the description proceeds.

The compounds of the present invention are those compounds of formula (I):

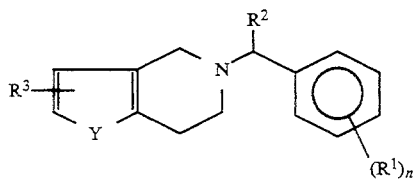

wherein:

$R^1$ represents a hydrogen atom, an alkyl group having from 1 to 4 carbon atoms, a halogen atom, a haloalkyl group having from 1 to 4 carbon atoms and at least one halogen atom, a hydroxy group, an alkoxy group having from 1 to 4 carbon atoms, a haloalkoxy group having from 1 to 4 carbon atoms and at least one halogen atom, an alkylthio group having from 1 to 4 carbon atoms, a haloalkylthio group having from 1 to 4 carbon atoms and at least one halogen atom, an amino group, an alkanoyl group having from 1 to 5 carbon atoms, a haloalkanoyl group having from 2 to 5 carbon atoms and at least one halogen atom, a carboxy group, an alkoxycarbonyl group hyacinth from 2 to 5 carbon atoms, a carbamoyl group, a cyano group, a nitro group, an alkanesulfonyl group having from 1 to 4 carbon atoms, a haloalkanesulfonyl group having from 1 to 4 carbon atoms and at least one halogen atom, or a sulfamoyl group;

$R^2$ represents an alkanoyl group having from 1 to 10 carbon atoms, a substituted alkanoyl group which has from 2 to 10 carbon atoms and which is substituted by at least one substituent selected from the group consisting of substituents A, defined below, an alkenoyl group having from 3 to 6 carbon atoms, a substituted alkenoyl group which has from 3 to 6 carbon atoms and which is substituted by at least one substituent selected from the group consisting of substituents A, defined below, a cycloalkylcarbonyl group having from 4 to 8 carbon atoms, a substituted cycloalkylcarbonyl group which has from 4 to 8 carbon atoms and which is substituted by at least one substituent selected from the group consisting of substituents A, defined below, a substituted benzoyl group having at least one substituent selected from the group consisting of substituents B, defined below, or a 5,6-dihydro-1,4,2-dioxazin-3-yl group;

$R^3$ represents a hydrogen atom, a hydroxy group, an alkoxy group having from 1 to 4 carbon atoms, a substituted alkoxy group which has from 1 to 4 carbon atoms and which is substituted by at least one substituent selected from the group consisting of substituents C, defined below, an aralkyloxy group in which the aralkyl part is as defined below, an alkanoyloxy group having from 1 to 18 carbon atoms, an alkenoyloxy group having from 3 to 6 carbon atoms, a cycloalkylcarbonyloxy group having from 4 to 8 carbon atoms, an arylcarbonyloxy group in which the aryl part is as defined below, an alkoxycarbonyloxy group having from 2 to 5 carbon atoms, an aralkyloxycarbonyloxy group in which the aralkyl part is as defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula $-NR^aR^b$ wherein $R^a$ and $R^b$ are independently selected from the group consisting of hydrogen atoms, alkyl groups having from 1 to 4 carbon atoms and substituted alkyl groups which have from 1 to 4 carbon atoms and which are substituted by at least one substituent selected from the group consisting of substituents C, defined below, an aralkylamino group in which the aralkyl part is as defined below, an alkanoylamino group having from 1 to 18 carbon atoms, an alkenoylamino group having from 3 to 6 carbon atoms, a cycloalkylcarbonylamino group having from 4 to 8 carbon atoms, an arylcarbonylamino group in which the aryl part is as defined below, an alkoxycarbonylamino group having from 2 to 5 carbon atoms, an aralkyloxycarbonylamino group in which the aralkyl part is as defined below, a phthalidylamino group, a (5-methyl-2-oxo-1,3-dioxolen-4-yl)methylamino group, a (5-phenyl-2- oxo-1,3-dioxolen-4-yl)methylamino group or a nitro group;

Y represents a group of formula —NH— or an oxygen or sulfur atom; and n is an integer from 1 to 5, and, when n is an integer from 2 to 5, the groups represented by $R^1$ may be the same as or different from each other;

said substituents A are selected from the group consisting of halogen atoms, hydroxy groups, alkoxy groups having from 1 to 4 carbon atoms and cyano groups;

said substituents B are selected from the group consisting of alkyl groups having from 1 to 4 carbon atoms, halogen atoms and alkoxy groups having from 1 to 4 carbon atoms;

said substituents C are selected from the group consisting of alkoxy groups having from 1 to 4 carbon atoms, alkanoyloxy groups having from 1 to 6 carbon atoms and arylcarbonyloxy groups in which the aryl part is as defined below;

said aralkyl parts of said aralkyloxy, aralkyloxycarbonyloxy, aralkylamino and aralkyloxycarbonylamino groups are alkyl groups which have from 1 to 4 carbon atoms and which are substituted by at least one aryl group as defined below;

said aryl groups and said aryl parts of said arylcarbonyloxy groups and of said arylcarbonylamino groups have from 6 to 10 carbon atoms in a carbocyclic ring which is unsubstituted or is substituted by at least one substituent selected from the group consisting of substituents D, defined below; and said substituents D are selected from the group consisting of the groups and atoms defined above in relation to $R^1$ other than said hydrogen atom;

and tautomers thereof and pharmaceutically acceptable salts of said compounds of formula (I) and of said tautomers.

The invention also provides a pharmaceutical composition for the treatment and prophylaxis of thrombosis or embolisms, comprising an effective amount of a blood platelet aggregation inhibitor in admixture with a pharmaceutically acceptable carrier or diluent, wherein said inhibitor is at least one compound of formula (I), or a tautomer or pharmaceutically acceptable salt thereof.

The invention still further provides a method for the treatment or prophylaxis of thrombosis or embolisms, comprising administering to a mammal, which may be human, an effective amount of a blood platelet aggregation inhibitor, wherein said inhibitor is at least one compound of formula (I), or a tautomer or pharmaceutically acceptable salt thereof.

The invention also provides processes for preparing these compounds, which are described in greater detail hereafter.

DETAILED DESCRIPTION OF INVENTION

When the compounds of the present invention have an amino or hydroxy group at the 2- or 3-position (i.e. $R^3$ represents an amino or hydroxy group at the 2- or 3-position), they can exist as keto-enol tautomers, that is:

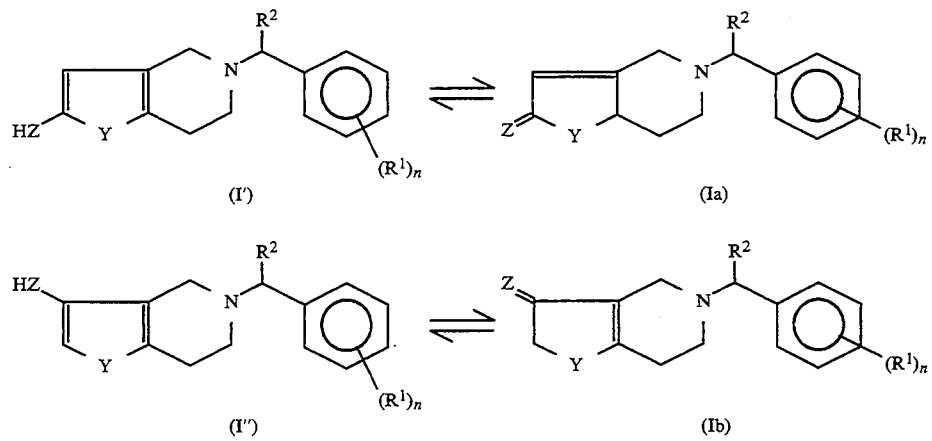

wherein Y, $R^1$, $R^2$ and n are as defined above and Z represents a group of formula =NH or an oxygen atom. These tautomers may or may not be readily separable, and, if separable, may be separated by methods well known in the art. In any event, the present invention embraces both the individual isolated tautomers, as well as mixtures thereof, and both the isolated tautomers and such mixtures may be used in the compositions and methods of the present invention. In particular, the tautomers of formula (Ia) are preferred.

In the compounds of the present invention, where $R^1$ represents an alkyl group, this may be a straight or branched chain alkyl group having from 1 to 4 carbon atoms, and examples include the methyl, ethyl, propyl, isopropyl, butyl, isobutyl, sec-butyl and t-butyl groups. Of these, we prefer those alkyl groups having from 1 to 3 carbon atoms, more preferably the methyl and ethyl groups.

Where $R^1$ represents a halogen atom, this may be, for example, a fluorine, chlorine, iodine or bromine atom, and is preferably a fluorine or chlorine atom.

Where $R^1$ represents a haloalkyl group, the alkyl part may be any one of the alkyl groups exemplified above and may be substituted by one or more halogen (for example fluorine, chlorine, bromine or iodine) atoms. There is, in principle, no restriction on the number of halogen substituents on the alkyl group, this being limited only by the number of substitutable atoms. In general, however, from 1 to 5 halogen substituents are preferred, from 1 to 3 substituents being more preferred. Specific examples of such groups include the fluoromethyl, difluoromethyl, trifluoromethyl, chloromethyl, dichloromethyl, trichloromethyl, 2-fluoroethyl, 2-chloroethyl, 2-bromoethyl, 2-iodoethyl, 2,2,2-trichloroethyl, 2,2,2-trifluoroethyl, 2-fluoropropyl, 3-fluoropropyl, 3-chloropropyl, 2-fluorobutyl, 3-fluorobutyl, 4-chlorobutyl and 4-fluorobutyl groups. The fluorine-substituted and chlorine-substituted groups are preferred, the fluorine-substituted groups being more preferred. The fluoromethyl, difluoromethyl and trifluoromethyl groups are most preferred, especially the trifluoromethyl group.

Where $R^1$ represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups. Of these, we prefer those alkoxy groups having from 1 to 3 carbon atoms, more preferably the methoxy and ethoxy groups.

Where $R^1$ represents a haloalkoxy group, the alkoxy part may be any one of the alkoxy groups exemplified above and may be substituted by one or more halogen (for example fluorine, chlorine, bromine or iodine) atoms. There is, in principle, no restriction on the number of halogen substituents on the alkoxy group, this being limited only by the number of substitutable atoms. In general, however, from 1 to 5 halogen substituents are preferred, from 1 to 3 substituents being more preferred. Specific examples of such groups include the fluoromethoxy, difluoromethoxy, trifluoromethoxy, 2-fluoroethoxy, 2-chloroethoxy, 2-bromoethoxy, 2-iodoethoxy, 2,2,2-trichloroethoxy, 2,2,2-trifluoroethoxy, 2-fluoropropoxy, 3-fluoropropoxy, 3-chloropropoxy, 2-fluorobutoxy, 3-fluorobutoxy, 4-chlorobutoxy and 4-fluorobutoxy groups. The fluoroalkoxy groups are preferred. The fluoromethoxy, difluoromethoxy and trifluoromethoxy groups are most preferred, especially the trifluoromethoxy group.

Where $R^1$ represents an alkylthio group, this may be a straight or branched chain alkylthio group having from 1 to 4 carbon atoms, and examples include the methylthio, ethylthio, propylthio, isopropylthio, butylthio, isobutylthio, sec-butylthio and t-butylthio groups. Of these, we prefer those alkylthio groups having from 1 to 3 carbon atoms, more preferably the methylthio and ethylthio groups.

Where $R^1$ represents a haloalkylthio group, the alkylthio part may be any one of the alkylthio groups exemplified above and may be substituted by one or more halogen (for example fluorine, chlorine, bromine or iodine) atoms. There is, in principle, no restriction on the number of halogen substituents on the alkylthio group, this being limited only by the number of substitutable atoms. In general, however, from 1 to 5 halogen substituents are preferred, from 1 to 3 substituents being more preferred. Specific examples of such groups include the fluoromethylthio, difluoromethylthio, trifluoromethylthio, 2-fluoroethylthio, 2-chloroethylthio, 2-bromoethylthio, 2-iodoethylthio, 2,2,2-trichloroethylthio, 2,2,2-trifluoroethylthio, 2-fluoropropylthio, 3-fluoropropylthio, 3-chloropropylthio, 2-fluorobutylthio, 3-fluorobutylthio, 4-chlorobutylthio and 4-fluorobutylthio groups. The fluorine-substituted groups are preferred. The fluoromethylthio, difluoromethylthio and trifluoromethylthio groups are most preferred, especially the trifluoromethylthio group.

Where $R^1$ represents an alkanoyl group, this has from 1 to 5 carbon atoms and may be a straight or branched chain group. Examples include the formyl, acetyl, propionyl, butyryl, isobutyryl, valeryl, isovaleryl and pivaloyl groups, of which the formyl and acetyl groups are preferred.

Where $R^1$ represents a haloalkanoyl group, this has from 2 to 5 carbon atoms and may be a straight or branched chain group. Examples include the fluoroacetyl, difluoroacetyl, trifluoroacetyl, chloroacetyl, trichloroacetyl, bromoacetyl, iodoacetyl, 3-fluoropropionyl, 4-fluorobutyryl and 5-fluorovaleryl groups. Of these, the fluorine-substituted alkanoyl groups are preferred, the fluoroacetyl, difluoroacetyl and trifluoroacetyl groups being more preferred and the trifluoroacetyl group being most preferred.

Where $R^1$ represents an alkoxycarbonyl group, this may be a straight or branched chain alkoxycarbonyl group having from 2 to 5 carbon atoms, that is the alkoxy part has from 1 to 4 carbon atoms, and examples include the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups. Of these, we prefer those alkoxycarbonyl groups having from 1 to 3 carbon atoms, more preferably the methoxycarbonyl and ethoxycarbonyl groups.

Where $R^1$ represents an alkanesulfonyl group, this may be a straight or branched chain alkanesulfonyl group having from 1 to 4 carbon atoms, and examples include the methanesulfonyl, ethanesulfonyl, propanesulfonyl, isopropanesulfonyl, butanesulfonyl, isobutanesulfonyl, sec-butanesulfonyl and t-butanesulfonyl groups. Of these, we prefer those alkanesulfonyl groups having from 1 to 3 carbon atoms, more preferably the methanesulfonyl and ethanesulfonyl groups.

Where $R^1$ represents a haloalkanesulfonyl group, the alkanesulfonyl part may be any one of the alkanesulfonyl groups exemplified above and may be substituted by one or more halogen (for example fluorine, chlorine, bromine or iodine) atoms. There is, in principle, no restriction on the number of halogen substituents on the alkanesulfonyl group, this being limited only by the number of substitutable atoms. In general, however, from 1 to 5 halogen substituents are preferred, from 1 to 3 substituents being more preferred. Specific examples of such groups include the fluoromethanesulfonyl, difluoromethanesulfonyl, trifluoromethanesulfonyl, dichloromethanesulfonyl, trichloromethanesulfonyl, 2-fluoroethanesulfonyl, 2-chloroethanesulfonyl, 2-bromoethanesulfonyl, 2-iodoethanesulfonyl, 2,2,2-trichloroethanesulfonyl, 2,2,2-trifluoroethanesulfonyl, 2-fluoropropanesulfonyl, 3-fluoropropanesulfonyl, 3-chloropropanesulfonyl, 2-fluorobutanesulfonyl, 3-fluorobutanesulfonyl, 4-chlorobutanesulfonyl and 4-fluorobutanesulfonyl groups. The fluorine-substituted alkanesulfonyl and chlorine-substituted alkanesulfonyl groups are preferred, the fluorine-substituted alkanesulfonyl groups being more preferred. The fluoromethanesulfonyl, difluoromethanesulfonyl and trifluoromethanesulfonyl groups are most preferred, especially the trifluoromethanesulfonyl group.

Of the above groups and atoms, we especially prefer that $R^1$ should represent: a hydrogen atom; an alkyl group having from 1 to 4 carbon atoms; a halogen atom; a fluorine-substituted alkyl group having from 1 to 4 carbon atoms; a hydroxy group; an alkoxy group having from 1 to 4 carbon atoms; a fluorine-substituted alkoxy group having from 1 to 4 carbon atoms; an alkylthio group having from 1 to 4 carbon atoms; a fluorine-substituted alkylthio group having from 1 to 4 carbon atoms; an amino group; an alkanoyl group having from 1 to 5 carbon atoms; a fluorine-substituted alkanoyl group having from 2 to 5 carbon atoms; an alkoxycarbonyl group having from 2 to 5 carbon atoms; a carbonyl group; a cyano group; a nitro group; an alkanesulfonyl group having from 1 to 4 carbon atoms; a fluorine-substituted alkanesulfonyl group having from 1 to 4 carbon atoms; or a sulfamoyl group.

More preferably $R^1$ represents: a hydrogen atom; a methyl group; an ethyl group; a halogen atom; a fluorine-substituted methyl group; a hydroxy group; a methoxy group; an ethoxy group; a fluorine-substituted methoxy group; a methylthio group; a fluorine-substituted methylthio group; a formyl group; an acetyl group; a fluorine-substituted acetyl group; a methoxycarbonyl group; an ethoxycarbonyl group; a propoxycarbonyl group; a carbamoyl group; a cyano group; a nitro group; a methanesulfonyl group; an ethanesulfonyl group; a fluorine-substituted methanesulfonyl group; or a sulfamoyl group.

Still more preferably $R^1$ represents: a halogen atom; a trifluoromethyl group; a hydroxy group; a difluoromethoxy group; a trifluoromethoxy group; a difluoromethylthio group; a trifluoromethylthio group; a formyl group; an acetyl group; a trifluoroacetyl group; a cyano group or a nitro group.

Most preferably $R^1$ represents: a fluorine atom, a chlorine atom or a trifluoromethyl group; especially a fluorine atom or a chlorine atom.

The number of the substituents, n, represented by $R^1$ is from 1 to 5, although the maximum may be lower than 5 in some cases if there is a problem of steric hindrance. Preferably n is from 1 to 3, and more preferably 1 or 2. The position of substitution by $R^1$ on the phenyl group is preferably para or ortho, more preferably ortho.

Where $R^2$ represents an alkanoyl group having from 1 to 10 carbon atoms, this may be a straight or branched chain group, and examples include the formyl, acetyl, propionyl, butyryl, isobutyryl, valeryl, isovaleryl, pivaloyl, hexanoyl, heptanoyl, octanoyl, nonanoyl and decanoyl groups, of which those groups having from 2 to 6 carbon atoms are preferred, especially the acetyl, propionyl and isobutyryl groups, of which the acetyl and propionyl groups are most preferred.

Those alkanoyl groups represented by $R^2$ and having from 2 to 10 carbon atoms may be substituted by one or more of substituents A, defined above. Examples of such substituents A include:
halogen atoms, such as the fluorine, chlorine, bromine and iodine atoms;
hydroxy groups;
alkoxy groups having from 1 to 4 carbon atoms, such as those exemplified above in relation to $R^1$; and
cyano groups.

In the case of these substituted groups, and all substituted groups referred to herein, there is no specific limitation on the number of the substituents, except such as may be imposed by the number of substitutable positions and possibly also by steric constraints. However, in general, from 1 to 3 such substituents are preferred.

Specific examples of such substituted alkanoyl groups include the fluoroacetyl, difluoroacetyl, trifluoroacetyl, chloroacetyl, trichloroacetyl, bromoacetyl, iodoacetyl, 3-fluoropropionyl, 3-chloropropionyl, 3-bromopropionyl, 3-iodopropionyl, 4-fluorobutyryl, 4-chlorobutyryl, 5-fluorovaleryl, hydroxyacetyl, 3-hydroxypropionyl, 4-hydroxybutyryl, 5-hydroxyvaleryl, methoxyacetyl, 3-methoxypropionyl, 4-methoxybutyryl, 5-methoxyvaleryl, ethoxyacetyl, 3-ethoxypropionyl, 4-enhoxybutyryl, 5-ethoxyvaleryl, cyanoacetyl, 3-cyanopropionyl, 4-cyanobutyryl and 5-cyanovaleryl groups, of which the fluoroacetyl, difluoroacetyl, trifluoroacetyl, chloroacetyl, 3-fluoropropionyl, 3-chloropropionyl, hydroxyacetyl, 3-hydroxypropionyl, methoxyacetyl, 3-methoxypropionyl, ethoxyacetyl, cyanoacetyl and 3-cyanopropionyl groups are more preferred. Still more preferred are the fluoroacetyl, difluoroacetyl, trifluoroacetyl, chloroacetyl, 3-fluoropropionyl, hydroxyacetyl, methoxyacetyl, ethoxyacetyl and cyanoacetyl groups. The most preferred groups are the fluoroacetyl, difluoroacetyl, trifluoroacetyl, chloroacetyl, 3-fluoropropionyl, hydroxyacetyl, methoxyacetyl and cyanoacetyl groups, especially the fluoroacetyl, difluoroacetyl and trifluoroacetyl groups.

Where $R^2$ represents an alkenoyl group having from 3 to 6 carbon atoms, this may be a straight or branched chain group, and examples include the acryloyl, methacryloyl, 2-butenoyl, 2-pentenoyl and 2-hexenoyl groups, of which the acryloyl and methacryloyl groups are preferred.

These alkenoyl groups may also be substituted by one or more of substituents A, defined and exemplified above. Specific examples of such substituted groups include the 3-fluoroacryloyl, 3-chloroacryloyl and 3-cyanoacryloyl groups, of which the 3-fluoroacryloyl group is particularly preferred.

Where $R^2$ represents a cycloalkylcarbonyl group, this has from 4 to 8 carbon atoms, that is the cycloalkyl group itself has from 3 to 7 ring carbon atoms. Examples of such groups include the cyclopropylcarbonyl, cyclobutylcarbonyl, cyclopentylcarbonyl, cyclohexylcarbonyl and cycloheptylcarbonyl groups, of which the cyclopropylcarbonyl and cyclobutylcarbonyl groups are particularly preferred.

These cycloalkylcarbonyl groups may also be substituted by one or more of substituents A, defined and exemplified above. Specific examples of such substituted groups include the 2-fluorocyclopropylcarbonyl, 2,2-difluorocyclopropylcarbonyl, 2-chlorocyclopropylcarbonyl, 2-bromocyclopropylcarbonyl, 2-fluorocyclobutylcarbonyl, 2-chlorocyclobutylcarbonyl, 2-fluorocyclopentylcarbonyl, 2-chlorocyclopentylcarbonyl, 2-fluorocyclohexylcarbonyl, 2-chlorocyclohexylcarbonyl, 2-hydroxycyclopropylcarbonyl, 2-hydroxycyclobutylcarbonyl, 2-hydroxycyclopentylcarbonyl, 2-hydroxycyclohexylcarbonyl, 2-methoxycyclopropylcarbonyl, 2-methoxycyclobutylcarbonyl, 2-methoxycyclopentylcarbonyl, 2-methoxycyclohexylcarbonyl, 2-ethoxycyclopropylcarbonyl, 2-ethoxycyclobutylcarbonyl, 2-ethoxycyclopentylcarbonyl, 2-ethoxycyclohexylcarbonyl, 2-cyanocyclopropylcarbonyl, 2-cyanocyclobutylcarbonyl, 2-cyanocyclopentylcarbonyl and 2-cyanocyclohexylcarbonyl groups, of which the 2-fluorocyclopropylcarbonyl, 2,2-difluorocyclopropylcarbonyl, 2-chlorocyclopropylcarbonyl, 2-fluorocyclobutylcarbonyl, 2-chlorocyclobutylcarbonyl, 2-fluorocyclopentylcarbonyl, 2-fluorocyclohexylcarbonyl, 2-hydroxycyclopropylcarbonyl, 2-methoxycyclopropylcarbonyl, 2-ethoxycyclopropylcarbonyl and 2-cyanocyclopropylcarbonyl groups are preferred. More preferred groups are the 2-fluorocyclopropylcarbonyl, 2-chlorocyclopropylcarbonyl, 2-fluorocyclobutylcarbonyl and 2-methoxycyclopropylcarbonyl groups, and the most preferred is the 2-fluorocyclopropylcarbonyl group.

Where $R^2$ represents a substituted benzoyl group, this is substituted by at least one of substituents B, which are selected from the group consisting of alkyl groups having from 1 to 4 carbon atoms, halogen atoms and alkoxy groups having from 1 to 4 carbon atoms, all of which may be as exemplified in relation to the same groups and atoms represented by $R^1$. The number of the substituents may be from 1 to 5, provided that there is no problem of steric hindrance; preferably, however, there are from 1 to 3 substituents, more preferably 1 or 2. Specific examples of such substituted benzoyl groups include the 2-fluorobenzoyl, 3-fluorobenzoyl, 4-fluorobenzoyl, 2,4-difluorobenzoyl, 2,4,6-trifluorobenzoyl, 2,3,4,5,6-pentafluorobenzoyl, 4-chlorobenzoyl, 2,4-dichlorobenzoyl, 4-methylbenzoyl, 2,4-dimethylbenzoyl, 4-ethylbenzoyl, 2,4-diethylbenzoyl, 4-methoxybenzoyl, 2,4-dimethoxybenzoyl, 4-ethoxybenzoyl and 2,4-diethoxybenzoyl groups, of which the 4-fluorobenzoyl and 2,4-difluorobenzoyl groups are preferred.

Where $R^3$ represents an alkoxy group, this may be a straight or branched chain group having from 1 to 4 carbon atoms and may be any of the alkoxy groups exemplified above in relation to $R^1$. Such a group may be unsubstituted or it may have one or more substituents selected from the group consisting of substituents C, defined above, and examples of which are as follows:

alkoxy groups having from 1 to 4 carbon atoms, such as those exemplified above in relation to $R^1$;

alkanoyloxy groups having from 1 to 6 carbon atoms, which may be a straight or branched chain group, for example the formyloxy, acetoxy, propionyloxy, butyryloxy, isobutyryloxy, valeryloxy, isovaleryloxy, pivaloyloxy or hexanoyloxy groups, of which those groups having from 1 to 5 carbon atoms are preferred, and the acetoxy, propionyloxy, butyryloxy and pivaloyloxy groups are most preferred; and arylcarbonyloxy groups in which the aryl part is as defined above, for example the arylcarbonyloxy groups exemplified below in relation to $R^3$.

Specific examples of such substituted alkoxy groups include the methoxymethoxy, ethoxymethoxy, propoxymethoxy, butoxymethoxy, 2-methoxyethoxy, 2-ethoxyethoxy, formyloxymethoxy, acetoxymethoxy, propionyloxymethoxy, 2-formyloxyethoxy, 2-acetoxyethoxy, 2-propionyloxyethoxy, 3-acetoxypropoxy, 4-acetoxybutoxy, valeryloxymethoxy, pivaloyloxymethoxy, benzoyloxymethoxy, naphthoyloxymethoxy, p-toluoyloxymethoxy, p-chlorobenzoyloxymethoxy, 2-benzoyloxyethoxy, 3-benzoyloxypropoxy and 4-benzoyloxybutoxy groups, of which the pivaloyloxymethoxy group is most preferred.

Where $R^3$ represents an aralkyloxy group, the alkoxy part is an alkoxy group having from 1 to 4, preferably from 1 to 3, carbon atoms, such as those exemplified above in relation to $R^1$ especially the methoxy, ethoxy, propoxy or isopropoxy groups. The aryl part is as defined above and has from 6 to 10, preferably 6 or 10, ring carbon atoms. Examples of such aryl groups include the phenyl, 1-naphthyl and 2-naphthyl groups and such groups which are substituted by one or more of substituents D, defined above and examples of which have been given in relation to the same groups and atoms which may be represented by $R^1$. The alkoxy part may be substituted by one or more aryl groups, the maximum being dictated only by the number of substitutable positions and possibly also by steric constraints; however, from 1 to 3 aryl groups are normally preferred, 1 or 2 being more preferred and 1 being most preferred. Specific examples of the aralkyloxy groups include the benzyloxy, 1-naphthylmethoxy, 2-naphthylmethoxy, phenethyloxy, α-methylbenzyloxy, 3-phenylpropoxy, 2-phenylpropoxy, 1-phenylpropoxy, 4-phenylbutoxy, benzhydryloxy (i.e. diphenylmethoxy) and trityloxy (i.e. triphenylmethoxy) groups (of these, the benzyloxy and phenethyloxy groups are preferred), and such groups which are substituted by one or more of substituents D.

Where $R^3$ represents an alkanoyloxy group, this may be a straight or branched chain group and has from 1 to 18 carbon atoms. Examples of such groups include the formyloxy, acetoxy, propionyloxy, butyryloxy, isobutyryloxy, valeryloxy, isovaleryloxy, pivaloyloxy, hexanoyloxy, heptanoyloxy, octanoyloxy, nonanoyloxy, decanoyloxy, lauroyloxy, myristoyloxy, palmitoytoxy and stearoyloxy groups, of which those groups having from 1 to 12 carbon atoms are preferred, those having from 2 to 10 carbon atoms are more preferred, and those having from 2 to 5 carbon atoms are most preferred, especially the acetoxy, propionyloxy, butyryloxy, pivaloyloxy, nonanoyloxy and decanoyloxy groups, of which the acetoxy, propionyloxy, butyryloxy and pivaloyloxy groups are most preferred.

Where $R^3$ represents an alkenoyloxy group, this may be a straight or branched chain group and has from 3 to 6, more preferably 3 or 4, carbon atoms. Examples of such groups include the acryloyloxy, methacryloyloxy, 2-butenoyloxy, 2-pentenoyloxy and 2-hexenoyloxy groups, of which the acryloyloxy and methacryloyloxy groups are preferred.

Where $R^3$ represents a cycloalkylcarbonyloxy group, this has from 4 to 8, more preferably from 4 to 7, carbon atoms, that is the cycloalkyl group itself has from 3 to 7 ring carbon atoms. Examples of such groups include the cyclopropylcarbonyloxy, cyclobutylcarbonyloxy, cyclopentylcarbonyloxy, cyclohexylcarbonyloxy and cycloheptylcarbonyloxy groups, of which the cyclopropylcarbonyloxy and cyclobutylcarbonyloxy groups are particularly preferred.

Where $R^3$ represents arylcarbonyloxy group, the aryl part is as defined above, and examples of such groups include the benzoyloxy, 1-naphthoyloxy, 2-naphthoyloxy, o-, m- and p-toluoyloxy, o-, m- and p-chlorobenzoyloxy, o-, m- and p-fluorobenzoyloxy, o-, m- and p-methoxybenzoyloxy, 2,3-, 2,4-, 2,5-, 2,6-, 3,4-and 3,5-dichlorobenzoyloxy, 2,4-difluorobenzoyloxy and 2,4,6-trifluorobenzoyloxy groups, preferably the benzoyloxy group.

Where $R^3$ represents an alkoxycarbonyloxy group, this may be a straight or branched chain alkoxycarbonyloxy group having from 2 to 5 carbon atoms, that is the alkoxy part has from 1 to 4 carbon atoms, and examples include the methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy and t-butoxycarbonyloxy groups. Of these, we prefer those alkoxycarbonyloxy groups having from 1 to 3 carbon atoms in the alkoxy part and the t-butoxycarbonyloxy group, more preferably the methoxycarbonyloxy, ethoxycarbonyloxy and t-butoxycarbonyloxy groups.

Where $R^3$ represents an aralkyloxycarbonyloxy group, the alkoxy part is an alkoxy group having from 1 to 4, preferably from 1 to 3, carbon atoms, such as those exemplified above in relation to $R^1$, especially the methoxy, ethoxy, propoxy or isopropoxy groups. The aryl part is as defined above and has from 6 to 10, preferably 6 or 10, ring carbon atoms. Examples of such aryl groups include the phenyl, 1-naphthyl and 2-naphthyl groups and such groups which are substituted by one or more of substituents D, defined above and examples of which have been given in relation to the same groups and atoms which may be represented by $R^1$. The alkoxy part may be substituted by one or more aryl groups, the maximum being dictated only by the number of substitutable positions and possibly also by steric constraints; however, from 1 to 3 aryl groups are normally preferred, 1 or 2 being more preferred and 1 being most preferred. Specific examples of the aralkyloxycarbonyloxy groups include the benzyloxycarbonyloxy, 1-napthylmethoxycarbonyloxy, 2-naphthylmethoxycarbonyloxy, phenethyloxycarbonyloxy, α-methylbenzyloxycarbonyloxy, 3-phenylpropoxycarbonyloxy, 2-phenylpropoxycarbonyloxy, 1-phenylpropoxycarbonyloxy, 4-phenylbutoxycarbonyloxy, benzhydryloxycarbonyloxy and trityloxycarbonyloxy groups (of these, the benzyloxycarbonyloxy group is preferred), and such groups which are substituted by one or more of substituents D.

Where $R^3$ represents a group of formula $-NR^aR^b$, $R^a$ and $R^b$ are independently selected from the group consisting of hydrogen atoms, alkyl groups having from 1 to 4 carbon atoms and substituted alkyl groups which have from 1 to 4 carbon atoms and which are substituted by at least one substituent selected from the group consisting of substituents C, defined above. Examples of the alkyl groups which may be represented by $R^a$ and $R^b$ are as given above in relation to $R^1$, and examples of the substituted alkyl groups which may be represented by $R^a$ and $R^b$ are the substituted alkyl groups corresponding to the substituted alkoxy groups, as given above in relation to $R^3$. Specific examples of these groups of formula $-NR^aR^b$ include the amino, methylamino, ethylamino, propylamino, isopropylamino, butylamino, isobutyamino, sec-butylamino, t-butylamino, dimethylamino, diethylamino, dipropylamino, diisopropylamino, dibutylamino, methylethylamino, methylpropylamino, N-(methoxymethyl)amino, N-(2-methoxyethyl)amino, N-(acetoxymethyl)amino, N-(pivaloyloxymethyl)amino, N-(benzoylmethyl)amino, N-(2-acetoxyethyl)amino, N-(2-pivaloyloxyethyl)amino and N-(2-benzoylethyl)amino groups, preferably the amino, methylamino, ethylamino, N-(acetoxymethyl)amino and N-(pivaloyloxymethyl)amino groups.

Where $R^3$ represents an aralkylamino group, the alkyl part is an alkyl group having from 1 to 4, preferably from 1 to 3, carbon atoms, such as those exemplified above in relation to $R^1$, especially the methyl, ethyl, propyl or isopropyl groups. The aryl part is as defined above and has from 6 to 10, preferably 6 or 10, ring carbon atoms. Examples of such aryl groups include the phenyl, 1-naphthyl and 2-naphthyl groups and such groups which are substituted by one or more of substituents D, defined above and examples of which have been given in relation to the same groups and atoms which may be represented by $R^1$. The alkyl part may be substituted by one or more aryl groups, the maximum being dictated only by the number of substitutable positions and possibly also by steric constraints; however, from 1 to 3 aryl groups are normally preferred, 1 or 2 being more preferred and 1 being most preferred. Specific examples of the aralkylamino groups include the benzylamino, N-(1-naphthylmethyl)amino, N-(2-naphthylmethyl)amino, phenethylamino, N-(α-methylbenzyl)amino, N-(3-phenylpropyl)amino, N-(2-phenylpropyl)amino, N-(1-phenylpropyl)amino, N-(4-phenylbutyl)amino, benzhydrylamino and tritylamino groups (of these, the benzylamino group is preferred), and such groups which are substituted by one or more of substituents D.

Where $R^3$ represents an alkanoylamino group, this may be a straight or branched chain group and has from 1 to 18 carbon atoms. Examples of such groups include the formamido, acetamido, propionamido, butyramido, isobutyramido, valerylamino, isovalerylamino, pivaloylamino, hexanoylamino, heptanoylamino, octanoylamino, nonanoylamino, decanoylamino, lauroylamino, myristoylamino, palmitoylamino and stearoylamino groups, of which those groups having from 1 to 12 carbon atoms are preferred, those having from 2 to 10 carbon atoms are more preferred, and those having from 2 to 5 carbon atoms are most preferred, especially the acetamido, propionamido, butyramido, pivaloylamino, nonanoylamino and decanoylamino groups, of which the acetamido, propionamido, butyramido and pivaloylamino groups are most preferred.

Where $R^3$ represents an alkenoylamino group, this may be a straight or branched chain group and has from 3 to 6 carbon atoms. Examples of such groups include the acryloylamino, methacryloylamino, 2-butenoylamino, 2-pentenoylamino and 2-hexenoylamino groups, of which the acryloylamino and methacryloylamino groups are preferred.

Where $R^3$ represents a cycloalkylcarbonylamino group, this has from 4 to 8 carbon atoms, that is the cycloalkyl group itself has from 3 to 7 ring carbon atoms. Examples of such groups include the cyclopropylcarbonylamino, cyclobutylcarbonylamino, cyclopentylcarbonylamino, cyclohexylcarbonylamino and cycloheptylcarbonylamino groups, of which the cyclopropylcarbonylamino and cyclobutylcarbonylamino groups are particularly preferred.

Where $R^3$ represents arylcarbonylamino group, the aryl part is as defined above, and examples of such groups include the benzamido, 1-naphthoylamino, 2-naphthoylamino, o-, m- and p-toluoylamino, o-, m- and p-chlorobenzamido, o-, m- and p-fluorobenzamido, o-, m-and p-methoxybenzamido, 2,4-dichlorobenzamido, 2,4-difluorobenzamido and 2,4,6-trifluorobenzamido groups, preferably the benzamido group.

Where $R^3$ represents an alkoxycarbonylamino group, this may be a straight or branched chain alkoxycarbonylamino group having from 2 to 5 carbon atoms, that is the alkoxy part has from 1 to 4 carbon atoms, and examples include the methoxycarbonylamino, ethoxycarbonylamino, propoxycarbonylamino, isopropoxycarbonylamino, butoxycarbonylamino, isobutoxycarbonylamino, sec-butoxycarbonylamino and t-butoxycarbonylamino groups. Of these, we prefer those alkoxycarbonylamino groups having from 1 to 3 carbon atoms in the alkoxy part and the t-butoxycarbonylamino group, more preferably the methoxycarbonylamino, ethoxycarbonylamino and t-butoxycarbonylamino groups.

Where $R^3$ represents an aralkoxycarbonylamino group, the alkoxy part is an alkoxy group having from 1 to 4, preferably from 1 to 3, carbon atoms, such as those exemplified above in relation to $R^1$, especially the methoxy, ethoxy, propoxy or isopropoxy groups. The aryl part is as defined above and has from 6 to 10, preferably 6 or 10, ring carbon atoms. Examples of such aryl groups include the phenyl, 1-naphthyl and 2-naphthyl groups and such groups which are substituted by one or more of substituents D, defined above and examples of which have been given in relation to the same groups and atoms which may be represented by $R^1$. The alkoxy part may be substituted by one or more aryl groups, the maximum being dictated only by the number of substitutable positions and possibly also by steric constraints; however, from 1 to 3 aryl groups are normally preferred, 1 or 2 being more preferred and 1 being most preferred. Specific examples of the aralkyloxycarbonylamino groups include the benzyloxycarbonylamino, N-(1-naphthylmethoxycarbonyl)amino, N-(2-naphthylmethoxycarbonyl)amino, phenethyloxycarbonylamino, N-(α-methylbenzyloxycarbonyl)amino, N-(3-phenylpropoxycarbonyl)amino, N-(2-phenylpropoxycarbonyl)amino, N-(1-phenylpropoxycarbonyl)amino, N-(4-phenylbutoxycarbonyl)amino, benzhydryloxycarbonylamino and trityloxycarbonylamino groups (of these, the benzyloxycarbonylamino group is preferred), and such groups which are substituted by one or more of substituents D.

Y represents a group of formula —NH— or an oxygen or sulfur atom, preferably an oxygen or sulfur atom, and more preferably a sulfur atom.

$R^3$ may be at either the 2- or the 3-position of the tetrahydropyrrolopyridyl, tetrahydrothienopyridyl or tetrahydrofuropyridyl group, but is preferably at the 2-position, especially when the Y is an oxygen or sulfur atom, i.e. on the tetrahydrothienopyridyl or tetrahydrofuropyridyl group.

In the compounds of the present invention, the carbon atom to which the group represented by $R^2$ is attached is an assymetric carbon atom, and other carbon atoms may be assymetric, and the compounds accordingly form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

In addition, when the compounds of the present invention have one or more carbon-carbon double bonds or one or more disubstituted cycloalkyl moieties, they form cis and trans isomers. The present invention includes both the individual, isolated isomers and mixtures thereof.

The compounds of the present invention can form acid addition salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; and salts with organic carboxylic acids, such as acetic acid, propionic acid, burytic acid, fumaric acid, tartaric acid, oxalic acid, malonic acid, maleic acid, malic acid, succinic acid, benzoic acid, mandelic acid, ascorbic acid, lactic acid, gluconic acid or citric acid.

The compounds of the present invention may also readily form hydrates and these, also, form part of the present invention.

Additionally, when $R^3$ represents an amino group or a substituted amino group, the resulting compound can form a complex salt with a metal ion, and such complex salts also form part of the present invention. Examples of such complex salts include salts with calcium chloride, magnesium chloride, zinc chloride, ferric chloride, stannic chloride and nickel chloride.

Preferred classes of compounds of the present invention are those compounds of formulae (I) and tautomers and salts thereof in which:

(A) $R^1$ represents a hydrogen atom, an alkyl group having from 1 to 4 carbon atoms, a halogen atom, a fluoroalkyl group having from 1 to 4 carbon atoms and at least one fluorine atom, a hydroxy group, an alkoxy group having from 1 to 4 carbon atoms, a fluoroalkoxy group having from 1 to 4 carbon atoms and at least one fluorine atom, an alkylthio group having from 1 to 4 carbon atoms, a fluoroalkylthio group having from 1 to 4 carbon atoms and at least one fluorine atom, an amino group, an alkanoyl group having from 1 to 5 carbon atoms, a fluoroalkanoyl group having from 2 to 5 carbon atoms and at least one fluorine atom, an alkoxycarbonyl group having from 2 to 5 carbon atoms, a carbamoyl group, a cyano group, a nitro group, an alkanesulfonyl group having from 1 to 4 carbon atoms, a fluoroalkanesulfonyl group having from 1 to 4 carbon atoms and at least one fluorine atom, or a sulfamoyl group.

(B) $R^2$ represents an alkanoyl group having from 2 to 6 carbon atoms, a substituted alkanoyl group which has from 2 to 6 carbon atoms and which is substituted by at least one substituent selected from the group consisting of substituents A', defined below, a cycloalkylcarbonyl group having from 4 to 7 carbon atoms, a substituted cycloalkylcarbonyl group which has from 4 to 7 carbon atoms and which is substituted by at least one substituent selected from the group consisting of substituents A', defined below, a substituted benzoyl group having at least one fluorine substituent, or a 5,6-dihydro-1,4,2-dioxazin-3-yl group; and said substituents A' are selected from the group consisting of fluorine atoms, chlorine atoms, hydroxy groups, methoxy groups, ethoxy groups and cyano groups.

(C) $R^3$ represents a hydrogen atom, a hydroxy group, an alkoxy group having from 1 to 4 carbon atoms, an alkoxymethoxy group in which the alkoxy part has from 1 to 4 carbon atoms, an alkanoyloxymethoxy group in which the alkanoyl part has from 1 to 5 carbon atoms, a benzyloxy group which is unsubstituted or is substituted by at least one substituent selected from the group consisting of substituents D', defined below, an alkanoyloxy group having from 1 to 18 carbon atoms, an alkenoyloxy group having 3 or 4 carbon atoms, a cycloalkylcarbonyloxy group having from 4 to 7 carbon atoms, a benzoyloxy group which is unsubstituted or is substituted by at least one substituent selected from the group consisting of substituents D', defined below, an alkoxycarbonyloxy group having from 2 to 5 carbon atoms, a benzyloxycarbonyloxy group which is unsubstituted or is substituted by at least one substituent selected from the group consisting of substituents D', defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula —NR$^a$R$^b$ wherein R$^a$ and R$^b$ are independently selected from the group consisting of hydrogen atoms, methyl and ethyl groups or R$^a$ represents a hydrogen atom and R$^b$ represents an alkanoyloxymethyl group in which the alkanoyl part has from 1 to 5 carbon atoms, a benzylamino group, an alkanoylamino group having from 1 to 18 carbon atoms, an alkenoylamino group having 3 or 4 carbon atoms, a cycloalkylcarbonylamino group having 6 or 7 carbon atoms, a benzoylamino group which is unsubstituted or is substituted by at least one substituent selected from the group consisting of substituents D', defined below, an alkoxycarbonylamino group having from 2 to 5 carbon atoms or a benzyloxycarbonylamino group which is unsubstituted or is substituted by at least one substituent selected from the group consisting of substituents D', defined below; and said substituents D' are selected from the group consisting of fluorine atoms, chlorine atoms, methyl groups and methoxy groups.

(D) Y represents an oxygen or sulfur atom.

Of these, we prefer those compounds in which R$^1$ is as defined in (A) above, R$^2$ is as defined in (B) above, R$^3$ is as defined in (C) above and Y is as defined in (D) above.

More preferred classes of compounds of the present invention are those compounds of formulae (I) and tautomers and salts thereof in which:

(E) R$^1$ represents a hydrogen atom, a methyl group, an ethyl group, a halogen atom, a methyl group substituted by at least one fluorine atom, a hydroxy group, a methoxy group, an ethoxy group, a methoxy group substituted by at least one fluorine atom, a methylthio group, a methylthio group substituted by at least one fluorine atom, a formyl group, an acetyl group, an acetyl group substituted by at least one fluorine atom, an alkoxycarbonyl group having from 2 to 4 carbon atoms, a carbamoyl group, a cyano group, a nitro group, a methanesulfonyl group, an ethanesulfonyl group, a methanesulfonyl group substituted by at least one fluorine atom, or a sulfamoyl group.

(F) R$^2$ represents an alkanoyl group having from 2 to 6 carbon atoms, a substituted alkanoyl group which has from 2 to 6 carbon atoms and which is substituted by at least one fluorine atom, a cycloalkylcarbonyl group having from 4 to 7 carbon atoms, or a substituted cyclcalkylcarbonyl group which is substituted by at least one fluorine atom.

(G) R$^3$ represents a hydrogen atom, a hydroxy group, a methoxy group, an ethoxy group, a t-butoxy group, a methoxymethoxy group, an alkanoyloxymethoxy group in which the alkanoyl part has from 1 to 5 carbon atoms, a benzyloxy group, an alkanoyloxy group having from 1 to 12 carbon atoms, an alkenoyloxy group having 3 or 4 carbon atoms, a cycloalkylcarbonyloxy group having from 4 to 7 carbon atoms, a benzoyloxy group, an alkoxycarbonyloxy group having from 2 to 5 carbon atoms, a benzyloxycarbonyloxy group, a phthalidyloxy group, a (5-methyl-2-oxo-1,3-dioxolen-4-yl)methoxy group, a (5-phenyl-2-oxo-1,3-dioxolen-4-yl)methoxy group, an amino group or a t-butoxycarbonylamino group.

Of these, we prefer those compounds in which R$^1$ is as defined in (E) above, R$^2$ is as defined in (F) above, R$^3$ is as defined in (G) above and Y is as defined in (D) above.

Still more preferred classes of compounds of the present invention are those compounds of formulae (I) and tautomers and salts thereof in which:

(H) R$^1$ represents a halogen atom, a trifluoromethyl group, a hydroxy group, a difluoromethoxy group, a trifluoromethoxy group, a difluoromethylthio group, a trifluoromethylthio group, a formyl group, an acetyl group, a trifluoroacetyl group, a cyano group or a nitro group.

(I) R$^3$ represents a hydrogen atom, a hydroxy group, a pivaloyloxymethoxy group, an alkanoyloxy group having from 2 to 10 carbon atoms, an alkoxycarbonyloxy group having from 2 to 5 carbon atoms or a (5-methyl-2-oxo-1,3-dioxolen-4-yl)methoxy group.

(J) Y represents a sulfur atom.

Of these, we prefer those compounds in which R$^1$ is as defined in (H) above, R$^2$ is as defined in (F) above, R$^3$ is as defined in (I) above and Y is as defined in (J) above.

The most preferred classes of compounds of the present invention are those compounds of formulae (I) and tautomers and salts thereof in which:

(K) R$^1$ represents a fluorine or chlorine atom.

(L) R$^2$ represents an acetyl group, a propionyl group, a substituted acetyl or propionyl group which is substituted by at least one fluorine atom, a cyclopropylcarbonyl group, cyclobutylcarbonyl group, or a substituted cyclopropylcarbonyl or cyclobutylcarbonyl group which is substituted by at least one fluorine atom.

(M) R$^3$ represents a hydrogen atom, a hydroxy group, a pivaloyloxymethoxy group, an alkanoyloxy group having from 2 to 6 carbon atoms or an alkoxycarbonyloxy group having from 2 to 5 carbon atoms.

Of these, we prefer those compounds in which R$^1$ is as defined in (K) above, R$^2$ is as defined in (L) above, R$^3$ is as defined in (M) above and Y is as defined in (J) above.

In all of the above classes of compounds, we prefer that n should be from 1 to 3, especially 1 or 2, and most preferably 1.

Specific examples of preferred compounds of the present invention are those compounds of formula (II) or (IIa), in which R$^x$, R$^2$, R$^3$/Z and Y are as defined in the following Table 1. In the column headed "R$^3$/Z", the "R$^3$" applies to compounds of formula (II), whilst "Z" applies to compounds of formula (IIa):

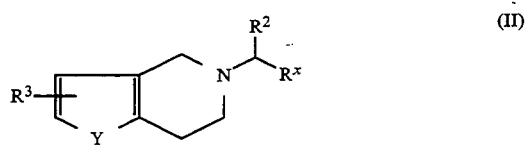

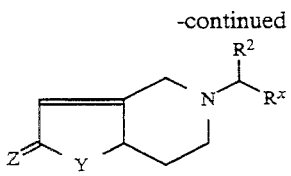

(IIa)

In the Table, the following abbreviations are used refer to certain substituent groups:

| | |
|---|---|
| Ac | acetyl |
| Acr | acryloyl |
| tBoc | t-butoxycarbonyl |
| Boz | benzoyl |
| cBu | cyclobutyl |
| tBu | t-butyl |
| Bun | butenoyl |
| Byr | butyryl |
| iByr | isobutyryl |
| Bz | benzyl |
| Bzc | benzyloxycarbonyl |
| Car | carbamoyl |
| Dcn | decanoyl |
| Ddoz | 5,6-dihydro-1,4,2-dioxazin-3-yl |
| Et | ethyl |
| Etc | ethoxycarbonyl |
| Fo | formyl |
| cHp | cycloheptyl |
| cHx | cyclohexyl |
| Hxn | hexanoyl |
| Lau | lauroyl |
| Me | methyl |
| Mec | methoxycarbonyl |
| Mod | (5-methyl-2-oxo-1,3-dioxolen-4-yl)methyl |
| Nnn | nonanoyl |
| Plt | palmitoyl |
| Ph | phenyl |
| Phth | phthalidyl |
| Piv | pivaloyl |
| cPn | cyclopentyl |
| cPr | cyclopropyl |
| Prn | propionyl |
| Va | valeryl |
| iVa | isovaleryl |

TABLE 1

| Cpd. No. | Formula | $R^x$ | $R^2$ | $R^3/Z$ | Y |
|---|---|---|---|---|---|
| 1 | (II) | Ph | Ddoz | H | S |
| 2 | (II) | 2-FPh | Ddoz | H | S |
| 3 | (II) | 2-ClPh | Ddoz | H | S |
| 4 | (II) | 2-CNPh | Ddoz | H | S |
| 5 | (II) | 2-NO$_2$Ph | Ddoz | H | S |
| 6 | (II) | 2-CHF$_2$Ph | Ddoz | H | S |
| 7 | (II) | 2,6-diFPh | Ddoz | H | S |
| 8 | (II) | 2-F,6-ClPh | Ddoz | H | S |
| 9 | (II) | 2-FPh | Ac | H | S |
| 10 | (II) | 2-ClPh | Ac | H | S |
| 11 | (II) | 2-CNPh | Ac | H | S |
| 12 | (II) | 2-NO$_2$Ph | Ac | H | S |
| 13 | (II) | 2-CF$_3$Ph | Ac | H | S |
| 14 | (II) | 2,6-diFPh | Ac | H | S |
| 15 | (II) | 2-F,6-ClPh | Ac | H | S |
| 16 | (II) | 2,4-diFPh | Ac | H | S |
| 17 | (II) | 2-F,6-CNPh | Ac | H | S |
| 18 | (II) | Ph | Prn | H | S |
| 19 | (II) | 2-FPh | Prn | H | S |
| 20 | (II) | 2-ClPh | Prn | H | S |
| 21 | (II) | 2-BrPh | Prn | H | S |
| 22 | (II) | 2-IPh | Prn | H | S |
| 23 | (II) | 2-HOPh | Prn | H | S |
| 24 | (II) | 2-NO$_2$Ph | Prn | H | S |
| 25 | (II) | 2-Cl,5-NH$_2$Ph | Prn | H | S |
| 26 | (II) | 2-CNPh | Prn | H | S |
| 27 | (II) | 2-F,5-HOOCPh | Prn | H | S |
| 28 | (II) | 2-F,4-MePh | Prn | H | S |
| 29 | (II) | 2-CF$_3$Ph | Prn | H | S |
| 30 | (II) | 2-F,4-MeOPh | Prn | H | S |
| 31 | (II) | 2-CHF$_2$OPh | Prn | H | S |
| 32 | (II) | 2-CF$_3$OPh | Prn | H | S |
| 33 | (II) | 3-CH$_2$FOPh | Prn | H | S |
| 34 | (II) | 4-MeSPh | Prn | H | S |
| 35 | (II) | 2-CHF$_2$SPh | Prn | H | S |
| 36 | (II) | 3-CF$_3$SPh | Prn | H | S |
| 37 | (II) | 2-MeSO$_2$Ph | Prn | H | S |
| 38 | (II) | 2-EtSO$_2$Ph | Prn | H | S |
| 39 | (II) | 2-CF$_3$SO$_2$Ph | Prn | H | S |
| 40 | (II) | 4-CarPh | Prn | H | S |
| 41 | (II) | 3-NH$_2$SO$_2$Ph | Prn | H | S |
| 42 | (II) | 2-FOPh | Prn | H | S |
| 43 | (II) | 2-AcPh | Prn | H | S |
| 44 | (II) | 2-CF$_3$COPh | Prn | H | S |
| 45 | (II) | 2,6-diFPh | Prn | H | S |
| 46 | (II) | 2-F,6-ClPh | Prn | H | S |
| 47 | (II) | 2,4,6-triFPh | Prn | H | S |
| 48 | (II) | 2,3,4,5,6-pentaFPh | Prn | H | S |
| 49 | (II) | 2-F,6-CNPh | Prn | H | S |
| 50 | (II) | 2-F,6-NO$_2$Ph | Prn | H | S |
| 51 | (II) | 2,6-diF,4-MePh | Prn | H | S |
| 52 | (II) | 2,4-diClPh | Prn | H | S |
| 53 | (II) | 2-F,4-HOPh | Prn | H | S |

TABLE 1-continued

| Cpd. No. | Formula | R$^x$ | R$^2$ | R$^3$/Z | Y |
|---|---|---|---|---|---|
| 54 | (II) | 2-Cl,4-MecPh | Prn | H | S |
| 55 | (II) | 2-F,6-CHF$_2$OPh | Prn | H | S |
| 56 | (II) | 2-Cl,4-EtPh | Prn | H | S |
| 57 | (II) | 2-F,5-EtOPh | Prn | H | S |
| 58 | (II) | Ph | cPrCO | H | S |
| 59 | (II) | 2-FPh | cPrCO | H | S |
| 60 | (II) | 2-ClPh | cPrCO | H | S |
| 61 | (II) | 2-BrPh | cPrCO | H | S |
| 62 | (II) | 2-IPh | cPrCO | H | S |
| 63 | (II) | 2-HOPh | cPrCO | H | S |
| 64 | (II) | 2-NO$_2$Ph | cPrCO | H | S |
| 65 | (II) | 2-Cl,5-NH$_2$Ph | cPrCO | H | S |
| 66 | (II) | 2-CNPh | cPrCO | H | S |
| 67 | (II) | 2-F,5-HOOCPh | cPrCO | H | S |
| 68 | (II) | 2-F,4-MePh | cPrCO | H | S |
| 69 | (II) | 2-CF$_3$Ph | cPrCO | H | S |
| 70 | (II) | 2-F,4-MeOPh | cPrCO | H | S |
| 71 | (II) | 2-CHF$_2$OPh | cPrCO | H | S |
| 72 | (II) | 2-CF$_3$OPh | cPrCO | H | S |
| 73 | (II) | 3-CH$_2$FOPh | cPrCO | H | S |
| 74 | (II) | 4-MeSPh | cPrCO | H | S |
| 75 | (II) | 2-CHF$_2$SPh | cPrCO | H | S |
| 76 | (II) | 3-CF$_3$SPh | cPrCO | H | S |
| 77 | (II) | 2-MeSO$_2$Ph | cPrCO | H | S |
| 78 | (II) | 2-EtSO$_2$Ph | cPrCO | H | S |
| 79 | (II) | 2-CF$_3$SO$_2$Ph | cPrCO | H | S |
| 80 | (II) | 4-CarPh | cPrCO | H | S |
| 81 | (II) | 3-NH$_2$SO$_2$Ph | cPrCO | H | S |
| 82 | (II) | 2-FOPh | cPrCO | H | S |
| 83 | (II) | 2-AcPh | cPrCO | H | S |
| 84 | (II) | 2-CF$_3$COPh | cPrCO | H | S |
| 85 | (II) | 2,6-diFPh | cPrCO | H | S |
| 86 | (II) | 2-F,6-ClPh | cPrCO | H | S |
| 87 | (II) | 2,4,6-triFPh | cPrCO | H | S |
| 88 | (II) | 2,3,4,5,6-pentaFPh | cPrCO | H | S |
| 89 | (II) | 2-F,6-CNPh | cPrCO | H | S |
| 90 | (II) | 2-F,6-NO$_2$Ph | cPrCO | H | S |
| 91 | (II) | 2,6-diF,4-MePh | cPrCO | H | S |
| 92 | (II) | 2,4-diClPh | cPrCO | H | S |
| 93 | (II) | 2-F,4-HOPh | cPrCO | H | S |
| 94 | (II) | 2-Cl,4-EtcPh | cPrCO | H | S |
| 95 | (II) | 2-F,6-CHF$_2$OPh | cPrCO | H | S |
| 96 | (II) | 2-Cl,4-EtPh | cPrCO | H | S |
| 97 | (II) | 2-F,5-EtOPh | cPrCO | H | S |
| 98 | (II) | 2-FPh | 3-FPrn | H | S |
| 99 | (II) | 2-ClPh | 3-FPrn | H | S |
| 100 | (II) | 2-CNPh | 3-FPrn | H | S |
| 101 | (II) | 2,6-diFPh | 3-FPrn | H | S |
| 102 | (II) | 2-F,6-ClPh | 3-FPrn | H | S |
| 103 | (II) | 2-F,6-CNPh | 3-FPrn | H | S |
| 104 | (II) | 2-NO$_2$Ph | 3-FPrn | H | S |
| 105 | (II) | 2-F,4-CNPh | 3-FPrn | H | S |
| 106 | (II) | 2-FPh | cBuCO | H | S |
| 107 | (II) | 2-ClPh | cBuCO | H | S |
| 108 | (II) | 2-CNPh | cBuCO | H | S |
| 109 | (II) | 2-FPh | HOCH$_2$CO | H | S |
| 110 | (II) | 2-ClPh | HOCH$_2$CO | H | S |
| 111 | (II) | 2-CNPh | CF$_3$CO | H | S |
| 112 | (II) | 2-FPh | CF$_3$CO | H | S |
| 113 | (II) | 2-ClPh | CF$_3$CO | H | S |
| 114 | (II) | 2-FPh | Fo | H | S |
| 115 | (II) | 2-ClPh | Fo | H | S |
| 116 | (II) | 2-FPh | Byr | H | S |
| 117 | (II) | 2-ClPh | Byr | H | S |
| 118 | (II) | 2-FPh | iByr | H | S |
| 119 | (II) | 2-ClPh | iByr | H | S |
| 120 | (II) | 2-FPh | Va | H | S |
| 121 | (II) | 2-ClPh | Va | H | S |
| 122 | (II) | 2-FPh | Piv | H | S |
| 123 | (II) | 2-F,6-ClPh | Piv | H | S |
| 124 | (II) | 2-FPh | iVa | H | S |
| 125 | (II) | 2-ClPh | Hxn | H | S |
| 126 | (II) | 2-FPh | Dcn | H | S |
| 127 | (II) | 2-ClPh | 1-Bun | H | S |
| 128 | (II) | 2-FPh | cPnCO | H | S |
| 129 | (II) | 2-FPh | cHxCO | H | S |
| 130 | (II) | 2-FPh | cHpCO | H | S |
| 131 | (II) | 2-FPh | CH$_2$FCO | H | S |
| 132 | (II) | 2-FPh | CHF$_2$CO | H | S |
| 133 | (II) | 2-ClPh | CHF$_2$CO | H | S |

TABLE 1-continued

| Cpd. No. | Formula | R$^x$ | R$^2$ | R$^3$/Z | Y |
|---|---|---|---|---|---|
| 134 | (II) | 2-CNPh | CHF$_2$CO | H | S |
| 135 | (II) | 2-FPh | MeO—CH$_2$CO | H | S |
| 136 | (II) | 2-ClPh | MeO—CH$_2$CO | H | S |
| 137 | (II) | 2-FPh | NC—CH$_2$CO | H | S |
| 138 | (II) | 2-ClPh | NC—CH$_2$CO | H | S |
| 139 | (II) | 2,6-diFPh | NC—CH$_2$CO | H | S |
| 140 | (II) | 2-FPh | 3-ClPrn | H | S |
| 141 | (II) | 2-ClPh | 3-ClPrn | H | S |
| 142 | (II) | 2-FPh | 3-HOPrn | H | S |
| 143 | (II) | 2-ClPh | 3-HOPrn | H | S |
| 144 | (II) | 2-FPh | 3-MeOPrn | H | S |
| 145 | (II) | 2-FPh | 3-CNPrn | H | S |
| 146 | (II) | 2-FPh | 4-FByr | H | S |
| 147 | (II) | 2-ClPh | 4-ClByr | H | S |
| 148 | (II) | 2-FPh | 4-FBoz | H | S |
| 149 | (II) | 2-ClPh | 4-FBoz | H | S |
| 150 | (II) | 2-CNPh | 4-FBoz | H | S |
| 151 | (II) | 2-FPh | 2,4-diFBoz | H | S |
| 152 | (II) | 2-ClPh | 2,4-diFBoz | H | S |
| 153 | (II) | 2-NO$_2$Ph | 2,4-diFBoz | H | S |
| 154 | (II) | 2-FPh | 3-BrPrn | H | S |
| 155 | (II) | 2-FPh | 3-IPrn | H | S |
| 156 | (II) | 2-FPh | Ac | H | O |
| 157 | (II) | 2-ClPh | Ac | H | O |
| 158 | (II) | 2-CNPh | Ac | H | O |
| 159 | (II) | 2-NO$_2$Ph | Ac | H | O |
| 160 | (II) | 2-FPh | Prn | H | O |
| 161 | (II) | 2-ClPh | Prn | H | O |
| 162 | (II) | 2-CNPh | Prn | H | O |
| 163 | (II) | 2-NO$_2$Ph | Prn | H | O |
| 164 | (II) | 2-FPh | 3-FPrn | H | O |
| 165 | (II) | 2-ClPh | 3-FPrn | H | O |
| 166 | (II) | 2-CNPh | 3-FPrn | H | O |
| 167 | (II) | 2-NO$_2$Ph | 3-FPrn | H | O |
| 168 | (II) | 2-FPh | cPrCO | H | O |
| 169 | (II) | 2-ClPh | cPrCO | H | O |
| 170 | (II) | 2-CNPh | cPrCO | H | O |
| 171 | (II) | 2-NO$_2$Ph | cPrCO | H | O |
| 172 | (II) | 2,6-diFPh | cPrCO | H | O |
| 173 | (II) | 2-F,6-ClPh | cPrCO | H | O |
| 174 | (II) | 2,6-diFPh | 4-FBoz | H | S |
| 175 | (II) | 2-FPh | cPrCO | 2-NO$_2$ | S |
| 176 | (II) | 2-FPh | cPrCO | 2-NH$_2$ | O |
| 177 | (II) | 2-FPh | cPrCO | 2-NH$_2$ | S |
| 178 | (II) | 2-FPh | cPrCO | 2-AcNH | O |
| 179 | (II) | 2-FPh | cPrCO | 2-AcNH | S |
| 180 | (II) | 2-FPh | cPrCO | 2-ByrNH | O |
| 181 | (II) | 2-FPh | cPrCO | 2-ByrNH | S |
| 182 | (II) | 2-FPh | cPrCO | 2-PivNH | S |
| 183 | (II) | 2-FPh | cPrCO | 2-tBocNH | O |
| 184 | (II) | 2-FPh | cPrCO | 2-tBocNH | S |
| 185 | (II) | 2-FPh | cPrCO | 2-HO | O |
| 186 | (II) | 2-ClPh | cPrCO | 2-HO | S |
| 187 | (II) | 2-FPh | Prn | 2-HO | S |
| 188 | (II) | 2-FPh | cPrCO | 2-HO | S |
| 189 | (II) | 2-FPh | cPrCO | 2-AcO | O |
| 190 | (II) | 2-FPh | cPrCO | 2-AcO | S |
| 191 | (II) | 2-FPh | cPrCO | 2-PrnO | O |
| 192 | (II) | 2-FPh | cPrCO | 2-PrnO | S |
| 193 | (II) | 2-FPh | cPrCO | 2-ByrO | O |
| 194 | (II) | 2-FPh | cPrCO | 2-ByrO | S |
| 195 | (II) | 2-FPh | cPrCO | 2-PivO | O |
| 196 | (II) | 2-FPh | cPrCO | 2-PivO | S |
| 197 | (II) | 2-FPh | cPrCO | 2-VaO | S |
| 198 | (II) | 2-FPh | cPrCO | 2-HxnO | S |
| 199 | (II) | 2-FPh | cPrCO | 2-NnnO | S |
| 200 | (II) | 2-FPh | cPrCO | 2-DcnO | S |
| 201 | (II) | 2-FPh | cPrCO | 2-PltO | S |
| 202 | (II) | 2-FPh | cPrCO | 2-BozO | S |
| 203 | (II) | 2-FPh | cPrCO | 2-tBocO | S |
| 204 | (II) | 2-FPh | cPrCO | 2-tBuO | S |
| 205 | (II) | 2-FPh | cPrCO | 2-BzO | S |
| 206 | (II) | 2-FPh | cPrCO | 2-MeOCH$_2$O | S |
| 207 | (II) | 2-FPh | cPrCO | 2-PivOCH$_2$O | S |
| 208 | (II) | 2-FPh | cPrCO | 2-PhthO | S |
| 209 | (II) | 2-FPh | cPrCO | 2-ModO | S |
| 210 | (II) | 2-FPh | cPrCO | 2-MeO | S |
| 211 | (II) | 2-FPh | cPrCO | 2-EtO | S |
| 212 | (II) | 2-FPh | cPrCO | 2-LauO | S |
| 213 | (II) | 2-FPh | cPrCO | 2-AcrO | S |

TABLE 1-continued

| Cpd. No. | Formula | R$^x$ | R$^2$ | R$^3$/Z | Y |
|---|---|---|---|---|---|
| 214 | (II) | 2-FPh | cPrCO | 2-cHxCOO | S |
| 215 | (II) | 2-FPh | cPrCO | 2-MecO | S |
| 216 | (II) | 2-FPh | cPrCO | 2-EtcO | S |
| 217 | (II) | 2-FPh | cPrCO | 2-FoNH | S |
| 218 | (II) | 2-FPh | cPrCO | 2-PrnNH | S |
| 219 | (II) | 2-FPh | cPrCO | 2-MeNH | S |
| 220 | (II) | 2-FPh | cPrCO | 2-EtNH | S |
| 221 | (II) | 2-FPh | cPrCO | 2-NMe$_2$ | S |
| 222 | (II) | 2-FPh | cPrCO | 2-AcrNH | S |
| 223 | (II) | 2-FPh | cPrCO | 2-cHxCONH | S |
| 224 | (II) | 2-FPh | cPrCO | 2-MecNH | S |
| 225 | (II) | 2-FPh | cPrCO | 2-EtcNH | S |
| 226 | (II) | 2-FPh | cPrCO | 2-BozNH | S |
| 227 | (II) | 2-FPh | cPrCO | 2-BozO | O |
| 228 | (II) | 2-FPh | cPrCO | 2-tBocO | O |
| 229 | (II) | 2-FPh | Prn | 2-NO$_2$ | S |
| 230 | (II) | 2-FPh | cPrCO | 2-BzcO | S |
| 231 | (II) | 2-FPh | cPrCO | 2-BzcNH | S |
| 232 | (IIa) | 2-FPh | cPrCO | O | O |
| 233 | (IIa) | 2-ClPh | cPrCO | O | S |
| 234 | (IIa) | 2-FPh | Prn | O | S |
| 235 | (IIa) | 2-FPh | cPrCO | O | S |
| 236 | (II) | 2-FPh | Prn | 2-AcO | S |
| 237 | (II) | 2-FPh | Prn | 2-PrnO | S |
| 238 | (II) | 2-FPh | Prn | 2-ByrO | S |
| 239 | (II) | 2-FPh | Prn | 2-PivO | S |
| 240 | (II) | 2-FPh | Prn | 2-VaO | S |
| 241 | (II) | 2-FPh | Prn | 2-HxnO | S |
| 242 | (II) | 2-FPh | Prn | 2-MecO | S |
| 243 | (II) | 2-FPh | Prn | 2-EtcO | S |
| 244 | (II) | 2-FPh | Prn | 2-tBocO | S |
| 245 | (II) | 2-FPh | Prn | 2-BozO | S |
| 246 | (II) | 2-FPh | Prn | 2-NH$_2$ | S |
| 247 | (II) | 2-FPh | Prn | 2-AcNH | S |
| 248 | (II) | 2-FPh | Prn | 2-PrnNH | S |
| 249 | (II) | 2-FPh | Prn | 2-ByrNH | S |
| 250 | (II) | 2-FPh | Prn | 2-tBocNH | S |
| 251 | (II) | 2-FPh | Prn | 2-BzcNH | S |
| 252 | (II) | 2-ClPh | cPrCO | 2-AcO | S |
| 253 | (II) | 2-ClPh | cPrCO | 2-PrnO | S |
| 254 | (II) | 2-ClPh | cPrCO | 2-ByrO | S |
| 255 | (II) | 2-ClPh | cPrCO | 2-PivO | S |
| 256 | (II) | 2-ClPh | cPrCO | 2-VaO | S |
| 257 | (II) | 2-ClPh | cPrCO | 2-HxnO | S |
| 258 | (II) | 2-ClPh | cPrCO | 2-MecO | S |
| 259 | (II) | 2-ClPh | cPrCO | 2-EtcO | S |
| 260 | (II) | 2-ClPh | cPrCO | 2-tBocO | S |
| 261 | (II) | 2-ClPh | cPrCO | 2-BozO | S |
| 262 | (II) | 2-ClPh | cPrCO | 2-NH$_2$ | S |
| 263 | (II) | 2-ClPh | cPrCO | 2-AcNH | S |
| 264 | (II) | 2-ClPh | cPrCO | 2-PrnNH | S |
| 265 | (II) | 2-ClPh | cPrCO | 2-ByrNH | S |
| 266 | (II) | 2-ClPh | cPrCO | 2-tBocNH | S |
| 267 | (II) | 2-ClPh | cPrCO | 2-BzcNH | S |
| 268 | (II) | 2-FPh | cPrCO | 2-MeOCH$_2$NH | S |
| 269 | (II) | 2-FPh | cPrCO | 2-PhthNH | S |
| 270 | (II) | 2-FPh | cPrCO | 2-ModNH | S |
| 271 | (II) | 2-FPh | cPrCO | 2-PivOCH$_2$NH | S |
| 272 | (II) | 2-FPh | 2-FcPrCO | H | S |
| 273 | (II) | 2-FPh | 2-FcPrCO | H | O |
| 274 | (II) | 2-FPh | 2-FcPrCO | 2-OH | S |
| 275 | (IIa) | 2-FPh | 2-FcPrCO | O | S |
| 276 | (II) | 2-FPh | 2-FcPrCO | 2-AcO | S |
| 277 | (II) | 2-FPh | 2-FcPrCO | 2-ByrO | S |
| 278 | (II) | 2-FPh | 2-FcPrCO | 2-PivO | S |
| 279 | (II) | 2-FPh | 2-FcPrCO | 2-PivOCH$_2$O | S |
| 280 | (II) | 2-ClPh | 2-FcPrCO | H | S |
| 281 | (II) | 2-ClPh | 2-FcPrCO | 2-OH | S |
| 282 | (IIa) | 2-ClPh | 2-FcPrCO | O | S |
| 283 | (II) | 2-ClPh | 2-FcPrCO | 2-AcO | S |
| 284 | (II) | 2-ClPh | 2-FcPrCO | 2-ByrO | S |
| 285 | (II) | 2-ClPh | 2-FcPrCO | 2-PivO | S |
| 286 | (II) | 2-ClPh | 2-FcPrCO | 2-PivOCH$_2$O | S |
| 287 | (II) | 2-FPh | 2,2-diFcPrCO | H | S |
| 288 | (II) | 2-FPh | 2,2-diFcPrCO | 2-OH | S |
| 289 | (IIa) | 2-FPh | 2,2-diFcPrCO | O | S |
| 290 | (II) | 2-FPh | 2,2-diFcPrCO | 2-AcO | S |
| 291 | (II) | 2-FPh | 2,2-diFcPrCO | 2-ByrO | S |

Of the compounds listed above, the following are preferred, that is to say Compounds No. 2, 3, 7, 9, 10, 11, 12, 19, 20, 24, 26, 29, 58, 59, 60, 61, 62, 63, 64, 65, 66, 67, 68, 69, 70, 71, 72, 73, 74, 75, 76, 77, 78, 79, 80, 81, 82, 83, 84, 85, 86, 89, 90, 98, 99, 106, 107, 108, 109, 111, 112, 113, 114, 116, 117, 118, 119, 120, 121, 122, 124, 125, 128, 129, 131, 132, 133, 135, 137, 140, 142, 144, 149, 151, 156, 160, 168, 177, 184, 186, 187, 188, 190, 192, 194, 196, 197, 198, 199, 200, 201, 203, 204, 206, 207, 208, 209, 210, 233, 234, 235, 236, 238, 239, 252, 253, 254, 255, 274, 275, 276, 277, 278, 279, 280, 281, 282, 283, 284, 285, 286, 287, 288, 289 and 290, of which Compounds No. 9, 10, 19, 20, 59, 60, 63, 64, 66, 69, 71, 72, 75, 76, 83, 84, 85, 86, 98, 106, 113, 116, 118, 120, 122, 125, 128, 129, 131, 132, 186, 187, 188, 190, 192, 194, 196, 197, 198, 199, 200, 203, 207, 209, 233, 234, 235, 236, 238, 239, 252, 253, 254, 255, 274, 275, 276, 277, 278, 279, 281, 282, 283, 284, 285 and 286 are more preferred.

The most preferred compounds are Compounds No.:
19. 5-(2-Fluoro-α-propionylbenzyl)-4,5,6,7-tetrahydrothieno[3,2-c]pyridine;
59. 5-(α-Cyclopropylcarbonyl-2-fluorobenzyl)-4,5,6,7-tetrahydrothieno[3,2-c]pyridine;
60. 5-(2-Chloro-α-cyclopropylcarbonylbenzyl)-4,5,6,7-tetrahydrothieno[3,2-c]pyridine;
190. 2-Acetoxy-5-(α-cyclopropylcarbonyl-2-fluorobenzyl)-4,5,6,7-tetrahydrothieno[3,2-c]pyridine;
192. 5-(α-Cyclopropylcarbonyl-2-fluorobenzyl)-2-propionyloxy-4,5,6,7-tetrahydrothieno[3,2-c]pyridine;
194. 2-Butyryloxy-5-(α-cyclopropylcarbonyl-2-fluorobenzyl)-4,5,6,7-tetrahydrothieno[3,2-c]pyridine;
196. 5-(α-Cyclopropylcarbonyl-2-fluorobenzyl)-2-pivaloyloxy-4,5,6,7-tetrahydrothieno[3,2-c]pyridine;
197. 5-(α-Cyclopropylcarbonyl-2-fluorobenzyl)-2-valeryloxy-4,5,6,7-tetrahydrothieno[3,2-c]pyridine;
198. 5-(α-Cyclopropylcarbonyl-2-fluorobenzyl)-2-hexanoyloxy-4,5,6,7-tetrahydrothieno[3,2-c]pyridine;
203. 2-t-Butoxycarbonyloxy-5-(α-cyclopropylcarbonyl-2-fluorobenzyl)-4,5,6,7-tetrahydrothieno[3,2-c]pyridine;
207. 5-(α-Cyclopropylcarbonyl-2-fluorobenzyl)-2-pivaloyloxymethoxy-4,5,6,7-tetrahydrothieno[3,2-c]pyridine;
233. 5-(2-Chloro-α-cyclopropylcarbonylbenzyl)-2-oxo-2,4,5,6,7,7a-hexahydrothieno[3,2-c]pyridine and its tautomer;
234. 5-(2-Fluoro-α-propionylbenzyl)-2-oxo-2,4,5,6,7,7a-hexahydrothieno[3,2-c]pyridine and its tautomer;
235. 5-(α-Cyclopropylcarbonyl-2-fluorobenzyl)-2-oxo-2,4,5,6,7,7a-hexahydrothieno[3,2-c]pyridine and its tautomer;
252. 2-Acetoxy-5-(2-chloro-α-cyclopropylcarbonylbenzyl)-4,5,6,7-tetrahydrothieno[3,2-c]pyridine;
275. 5-[α-(2-Fluorocyclopropylcarbonyl-2-fluorobenzyl]-2-oxo-2,4,5,6,7,7a-hexahydrothieno[3,2-c]pyridine and its tautomer;
276. 2-Acetoxy-5-[α-(2-fluorocyclopropylcarbonyl-2-fluorobenzyl]-4,5,6,7-tetrahydrothieno[3,2-c]pyridine.

The compounds of the present invention can be prepared by a variety of methods, whose general techniques are known in the art for the preparation of compounds of this type. For example, they may be prepared by reacting a compound of formula (III):

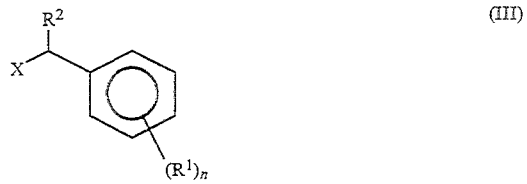

(in which $R^1$, $R^2$ and n are as defined above and X represents a halogen atom, for example a fluorine, chlorine, bromine or iodine atom, preferably a chlorine or bromine atom) with a compound of formula (IV):

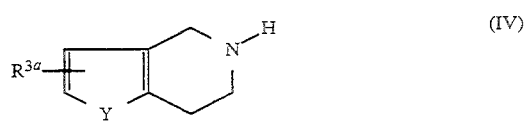

(in which Y is as defined above and $R^{3a}$ represents a hydrogen atom or a hydroxy or nitro group) to give a compound of formula (Ic):

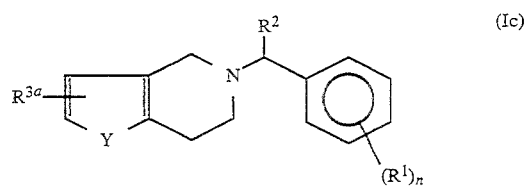

(in which $R^1$, $R^2$, $R^{3a}$, n and Y are as defined above).

If required, this compound of formula (Ic) may then be subjected to one or more appropriate reactions, as explained in more detail hereafter, to convert the hydroxy or nitro group represented by $R^{3a}$ to any other group represented by $R^3$, as defined above.

These reactions may be summarized in the following Reaction Scheme A:

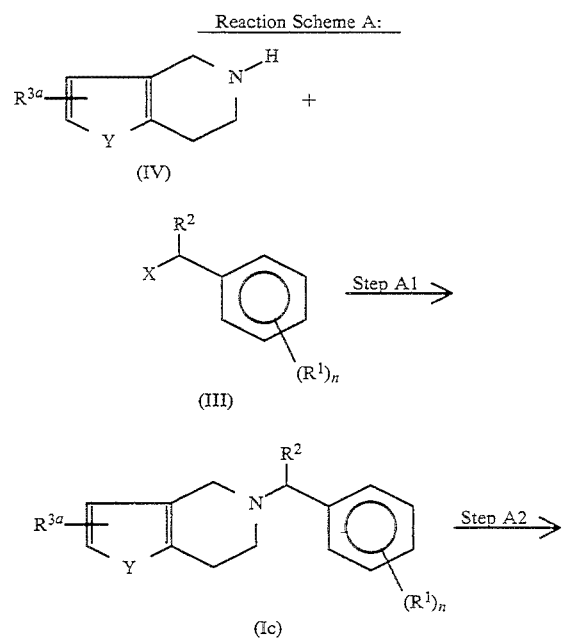

Reaction Scheme A:
-continued

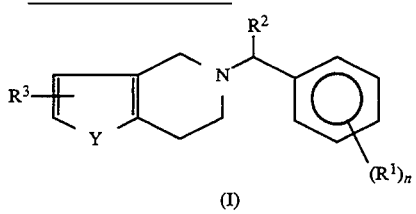

(I)

In the above formulae, $R^1$, $R^2$, $R^3$, $R^{3a}$, X, Y and n are as defined above.

In Step A1 of this Reaction Scheme, the substituted benzyl halide of formula (III) is reacted with a condensed hydropyridyl compound of formula (iV), to give the compound of formula (Ic). This reaction may be carried out in the presence or absence of an inert solvent (preferably in the presence of an inert solvent) and in the presence or absence of a base (preferably in the presence of a base).

There is no specific limitation on the nature of the base employed, and any base known for use in reactions of this type may equally be used here. Examples of suitable bases include: organic amines, such as triethylamine, tributylamine, N-methylmorpholine, pyridine, 4-dimethylaminopyridine, picoline, lutidine, collidine, 1,8-diazabicyclo[5.4.0]undec-7-ene or 1,5-diazabicyclo[4.3.0]non-5-ene; alkali metal alkoxides, such as sodium methoxide, sodium ethoxide or potassium t-butoxide; alkali metal carbonates, such as sodium carbonate or potassium carbonate; and alkali metal hydroxides, such as sodium hydroxide or potassium hydroxide. Of these, the alkali metal carbonates are preferred. The amount of base employed is not critical, but we would generally recommend an amount of base of from an equimolar amount to 5 times the equimolar amount with respect to the starting material of formula (III). Where an excess of the starting material of formula (IV) is employed, this may also function as the base. Also, if an excess of an organic amine is employed as the base, this may additionally serve as the solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; ketones, such as acetone or methyl ethyl ketone; esters, such as ethyl acetate; alcohols, such as methanol, ethanol, propanol, isopropanol or butanol; nitriles, such as acetonitrile; amides, such as N,N-dimethylformamide, N,N-dimethylacetamide, N-methyl-2-pyrrolidone or hexamethylphosphoric triamide; and sulfoxides, such as dimethyl sulfoxide. Of these, the amides or the sulfoxides are preferred.

The reaction can take place over a wide range of temperatures, and the precise reaction temperature is not critical to the invention. In general, we find it convenient to carry out the reaction at a temperature of from 0° C. to 200° C. (more preferably at from about room temperature to 150° C.). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 2 to 15 hours) will usually suffice.

After completion of the reaction, the desired compound of formula (Ic) can be obtained from the reaction mixture by conventional means. For example, if the compound is produced immediately in the form of crystals, these can be separated simply by filtration. Alternatively, a suitable recovery procedure comprises: adding water; neutralizing the mixture, if necessary; extracting the mixture with a water-immiscible organic solvent; drying the extract; and distilling the solvent off. If necessary, the product thus obtained can be further purified by conventional means, such as recrystallization or the various chromatography techniques, for example preparative thin layer chromatography or column chromatography, notably column chromatography.

In the optional second step of this reaction, Step A2, the resulting compound of formula (Ic) is converted, if desired, to a compound of formula (I). This reaction may involve any one or more of the following reactions:

(1) where $R^{3a}$ represents a hydroxy group, alkylation, aralkylation or acylation of this hydroxy group;

(2) Where $R^{3a}$ represents a nitro group, conversion of this nitro group to an amino group;

(3) Alkylation, aralkylation or acylation of the amino group obtained as described in (2) above.

Alkylation, aralkylation or acylation of the hydroxy group in Step A2(1) is carried out in an inert solvent and in the presence of a base by reacting a hydroxy compound of formula (Ic) ($R^{3a}$ represents a hydroxy group) with a corresponding alkylating, aralkylating or acylating agent, for example an alkyl halide, aralkyl halide, acyl halide or acid anhydride. The nature of this compound will, of course, depend on the nature of the group which it is desired to introduce into the compound of formula (I). However, examples of suitable compounds are as follows:

alkyl halides having from 1 to 4 carbon atoms, such as methyl iodide, ethyl bromide, ethyl iodide, propyl chloride, propyl bromide, butyl chloride or butyl iodide;

aralkyl halides having from 7 to 14 carbon atoms, such as benzyl chloride, benzyl bromide, p-methylbenzyl chloride, p-methoxybenzyl chloride, p-chlorobenzyl chloride, p-fluorobenzyl chloride or naphthylmethyl chloride;

alkyl halides from 1 to 4 carbon atoms which are substituted by an alkoxy group having from 1 to 4 carbon atoms, by an alkanoyloxy group having from 1 to 6 carbon atoms or by an arylcarbonyloxy group having from 7 to 11 carbon atoms, such as methoxymethyl chloride, 1-methoxyethyl chloride, 2-methoxyethyl chloride, 1-methoxypropyl chloride, 1-methoxybutyl chloride, ethoxymethyl chloride, propoxymethyl chloride, butoxymethyl chloride, acetoxymethyl chloride, 1-acetoxyethyl chloride, 2-acetoxyethyl chloride, 1-acetoxypropyl chloride, 1-acetoxybutyl chloride, propionyloxymethyl chloride, butyryloxymethyl chloride, valeryloxymethyl chloride, pivaloyloxymethyl chloride, benzoyloxymethyl chloride, 1-benzoyloxyethyl chloride, p-methylbenzoyloxymethyl chloride, p-methoxybenzoyloxymethyl chloride, p-chlorobenzoyloxymethyl chloride, p-fluorobenzoyloxymethyl chloride or naphthoyloxymethyl chloride;

alkanoyl halides having from 2 to 18 carbon atoms or a mixed acid anhydride of one such corresponding acid with formic acid, such as acetyl chloride, propionyl chloride, butyryl chloride, butyryl bromide, valeryl chloride, isovaleryl chloride, pivaloyl chloride, hexanoyl chloride, nonanoyl chloride, decanoyl chloride, lauroyl chloride, palmitoyl chloride, stearoyl chloride, mixed acid anhydride of formic acid and acetic acid, acetic anhydride, propionic anhydride or butyric anhydride;

alkenoyl chlorides having from 3 to 6 carbon atoms, such as acryloyl chloride, methacryloyl chloride, and crotonoyl chloride or 2-hexenoyl chloride;

cycloalkanecarbonyl halides having from 3 to 7 carbon atoms in the cycloalkane part, such as cyclopropanecarbonyl chloride, cyclobutanecarbonyl chloride, cyclopentanecarbonyl chloride, cyclohexanecarbonyl chloride or cycloheptanecarbonyl chloride;

arylcarbonyl halides having from 6 to 10 carbon atoms in the aryl part, such as benzoyl chloride, p-methylbenzoyl chloride, p-methoxybenzoyl chloride, p-chlorobenzoyl chloride, p-fluorobenzoyl chloride or naphthoyl chloride;

alkoxycarbonyl halides having from 1 to 4 carbon atoms in the alkoxy part, or an alkyl carbonate anhydride having from 1 to 4 carbon atoms in the alkyl part, such as methoxycarbonyl chloride, ethoxycarbonyl chloride, propoxycarbonyl chloride, isopropoxycarbonyl chloride, butoxycarbonyl chloride, t-butoxycarbonyl chloride, dimethyl dicarbonate, diethyl dicarbonate, dipropyl dicarbonate, diisopropyl dicarbonate, dibutyl dicarbonate or di-t-butyl dicarbonate;

aralkyloxycarbonyl halides having from 7 to 14 carbon atoms in the aralkyl part, such as benzyloxycarbonyl chloride, p-methylbenzyloxycarbonyl chloride, p-methoxybenzyloxycarbonyl chloride, p-chlorobenzyloxycarbonyl chloride, p-fluorobenzyloxycarbonyl chloride or naphthylmethoxycarbonyl chloride;

phthalidyl halides, such as phthalidyl chloride; or substituted methyl halides, such as (5-methyl- or 5-phenyl-2-oxo-1,3-dioxolen-4-yl)methyl chloride.

The base employed is not critical to the invention, provided that it has no adverse effect on other parts of the molecule, and any base commonly used in reactions of this type may equally be used here. Examples of suitable bases include: alkali metal hydrides, such as lithium hydride or sodium hydride; alkali metal alkoxides, such as sodium methoxide, sodium ethoxide or potassium t-butoxide; alkali metal carbonates, such as sodium carbonate or potassium carbonate; and alkali metal hydroxides, such as sodium hydroxide or potassium hydroxide. Of these, the alkali metal hydrides are preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; ketones, such as acetone or methyl ethyl ketone; esters, such as ethyl acetate; nitriles, such as acetonitrile; amides, such as N,N-dimethylformamide, N,N-dimethylacetamide, N-methyl-2-pyrrolidone or hexamethylphosphoric triamide; and sulfoxides, such as dimethyl sulfoxide. Of these, the amides are preferred.

The reaction can take place over a wide range of temperatures, and the precise reaction temperature is not critical to the invention. In general, we find it convenient to carry out the reaction at a temperature of from −10° C. to 100° C. (more preferably from 0° C. to 50° C.), although this may vary, depending on the nature of the compound of formula (Ic) and the solvent. The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice.

The reaction of Step A2(2), which comprises the conversion of the nitro group represented by $R^{3a}$ in the compound of formula (Ic) into an amino group is preferably effected, in an inert solvent and in the presence of an acid, by reaction of a nitro compound of formula (Ic) in which $R^{3a}$ represents a nitro group with a reducing agent, for example a metal powder. Suitable reducing metal powders include powders of iron, tin or zinc. Of these, iron or tin powder is preferred.

Suitable acids include: mineral acids, such as hydrochloric acid or sulfuric acid; and organic acids, such as acetic acid, trifluoroacetic acid, methanesulfonic acid or p-toluensulfonic acid. Of these, hydrochloric acid or acetic acid is preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; ethers, such as diethyl ether, tetrahydrofuran or dioxane; alcohols, such as methanol or ethanol; the acid employed for the reaction, as mentioned above; or a mixture of any two or more of these solvents. Of these, we prefer to use a mixture of water with an acid.

The reaction can take place over a wide range of temperatures, and the precise reaction temperature is not critical to the invention. In general, we find it convenient to carry out the reaction at a temperature of from −10° C. to 100° C. (more preferably from 0° C. to 50° C.), although this may vary depending on the nature of the starting material of formula (Ic) and on the solvent employed. The time required for the reaction may also vary widely, depending on many factors, notably the reaction temperature and the nature of the reagents and solvent employed. However, provided that the reaction is effected under the preferred conditions outlined above, a period of from 15 minutes to 20 hours (more preferably from 30 minutes to 10 hours) will usually suffice. If this reaction is carried out in an organic acid and in the presence of one of the acid anhydrides mentioned later in connection with the reaction of Step A2(3), this reaction affords an amino-acylated compound.

Conversion of the nitro group into an amino group can be also conducted in a similar manner to Step C2(4) of Reaction Scheme C as described hereafter, and, in this case, any nitro group contained in $R^1$ is converted into an amino group at the same time.

Alkylation, aralkylation or acylation of the amino group can be conducted by reacting an amino compound of formula (Ic) in which $R^3$ represents an amino group with a corresponding alkyl halide, aralkyl halide, acyl halide or acid anhydride [for example: an alkyl halide having from 1 to 4 carbon atoms; an alkyl halide having from 1 to 4 carbon atoms which is substituted by an alkoxy group having from 1 to 4 carbon atoms, by an alkanoyloxy group having from 1 to 6 carbon atoms or by an arylcarbonyloxy group having from 6 to 10 carbon atoms in the aryl moiety; an aralkyl halide having from 7 to 14 carbon atoms; an alkanoyl halide having from 2 to 18 carbon atoms or a mixed acid anhydride of a corresponding acid with formic acid; an alkenoyl halide having from 3 to 6 carbon atoms; a cycloalkanecarbonyl halide having from 3 to 7 carbon atoms in the cycloalkane moiety; an arylcarbonyl halide having from 6 to 10 carbon atoms in the aryl moiety; an alkoxycarbonyl halide having from 1 to 4 carbon atoms in the alkoxy moiety; an alkyl carbonate anhydride having from 1 to 4 carbon atoms in the alkyl moiety; an aralkyloxycarbonyl halide having from 7 to 14 carbon atoms in the aralkyl moiety; a phthalidyl halide; or a (5-methyl- or 5-phenyl-2-oxo-1,3-dioxolen-4-yl)methyl halide, all as exemplified above in relation to Step A2(1)]. This reaction normally and preferably takes place in an inert solvent and in the presence of a base. If it is desired to prepare a mono-alkylamino compound having from 1 to 4 carbon atoms, we prefer to use about an equimolar amount of an alkyl halide having from 1 to 4 carbon atoms with respect to the compound of formula (I); on the other hand, the desired compound is a di-alkylamino compound having from 1 to 4 carbon atoms in each alkyl moiety, it is preferred to use more than about 2 moles of an alkyl halide having from 1 to 4 carbon atoms per mole of the compound of formula (I).

The reaction is essentially the same as that employed in Step A1, and may be carried out using the reaction conditions, base and solvent as described above in relation to that reaction.

After completion of the reaction or any of the reactions described above, the desired compound can be obtained from the reaction mixture by conventional means. For example, one suitable recovery procedure comprises: filtering off any insoluble matter; adding water to the filtrate; if necessary, neutralizing the resulting mixture; extracting it with a water-imiscible organic solvent, such as ethyl acetate; drying it; and distilling off the solvent. If necessary, the product thus obtained can be further purified by conventional means, such as recrystallization or the various chromatography techniques, for example preparative thin layer chromatography or column chromatography, notably column chromatography.

A salt of the compound of formula (I) can be prepared by conventional means, as is well known in the art. For example, the compound of formula (I) is treated with an acid, such as hydrochloric acid or maleic acid, in an inert solvent, such as diethyl ether or diisopropyl ether, and the separated crystals are recovered by filtration.

An optically active compound of formula (I) can be prepared by using a corresponding optically active benzyl halide of formula (II) as the starting material, or by optical resolution of a racemic compound of formula (I) by conventional means, such as fractional crystallization or liquid chromatography.

The condensed hydropyridyl compound of formula (IV), used as one of the starting materials, is known or may easily be prepared by any known method [for example, M. Podesta et al., Eur. J. Med. Chem.—Chim. Ther. 9 (5), 487–490 (1974); and Japanese Patent Kokai Application No. Sho 61-246186]. Compounds of formula (IV) having a nitro group as the group $R^{3a}$ are known or can be prepared as follows:

The imino group in a compound corresponding to the compound of formula (IV), but in which the group $R^{3a}$ is a hydrogen atom [which can easily be prepared by any known method (for example, as described in Japanese Patent Kokai Application No. Sho 62-103088)] is protected. The protecting reaction can be conducted in a similar way to that described in Step A2(3) of Reaction Scheme A, above. The protecting group may be, for example, an acyl group, such as an alkanoyl group having from 1 to 18 carbon atoms as exemplified above. The protected compound is then allowed to react in an inert solvent (which may be, for example, a fatty acid, such as acetic acid or propionic acid, or acid anhydride, such as acetic anhydride or propionic anhydride, or a mixture of any two or more thereof) with a nitrating agent (such as fuming nitric acid or anhydrous nitric acid) at a suitable temperature, for example from 0° C. to 50° C., for a period of, for example, from 15 minutes to 5 hours, and is finally treated with an acid (such as aqueous hydrochloric acid or aqueous sulfuric acid) at a suitable temperature, for example from 20° C. to 100° C., for a period of, for example, from 15 minutes to 5 hours to remove the protecting group.

The compound of formula (III), which is the other starting material, can easily be prepared, for example by the processes shown below in Reaction Schemes B, C, D and E.

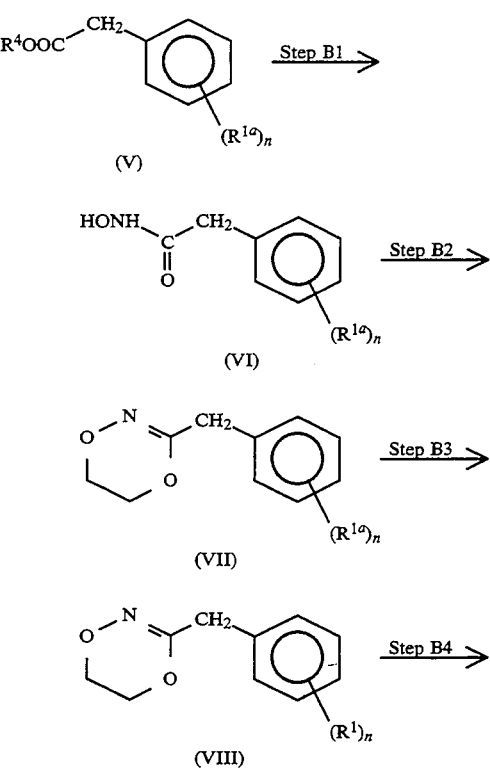

Reaction Scheme B:

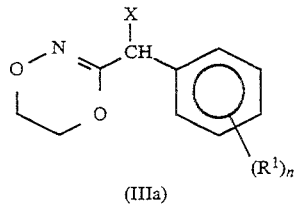

(IIIa)

Reaction Scheme C:

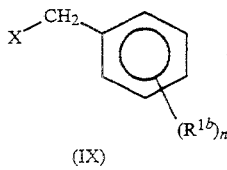

(IX)

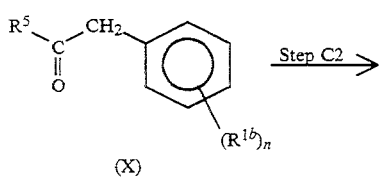

(X)

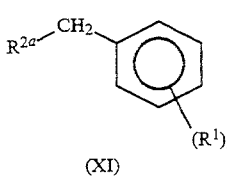

(XI)

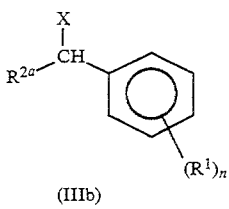

(IIIb)

Reaction Scheme D:

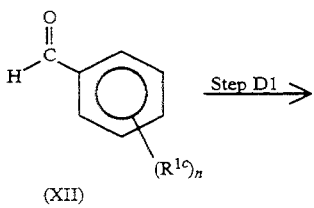

(XII)

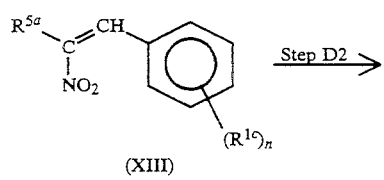

(XIII)

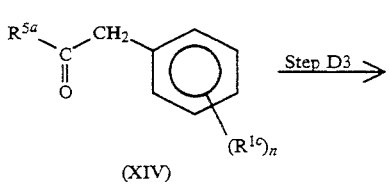

(XIV)

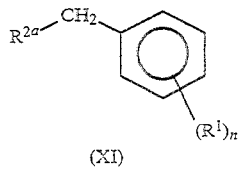

(XI)

Reaction Scheme E:

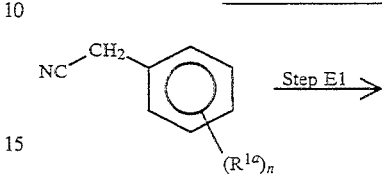

(XV)

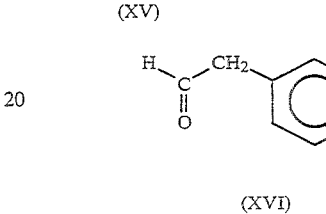

(XVI)

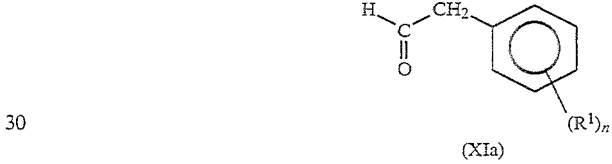

(XIa)

In these formulae, $R^1$, X and n are as defined above.

$R^{1a}$ represents a hydrogen atom, an alkyl group having from 1 to 4 carbon atoms, a halogen atom, a haloalkyl group having from 1 to 4 carbon atoms and at least one halogen atom, a hydroxy group, an alkoxy group having from 1 to 4 carbon atoms, a haloalkoxy group having from 1 to 4 carbon atoms and at least one halogen atom, an alkylthio group having from 1 to 4 carbon atoms, a haloalkylthio group having from 1 to 4 carbon atoms and at least one halogen atom, an amino group, a protected alkanoyl group having from 1 to 5 carbon atoms in the alkanoyl part, a protected haloalkanoyl group having from 2 to 5 carbon atoms and at least one halogen atom in the haloalkanoyl part, a carbamoyl group, a nitro group, an alkanesulfonyl group having from 1 to 4 carbon atoms, a haloalkanesulfonyl group having from 1 to 4 carbon atoms and at least one halogen atom, or a sulfamoyl group. That is, it represents the same groups as does $R^1$ other than the cyano carboxy and alkoxycarbonyl, and the alkanoyl groups and the haloalkanoyl groups are protected.

$R^{1b}$ represents a hydrogen atom, an alkyl group having from 1 to 4 carbon atoms, a halogen atom, a haloalkyl group having from 1 to 4 carbon atoms and at least one halogen atom, a protected hydroxy group, an alkoxy group having from 1 to 4 carbon atoms, a haloalkoxy group having from 1 to 4 carbon atoms and at least one halogen atom, an alkylthio group having from 1 to 4 carbon atoms, a haloalkylthio group having from 1 to 4 carbon atoms and at least one halogen atom, an protected alkanoyl group having from 1 to 5 carbon atoms in the alkanoyl part, a protected haloalkanoyl group having from 2 to 5 carbon atoms and at least one halogen atom in the haloalkanoyl part, a nitro group, an alkanesulfonyl group having from 1 to 4 carbon atoms, or a haloalkanesulfonyl group having from 1 to 4 carbon atoms and at least one halogen atom. That is, it represents the same groups as does $R^1$, other than the amino, cyano, carboxy, carbamoyl, sulfamoyl and alkoxycarbonyl groups, and the alkanoyl groups, the haloalkanoyl groups and the hydroxy groups are protected.

$R^{1c}$ represents the same groups as are defined above for $R^1$, except that the alkanoyl group having from 1 to 5 carbon atoms and the haloalkanoyl group having from 2 to 5 carbon atoms are protected.

$R^{2a}$ represents the same groups as are defined above for $R^2$, other than the dihydrodioxazinyl group.

$R^4$ represents an alkyl group having from 1 to 4 carbon atoms.

$R^5$ represents a hydrogen atom, an alkyl group having from 1 to 9 carbon atoms, a substituted alkyl group which has from 1 to 9 carbon atoms and which is substituted by at least one substituent selected from the group consisting of substituents A, defined above, an alkenyl group having from 2 to 5 carbon atoms, a substituted alkenyl group which has from 2 to 5 carbon atoms and which is substituted by at least one substituent selected from the group consisting of substituents A, defined above, a cycloalkyl group having from 3 to 7 carbon atoms, a substituted cycloalkyl group which has from 3 to 7 carbon atoms and which is substituted by at least one substituent selected from the group consisting of substituents A, defined above, or a substituted phenyl group having at least one substituent selected from the group consisting of substituents B, defined above, and provided that any hydroxy group in substituents A is protected. That is, it represents any of the groups (other than the dihydrodioxazinyl group) defined above for $R^2$, but without the terminal carbonyl group.

$R^{5a}$ represents any of the groups represented by $R^5$, except that the hydroxy group of substituent A need not be protected.

There is no particular limitation on the nature of the protecting group for the alkanoyl group having from 1 to 5 carbon atoms or the haloalkanoyl group having from 2 to 5 carbon atoms, and any such group commonly used for the protection of aldehydes and ketones in the field of organic chemistry. Examples include an acetal or ketal containing a carbonyl moiety as shown in the following formula:

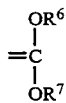 (XVII)

in which $R^6$ and $R^7$ are the same or different and each represents an alkyl group having from 1 to 4 carbon atoms (such as a methyl, ethyl, propyl, isopropyl or butyl group) or $R^6$ and $R^7$ together form an alkylene group having 2 or 3 carbon atoms (such as an ethylene or trimethylene group). We prefer an acetal or ketal in which $R^6$ and $R^7$ are each a methyl or ethyl group, or $R^6$ and $R^7$ together form an ethylene or trimethylene group.

The nature of the hydroxy-protecting groups which may be employed in this reaction is not critical and any hydroxy-protecting group known for use in this type of reaction may equally be employed here. Examples of such groups include groups derived from the cyclic ethers, such as the tetrahydropyranyl or tetrahydrofuranyl group.

In Reaction Scheme B, a compound of formula (IIIa) is prepared; this is a compound of formula (III) in which $R^2$ is a dihydrodioxazinyl group.

In Step B1 of this Reaction Scheme, a compound of formula (VI) is prepared by reacting a compound of formula (V) with hydroxylamine or with a mineral acid salt of hydroxylamine (such as the hydrochloride or the sulfate) in an inert solvent (for example, an alcohol such as methanol or ethanol) and in the presence of a base (for example, an alkali metal alkoxide such as sodium methoxide, sodium ethoxide or potassium t-butoxide) at a suitable temperature, preferably from 0° C. to 150° C. (more preferably from about room temperature to 100° C.) for a suitable period, preferably from 1 to 24 hours (more preferably from 2 to 15 hours).

In Step B2 of this Reaction Scheme, a compound of formula (VII) is prepared by reacting a compound of formula (VI) with a compound of formula (XVIII):

 (XVIII)

in which $X^a$ and $X^b$ are the same or different and each represents a halogen atom. The reaction is normally and preferably effected in the presence of a solvent. There is no particular restriction on the nature of the solvent to be employed, provided that it has no adverse effect on the reaction or on the reagents involved, and that it can dissolve the reagents, at least to some extent. Examples of suitable solvents include: water, and alcohols, such as methanol or ethanol. The reaction is also preferably effected in the presence of a base, the nature of which is also not critical to the present invention. Examples of such bases include: alkali metal carbonates, such as sodium carbonate or potassium carbonate; and alkali metal hydroxides, such as sodium hydroxide or potassium hydroxide. The reaction can take place over a wide range of temperatures, and the precise reaction temperature is not critical to the present invention. In general, we find it convenient to carry out the reaction at a temperature of from 0° C. to 200° C. (more preferably at a temperature from about room temperature to 150° C.). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 2 to 15 hours) will usually suffice.

Step B3 of this Reaction Scheme is optional to give a compound of formula (VIII), and may consist of one or more of the following reactions:

(1) Removal of the alkanoyl- or haloalkanoyl-protecting group contained in $R^{1a}$;

(2) Conversion of the halogen atom contained in $R^{1a}$ into a cyano group;

(b 3) Conversion of the halogen atom contained in $R^{1a}$ into a carboxy group, followed, if desired, by conversion of the carboxy group into an alkoxycarbonyl group having from 1 to 4 carbon atoms in the alkoxy moiety.

In Step B3(1) of this Reaction Scheme, removal of the alkanoyl- or haloalkanoyl-protecting group can be effected by conventional means commonly employed in the field of organic chemistry. For example, if the protecting group is an acetal or a ketal, a corresponding compound of formula (VII) is reacted with an acid (for example, a mineral acid, such as hydrochloric acid, sulfuric acid or nitric acid; or an organic acid, such as acetic acid, trifluoroacetic acid, methanesulfonic acid or p-toluenesulfonic acid). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water and alcohols, such as methanol or ethanol. The reaction can take place over a wide range of temperatures, and the precise reaction temperature is not critical to the invention. In general, we find it convenient to carry out the reaction at a temperature of from 0° C. to 100° C. (more preferably at a temperature from about room temperature to 50° C.). The time required for the reaction may also vary widely, depending on many factors, notably the reaction temperature and the nature of the reagents and solvent employed. However, provided that the reaction is effected under the preferred conditions outlined above, a period of from 10 minutes to 5 hours (more preferably from 30 minutes to 2 hours) will usually suffice.

Conversion of a halogen atom into a cyano group in Step B3(2) of this Reaction Scheme is preferably effected by reacting the corresponding compound of formula (VII) with a metal cyanide, such as sodium cyanide, potassium cyanide or copper cyanide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide or dimethylacetamide; and ethers, such as diethyl ether or tetrahydrofuran. The reaction can take place over a wide range of temperatures, and the precise reaction temperature is not critical to the invention. In general, we find it convenient to carry out the reaction at a temperature of from 0° C. to 200° C. (more preferably at a temperature from about room temperature to 150° C.). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 2 to 15 hours) will usually suffice.

Conversion of the halogen atom into a carboxy group in Step B3(3) of this Reaction Scheme is preferably effected by reacting the corresponding compound of formula (VII) with magnesium. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether or tetrahydrofuran. The reaction can take place over a wide range of temperatures, and the precise reaction temperature is not critical to the invention. In general, we find it convenient to carry out the reaction at a temperature of from 0° C. to 150° C. (more preferably at a temperature from about room temperature to 100° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice. The resulting Grignard reagent is then reacted with carbon dioxide gas at a temperature from, for example, 0° C. to 150° C. (more preferably at a temperature from about room temperature to 100° C.) for a suitable period, for example from 30 minutes to 24 hours (more preferably from 1 to 10 hours).

Conversion of the resulting carboxy group into an alkoxycarbonyl group having from 1 to 4 carbon atoms can, if desired, be conducted by reacting the corresponding carboxylic acid with an alcohol having from 1 to 4 carbon atoms, such as methanol, ethanol, propanol, isopropanol or butanol, in the presence of an acid (for example, a mineral acid, such as hydrochloric acid, sulfuric acid or nitric acid; or an organic acid, such as acetic acid, trifluoroacetic acid, methanesulfonic acid or p-toluensulfonic acid). The reaction can take place over a wide range of temperatures, and the precise reaction temperature is not critical to the invention. In general, we find it convenient to carry out the reaction at a temperature of from 0° C. to 100° C. (more preferably at a temperature from about room temperature to 50° C.). The time required for the reaction may also vary widely, depending on many factors, notably the reaction temperature and the nature of the reagents and solvent employed. However, provided that the reaction is effected under the preferred conditions outlined above, a period of from 30 minutes to 5 hours (preferably from 1 to 2 hours) will usually suffice. Rather than using any additional solvent, this reaction is usually carried out by using as the solvent a large excess of the alcohol having from 1 to 4 carbon atoms, which is one of the reagents.

In Step B4, a compound of formula (IIIa) is prepared by reacting a compound of formula (VIII) with a haloimide, such as N-chlorosuccimide, N-bromosuccimide or N-iodosuccimide in the presence of a radical initiator, such as benzoyl peroxide, or by reacting said compound of formula (VIII) with a halogen, such as chlorine, bromine or iodine, in an inert solvent (for example, a halogenated hydrocarbon, preferably a halogenated aliphatic hydrocarbon, such as methylene chloride, chloroform or carbon tetrachloride). The reaction can take place over a wide range of temperatures, and the precise reaction temperature is not critical to the invention. In general, we find it convenient to carry out the reaction at a temperature of from 0° C. to 100° C. (more preferably at a temperature from about room temperature to 50° C.). The time required for the reaction may also vary widely, depending on many factors, notably the reaction temperature and the nature of the reagents and solvent employed. However, provided that the reaction is effected under the preferred conditions outlined above, a period of from 30 minutes to 20 hours (more preferably from 1 to 15 hours) will usually suffice.

In Reaction Scheme C, a compound of formula (IIIb) is prepared. This is a compound of formula (III) in which $R^2$ is replaced by $R^{2a}$, that is any of the groups defined above for $R^2$ except a dihydrodioxazinyl group.

In Step C1 of this Reaction Scheme, a compound of formula (X) is prepared by reacting a compound of formula (IX) with magnesium in an inert solvent (for example, an ether, such as diethyl ether or tetrahydrofuran), to give a Grignard reagent. The reaction can take place over a wide range of temperatures, and the precise reaction temperature is not critical to the invention. In general, we find it convenient to carry out the reaction at a temperature of from 0° C. to 150° C. (more preferably at a temperature from about room temperature to 100° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice. The resulting Grignard reagent is then reacted with a compound of formula (XIX), (XX) or (XXI):

$R^{5b}$—CN    (XIX)

$R^{5c}$—COX    (XX)

or

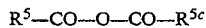

$R^5$—CO—O—CO—$R^{5c}$    (XXI)

in which $R^5$ and X are as defined above; $R^{5b}$ represents any of the groups defined for $R^5$ except a group having a cyano substituent; and $R^{5c}$ represents any of the groups defined for $R^5$ except a hydrogen atom. The reaction can take place over a wide range of temperatures, and the precise reaction temperature is not critical to the invention. In general, we find it convenient to carry out the reaction at a temperature of from 0° C. to 150° C. (more preferably at a temperature from about room temperature to 100° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice.

Step C2 of Reaction Scheme C comprises one or more of the following optional reactions:

(1) Removal of the alkanoyl- or haloalkanoyl-protecting group contained in $R^{1b}$;

(2) Removal of the hydroxy-protecting group contained in $R^{1b}$, $R^5$ etc;

(3) Conversion of the halogen atom contained in $R^{1b}$ into a cyano group, and then optionally into a carbamoyl group, and then optionally into a carboxy, and finally optionally into an alkoxycarbonyl group having from 1 to 4 carbon atoms in the alkoxy moiety;

(4) Conversion of the nitro group contained in $R^{1b}$ into an amino group; and (5) Conversion of the alkylthio group contained in $R^{1b}$ into a sulfamoyl group.

Removal of the alkanoyl- or haloalkanoyl-protecting group in Step C2(1) and removal of the hydroxy-protecting cyclic ether group in Step C2(2) can be conducted in a similar way to that in Step B3(1) of Reaction Scheme B, as described above.

Conversion of the halogen atom into a cyano group in Step C2(3) can be conducted in a similar way to that in Step B3(2) of Reaction Scheme B, as described above. In this reaction, it is preferred not to use as the starting material a compound of formula (X) containing a halogen atom in the substituent of $R^5$. If a compound containing a halogen atom in the substituent $R^5$ is used, conversion of this halogen atom into a cyano group is also possible.

Successive conversion of the cyano group into carbamoyl and carboxy groups can be conducted by reaction of a corresponding compound of formula (X) with an aqueous mineral acid (such as aqueous sulfuric acid, aqueous hydrochloric acid or aqueous nitric acid). The reaction can take place over a wide range of temperatures, and the precise reaction temperature is not critical to the invention. In general, we find it convenient to carry out the reaction at a temperature of from 0° C. to 200° C. (more preferably at a temperature from about room temperature to 100° C.). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 2 to 15 hours) will usually suffice. In this reaction, it is possible to choose whether the carbamoyl or the carboxy compound will be obtained by adjusting the acid concentration. For example, the carbamoyl compound can be obtained by reaction in about 90% sulfuric acid, and then it can be converted into the carboxy compound by reaction in about 60% sulfuric acid.

Conversion of the carboxy group into an alkoxycarbonyl group having from 1 to 4 carbon atoms in the alkoxy moiety can be conducted in a similar way to that described in Step B3(3) of Reaction Scheme B, as described above.

Conversion of the nitro group into an amino group in Step C2(4) can be conducted by reacting the corresponding compound of formula (X) with hydrogen gas (preferably at from 1 atmosphere to 5 atmospheres) in an inert solvent (for example, an alcohol, such as methanol or ethanol) and in the presence of a reducing catalyst (such as Raney-nickel, palladium-on-carbon or platinum oxide). The reaction can take place over a wide range of temperatures, and the precise reaction temperature is not critical to the invention. In general, we find it convenient to carry out the reaction at a temperature of from 0° C. to 150° C. (preferably at room temperature to 100° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice.

Conversion of the alkylthio group into a sulfamoyl group in Step C2(5) can be conducted by reacting a corresponding compound of formula (X) with a halogenating agent (such as chlorine or bromine) in an inert solvent (for example, water, an organic acid, such as acetic acid or propionic acid or a mixture of any two or more thereof), to give a sulfonyl halide. The reaction can take place over a wide range of temperatures, and the precise reaction temperature is not critical to the invention. In general, we find it convenient to carry out the reaction at a temperature of from −10° C. to 100° C. (more preferably at from −5° C. to 50° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice. The resulting sulfonyl halide is then reacted with ammonia in an inert solvent (for example, water or an alcohol, such as methanol or ethanol) at, for example, from 0° C. to 100° C. (more preferably at room temperature to 50° C.) for a suitable period, for example from 30 minutes to 24 hours (more preferably from 1 to 10 hours).

In Step C3 of Reaction Scheme C, a compound of formula (IIIb) is prepared by halogenation of the compound of formula (XI) prepared in Step C2. This reaction is essentially the same as that described in Step B4 of Reaction Scheme B, and may be carried out using the same reagents and reaction conditions.

Reaction Scheme D provides an alternative route for preparing the compound of formula (XI), which is also prepared in Step C2 of Reaction Scheme C.

In Step D1 of Reaction Scheme D, a compound of formula (XIII) is prepared by reacting a compound of formula (XII) with a compound of formula (XXII):

$$O_2N-CH_2-R^{5a} \qquad (XXII)$$

in which $R^{5a}$ is as defined above. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include organic acids, such as acetic acid or propionic acid. The reaction is also normally and preferably effected and in the presence of a base, for example, an ammonium salt of an organic acid, such as ammonium acetate, ammonium propionate or ammonium benzoate. The reaction can take place over a wide range of temperatures, and the precise reaction temperature is not critical to the invention. In general, we find it convenient to carry out the reaction at a temperature of from about room temperature to 200° C. (more preferably at from 50° C. to 150° C.). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 2 to 15 hours) will usually suffice.

In Step D2 of Reaction Scheme D, a compound of formula (XIV) is prepared by reacting a compound of formula (XIII) with a reducing agent (such as zinc or iron) in an inert solvent (for example, an organic acid, such as acetic acid or propionic acid) and in the presence of water. The reaction can take place over a wide range of temperatures, and the precise reaction temperature is not critical to the invention. In general, we find it convenient to carry out the reaction at a temperature of from about room temperature to 250° C. (more preferably at from 50° C. to 150° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 10 hours) will usually suffice.

Step D3 of this Reaction Scheme is optional and comprises removal of the alkanoyl- or haloalkanoyl-protecting group contained in $R^{1c}$. The removal reaction is essentially the same reaction as that employed in Step B3 of Reaction Scheme B, and may be carried out employing the same reagents and reaction conditions.

Reaction Scheme E provides an alternative route for preparing a compound of formula (XI), which is also prepared in Step C2 of Reaction Scheme C, when $R^{2a}$ in the compound of formula (XI) is a formyl group, that is a compound of formula (XIa).

In Step E1 of Reaction Scheme E, a compound of formula (XVI) is prepared by reacting a compound of formula (XV) with a reducing agent [for example, an aluminum hydride, such as lithium tri(t-butoxy)aluminum hydride or lithium aluminum hydride]. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether or tetrahydrofuran. The reaction can take place over a wide range of temperatures, and the precise reaction temperature is not critical to the invention. In general, we find it convenient to carry out the reaction at a temperature of from −30° C. to 50° C. (more preferably at from 0° C. to room temperature). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 2 to 15 hours) will usually suffice.

Step E2 of Reaction Scheme E is optional and comprises one or more of the following reactions:
(1) Removal of the alkanoyl- or haloalkanoyl-protecting group contained in $R^{1a}$;
(2) Conversion of the halogen atom contained in $R^{1a}$ into a cyano group, which may then, if desired, be converted into a carboxy group, which finally may, if desired, be converted into an alkoxycarbonyl group.

These reactions are essentially the same as those described above in relation to Step C2 of Reaction Scheme C, and may be carried out employing the same reagents and reaction conditions.

After completion of any of these reactions, the desired compound can be recovered from the reaction mixture by conventional means. For example, insoluble matter, if any, is filtered off, and, if the reaction solution is acidic or alkaline, the solution is neutralized. The desired product can then be recovered by distilling off the solvent, or by adding water, extracting the resulting mixture with a water-immiscible organic solvent, such as ethyl acetate, drying the extract, and then distilling off the solvent. If necessary, the product thus obtained can be further purified by conventional means, such as recrystallization or the various chromatography techniques, for example preparative thin layer chromatography or column chromatography, notably column chromatography.

Alternatively, when the desired compound is a carboxylic acid derivative, it may be recovered from the reaction medium by the following procedure: making the reaction solution alkaline; extracting the resulting mixture with a water-immiscible organic solvent, such as ethyl acetate; neutralizing the aqueous layer; extracting the desired compound with a water-immiscible organic solvent, such as ethyl acetate; drying the extract; and then distilling off the solvent.

The compounds of the present invention prepared as described above may be converted to acid addition salts and/or to complexes with metal ions by methods well known in the art.

BIOLOGICAL ACTIVITY

The compounds of formula (I) and their tautomers, salts and complexes of the present invention have an excellent inhibitory activity against blood platelet aggregation, and are therefore very useful for prevention and therapy of thrombosis and embolism. These activities are demonstrated by the following Test Examples, which employ techniques well recognised in the art to provide a model of such activity in humans and other mammals.

Test Example 1

Prolongation of Bleeding Time in Mice

Male mice of the ICR strain (supplied by Japan Charles River Inc.) were divided into groups of 10 each for the test. A sample of the drug to be tested was suspended in a 5% w/v aqueous solution of gum arabic, and administered orally to the mice at a dose of 3 mg/kg for 3 successive days, namely 48 hours, 24 hours and 4 hours before the bleeding test. For the test, each of the mice was fixed by use of conventional apparatus, and the tail was cut 5 mm from the end. The last 2 cm of the tail was soaked in physiological saline kept warm at 37° C. The time at which bleeding was observed to cease for a successive 15 seconds was regarded as the point at which bleeding stopped, and the time between cutting the tail until the point when bleeding stopped was recorded as the bleeding time. The bleeding time was observed for a maximum of 5 minutes, and, even if bleeding continued for longer than 5 minutes, the bleeding time was reported as 5 minutes (300 seconds). The results are shown in Table 2. The test was carried out using certain of the compounds of the present invention, as well as with two prior art compounds.

Each of the compounds of the present invention is identified in the Table by the number assigned to it in the foregoing Table 1 and by the number of the Example hereafter which illustrates its preparation. The prior art compounds are identified as follows:

Compound A: 5-(2-chlorobenzyl)-4,5,6,7-tetrahydrothieno[3,2-c]pyridine;
Compound B: 5-(2-chloro-α-methoxycarbonylbenzyl)-4,5,6,7-tetrahydrothieno[3,2-c]pyridine.

Test Example 2

Inhibition of Blood Platelet Aggregation

Female rats of the SD strain (supplied by Japan Charles River Inc.) were divided into groups of 4 each for the test. A sample of the drug to be tested was suspended in a 5% w/v aqueous solution of gum arabic, and administered orally to the rats 4 hours before the test. As a control, a 5% w/v aqueous solution of gum arabic was administered to a control group of rats, without any test drug. Blood platelet aggregation was tested according to the method of P. Lumley and P. P. A. Humphrey [J. Pharmacol. Methods 6, 153–166 (1981)] with a partial modification. From the abdominal aorta of the anesthetized rat, 5.4 ml of a blood sample was taken in 0.6 ml of a 3.8% (w/v) sodium citrate solution serving as an anticoagulant. The resulting citrate-containing blood samples were poured into cuvettes, with 1.2 ml in each cuvette, and stirred (1000 rpm) at 37° C. After preliminary heating for 2 minutes, 0.3 ml of the blood sample was taken out of each of the cuvettes, and the blood platelet count was measured by means of an automatic blood cell counter (E-4000, Sysmex); this was regarded as the blood platelet count before addition. 0.9 ml of the blood sample in the cuvette was then mixed with 0.1 ml of a 0.05M adenosine diphosphate (ADP) solution or with 0.1 ml of a collagen suspension (0.06 mg/ml), to induce blood platelet aggregation. Two minutes after addition of the ADP, or 4 minutes after addition of the collagen, 0.3 ml of the blood sample was taken and the blood platelet count was measured; this was regarded as the blood platelet count after addition. The blood platelet aggregation rate was calculated from the following equation.

100×(blood platelet count before addition−blood platelet count after addition)/blood platelet count before addition The inhibitory effect was calculated as the percent inhibition of the treated groups as compared with the control groups. The results are reported in Table 2.

TABLE 2

| Ex. No. | Cpd. No. | Test Ex. 1 Bleeding time (hours), 3 mg/kg | Test Ex. 2 % Inhibition | | |
|---|---|---|---|---|---|
| | | | 1 mg/kg | 3 mg/kg | 10 mg/kg |
| 5 | 60 | 2.20 | — | 74.2 | 100 |
| 6 | 19 | 2.13 | — | 29.3 | 97.8 |
| 12 | 59 | >2.75 | 57.1 | 98.1 | — |
| 20 | 235 | >2.75 | 98.8 | — | — |
| 22 | 233 | 2.30 | — | — | 98.9 |
| 23 | 190 | >2.75 | 100 | — | — |
| 25 | 194 | >2.75 | 100 | — | — |
| 26 | 196 | >2.75 | 97.6 | — | — |
| Compound A | | 1.00 | — | — | 3.7* |
| Compound B | | 1.80 | — | 25.7 | 98.8 |

*at a dose of 30 mg/kg.

For therapeutic or prophylactic use, the compounds of the present invention may be administered by themselves or in admixture with any one or more conventional carriers, diluents or additives. Administration may be by any convenient route, for example orally or parenterally, and the formulation will be chosen having regard to the intended route of administration. The compounds may, for example, be administered in the form of powders, granules, tablets, capsules and injections. The dosage may vary depending upon the severity and nature of the disorder, as well as the symptoms, age and body weight of the patient and the chosen route of administration; however, in the case of oral administration, we would normally suggest a dose of from 1 to 1000 mg, more preferably from 10 to 500 mg, if administered orally, or a dose of from 0.5 to 500 mg, more preferably from 5 to 250 mg, if administered intravenously. The compound may be administered in single or divided doses, e.g. from 1 to 3 times a day depending on the symptoms.

The preparation of the compounds of the present invention is further illustrated by the following non-limiting Examples, whilst the preparation of certain of the starting materials used in these Examples is illustrated by the subsequent Preparations.

EXAMPLE 1

5-(2-Chloro-α-trifluoroacetylbenzyl)-4,5,6,7-tetrahydrothieno[3,2-c]pyridine (Compound No. 113)

10 ml of methylene chloride were added to 0.39 g (2.6 mmole) of 4,5,6,7-tetrahydrothieno[3,2-c]pyridine hydrochloride and 0.28 g (2.6 mmole) of sodium carbonate, and then a solution of 0.67 g (2.2 mmole) of 2-chloro-α-trifluoroacetylbenzyl bromide in 10 ml of methylene chloride was slowly added to the resulting mixture, whilst stirring at room temperature. The mixture was then stirred at room temperature for 3 hours. At the end of this time, 200 ml of ethyl acetate were added to the reaction mixture, and the organic layer was separated, washed with a saturated aqueous solution of sodium chloride and dried over anhydrous magnesium sulfate. The solvent was removed by distillation under reduced pressure, and the resulting residue was subjected to silica gel column chromatography, using a 100:4 by volume mixture of toluene and ethyl acetate as the eluent, to give 0.31 g of the title compound as a colorless oil.

Infrared Absorption Spectrum (thin film) $\nu_{max}$ cm$^{-1}$: 1685, 1705.

Nuclear Magnetic Resonance Spectrum (CDCl$_3$) δ ppm: 2.90–3.04 (2H, multiplier); 3.90 (1H, triplet, J=6.0 Hz); 4.01 (1H, triplet, J=6.0 Hz); 5.51 (1H, doublet, J=7.3 Hz); 5.58 (1H, doublet, J=7.3 Hz); 6.82 (1H, doublet, J=5.4 Hz); 7.19 (2H, doublet, J=5.4 Hz); 7.36–7.58 (4H, multiplet).

Mass spectrum (CI, m/z): 360 (M$^+$ +1).

Here and hereafter, in the mass spectra, "CI" means "chemical ionization".

EXAMPLE 2

5-[2-Chloro-α-(5,6-dihydro-1,4,2-dioxazin-3-yl)benzyl]-4,5,6,7-tetrahydrothieno[3,2-c]pyridine and its hydrochloride (Compound No. 3)

2(a) Following a procedure similar to that described in Example 1, except that an equivalent amount of 2-chloro-α-(5,6-dihydro-1,4,2-dioxazin-3-yl)benzyl bromide (prepared as described in Preparation 18) was used in place of the 2-chloro-α-trifluoroacetylbenzyl bromide, the title compound was obtained as a colorless oil in a yield of 77%.

Nuclear Magnetic Resonance Spectrum (CDCl$_3$) δ ppm: 2.77–2.94 (4H, multiplet); 3.63 (1H, doublet, J=14.4 Hz); 3.79 (1H, doublet, J=14.4 Hz); 3.96–4.02 (1H, multiplet); 4.08–4.14 (1H, multiplet); 4.27–4.32 (1H, multiplet); 4.36–4.42 (1H, multiplet); 4.75 (1H, singlet); 6.70 (1H, doublet, J=5.4 Hz); 7.07 (1H, doublet, J=5.4 Hz); 7.20–7.90 (4H, multiplet).

Mass spectrum (CI, m/z): 349 (M$^+$ +1).

2(b) 2.7 g of the title compound obtained as described in step (a) above were dissolved in 100 ml of diethyl ether, and hydrogen chloride gas was blown into the resulting solution at room temperature. The crystals which precipitated were collected to obtain 2.3 g of the hydrochloride of the title compound as a colorless powder, melting at 104°–107° C.

Elemental analysis: Calculated for C$_{17}$H$_{17}$ClN$_2$O$_2$S.HCl.3/2H$_2$O: C, 49.52%; H, 5.13%; N, 6.80%. Found: C, 49.81%; H, 4.73%; N, 6.56%.

EXAMPLE 3

5-[2-Fluoro-α-(5,6-dihydro-1,4,2-dioxazin-3-yl)benzyl]-4,5,6,7-tetrahydrothieno[3,2-c]pyridine and its hydrochloride (Compound No. 2)

3(a) Following a procedure similar to that described in Example 1, except that an equivalent amount of 2-fluoro-α-(5,6-dihydro-1,4,2-dioxazin-3-yl)benzyl bromide (prepared as described in Preparation 19) was used in place of the 2-chloro-α-trifluoroacetylbenzyl bromide, the title compound was obtained as a colorless oil in a yield of 50%.

Nuclear Magnetic Resonance Spectrum (CDCl$_3$) δ ppm: 2.73–2.98 (4H, multiplet); 3.63 (1H, doublet, J=13.8 Hz); 3.79 (1H, doublet, J=13.8 Hz); 3.95–4.18 (2H, multiplet); 4.23–4.45 (2H, multiplet); 4.61 (1H, singlet); 6.70 (1H, doublet, J=5.4 Hz); 7.09 (1H, doublet, J=5.4 Hz); 7.20–7.80 (4H, multiplet).

Mass spectrum (CI, m/z): 333 (M$^+$ +1).

3(b) The procedure described in Example 2(b) was repeated, using the title compound as prepared in step (a) above, to obtain the hydrochloride of the title compound as a colorless powder, melting at 108°–112° C., in a yield of 81%.

Elemental analysis: Calculated for C$_{17}$H$_{17}$FN$_2$O$_2$S.HCl.H$_2$O: C, 52.78%; H, 5.21%; N, 7.24%. Found: C, 53.19%; H, 4.99%; N, 7.16%.

EXAMPLE 4

5-[2,6-Difluoro-α-(5,6-dihydro-1,4,2-dioxazin-3-yl)benzyl]-4,5,6,7-tetrahydrothieno[3,2-c]pyridine (Compound No. 7)

Following a procedure similar to that described in Example 1, except that an equivalent amount of 2,6-difluoro-α-(5,6-dihydro-1,4,2-dioxazin-3-yl)benzyl bromide (prepared as described in Preparation 20) was used in place of the 2-chloro-α-trifluoroacetylbenzyl bromide, the title compound was obtained as a colorless powder, melting at 151°–153° C., in a yield of 8%.

Nuclear Magnetic Resonance Spectrum (CDCl$_3$) δ ppm: 2.81–2.93 (4H, multiplet); 3.62 (1H, doublet, J=14.0 Hz); 3.79 (1H, doublet, J=14.0 Hz); 4.00–4.10 (2H, multiplet); 4.26–4.36 (2H, multiplet); 4.59 (1H, singlet); 6.70 (1H, doublet, J=5.4 Hz); 7.08 (1H, doublet, J=5.4 Hz); 7.20–7.80 (4H, multiplet).

Mass spectrum (CI, m/z): 351 (M$^+$ +1).

Elemental analysis: Calculated for C$_{17}$H$_{16}$F$_2$N$_2$O$_2$S: C, 58.27%; H, 4.60%; N, 8.00%. Found: C, 58.22%; H, 4.61%; N, 7.79%.

EXAMPLE 5

5-(2-Chloro-α-cyclopropylcarbonylbenzyl)-4,5,6,7-tetrahydrothieno[3,2-c]pyridine and its sulfate (Compound No. 60)

5(a) Following a procedure similar to that described in Example 1, except that an equivalent amount of 2-chloro-α-cyclopropylcarbonylbenzyl bromide was used in place of the 2-chloro-α-trifluoroacetylbenzyl bromide, the title compound was obtained as a yellow oil in yield of 66%.

Nuclear Magnetic Resonance Spectrum (CDCl$_3$) δ ppm: 0.78–0.90 (2H, multiplet); 0.96–1.06 (2H, multiplet); 2.15–2.29 (1H, multiplet); 2.83–2.94 (4H, multiplet); 3.56 (1H, doublet, J=4.3 Hz); 3.72 (1H, doublet, J=4.3 Hz); 5.06 (1H, singlet); 6.68 (1H, doublet, J=4.9 Hz); 7.06 (1H, doublet, J=4.9 Hz); 7.10–7.70 (4H, multiplet).

Mass spectrum (CI, m/z): 332 (M$^+$ +1), 262.

5(b) A procedure similar to that described in Example 2(b) was repeated, using the title compound as prepared in step (a) above, except that concentrated sulfuric acid was added in place of blowing hydrogen chloride gas through the mixture, to obtain the sulfate of the title compound as white crystals, melting at 184°–186° C., in a yield of 70%.

Elemental analysis: Calculated for C$_{18}$H$_{18}$ClNOS.H$_2$SO$_4$: C, 50.28%; H, 4.69%; N, 3.26%. Found: C, 50.43%; H, 4.53%; N, 2.87%.

EXAMPLE 6

5-(2-Fluoro-α-propionylbenzyl)-4,5,6,7-tetrahydrothieno[3,2-c]pyridine and its maleate (Compound No. 19)

6(a) 1.85 g (11.13 mmole) of 1-(2-fluorophenyl)-2-butatone (prepared as described in Preparation 9) were dissolved in 30 ml of carbon tetrachloride, and then a solution of 1.78 g of bromine in 15 ml of carbon tetrachloride was added dropwise to the resulting solution at room temperature over a period of 30 minutes. The resulting mixture was then stirred at room temperature for 5 hours, after which water was added to the reaction mixture. The reaction mixture was then extracted with chloroform, and the extract was dried over anhydrous magnesium sulfate. A crude 2-fluoro-α-propionylbenzyl bromide was obtained from this extract by removal of the solvent by evaporation under reduced pressure. 1.95 g (11.13 mmole) of 4,5,6,7-tetrahydrothieno[3,2-c]pyridine hydrochloride, 3.38 g (24.45 mmole) of anhydrous potassium carbonate and 30 ml of dimethylformamide were added to the crude product thus obtained, and the resulting mixture was stirred at room temperature for 5 hours. At the end of this time, toluene was added to the reaction mixture, and after the insolubles had been removed by filtration, the filtrate was concentrated by evaporation under reduced pressure. The resulting residue was subjected to silica gel column chromatography, using a 19:1 by volume mixture of toluene and ethyl acetate as the eluent, to give 1.17 g of the title compound as a pale yellow oil.

Infrared Absorption Spectrum (thin film) $v_{max}$ cm$^{-1}$: 1715.

Nuclear Magnetic Resonance Spectrum (CDCl$_3$) δ ppm: 1.03 (3H, triplet, J=7.0 Hz); 2.50 (2H, quartet, J=7.0 Hz); 2.80–2.95 (4H, multiplet); 3.53 (1H, doublet, J=11.0 Hz); 3.63 (1H, doublet, J=11.0 Hz); 4.75 (1H, singlet); 6.67 (1H, doublet, J=5.7 Hz); 7.05 (1H, doublet, J=5.7 Hz); 7.10–7.55 (4H, multiplet).

Mass spectrum (CI, m/z): 304 (M$^+$+1), 246.

6(b) A procedure similar to that described in Example 2(b) was repeated, using the title compound prepared as described in step (a) above, except that maleic acid was added in place of blowing hydrogen chloride gas through the reaction mixture, to obtain the maleate of the title compound as a colorless powder, melting at 101°–103° C., in a yield of 54%.

Elemental analysis: Calculated for C$_{17}$H$_{18}$FNOS.C$_4$H$_4$O$_4$.½H$_2$O: C, 58.86%; H, 5.41%; N, 3.27%. Found: C, 59.19%; H, 5.33%; N, 3.19%.

EXAMPLE 7

5-(α-Acetyl-2-chlorobenzyl)-4,5,6,7-tetrahydrothieno[3,2-c]pyridine and its hydrochloride (Compound No. 10)

7(a) Following a procedure similar to that described in Example 6, except that an equivalent amount of 1-(2-chlorophenyl)-2-propanone (prepared as described in Preparation 10) was used in place of the 1-(2-fluorophenyl)-2-butanone, the title compound was obtained as a pale yellow oil in a yield of 44%.

Infrared Absorption Spectrum (thin film) $v_{max}$ cm$^{-1}$: 1715.

Nuclear Magnetic Resonance Spectrum (CDCl$_3$) δ ppm: 2.13 (3H, singlet); 2.70–2.95 (4H, multiplet); 3.50 (1H, doublet, J=10.0 Hz); 3.70 (1H, doublet, J=10.0 Hz); 4.93 (1H, singlet); 6.65 (1H, doublet, J=5.7 Hz); 7.05 (1H, doublet, J=5.7 Hz); 7.10–7.75 (4H, multiplet).

Mass spectrum (CI, m/z): 306 (M$^+$+1), 262.

7(b) A procedure similar to that described in Example 2(b) was repeated, using the title compound prepared as described in step (a) above, to obtain the hydrochloride of the title compound as a pale yellow powder, melting at 98°–101° C., in a yield of 70%.

Elemental analysis: Calculated for C$_{16}$H$_{16}$ClNOS.HCl.½H$_2$O: C, 54.70%; H, 5.16%; N, 3.98%. Found: C, 55.09%; H, 4.97%; N, 3.80%.

EXAMPLE 8

5-(2-Chloro-α-propionylbenzyl)-4,5,6,7-tetrahydrothieno[3,2-c]pyridine and its hydrochloride (Compound No. 20).

8(a) Following a procedure similar to that described in Example 6, except that an equivalent amount of 1-(2-chlorophenyl)-2-butanone (prepared as described in Preparation 11) was used in place of the 1-(2-fluorophenyl)-2-butanone, the title compound was obtained as a pale yellow oil in a yield of 32%.

Nuclear Magnetic Resonance Spectrum (CDCl$_3$) δ ppm: 1.05 (3H, triplet, J=6.5 Hz); 2.31–2.58 (2H, multiplet); 2.75–3.00 (4H, multiplet); 3.48 (1H, doublet, J=14.5 Hz); 3.68 (1H, doublet, J=14.5 Hz); 4.97 (1H, singlet); 6.65 (1H, doublet, J=6.0 Hz); 7.05 (1H, doublet, J=6.0 Hz); 7.10–7.65 (4H, multiplet).

Mass spectrum (CI, m/z): 320 (M$^+$+1).

8(b) A procedure similar to that described in Example 2(b) was repeated, using the title compound prepared as described in step (a) above, to obtain the hydrochloride of the title compound as a pale yellow powder, melting at 110°–115° C., in a yield of 25%.

Elemental analysis: Calculated for C$_{17}$H$_{18}$ClNOS.HCl.H$_2$O: C, 54.55%; H, 5.92%; N, 3.74%. Found: C, 54.39%; H, 5.59%; N, 3.73%.

EXAMPLE 9

5-(2-Chloro-α-hexanoylbenzyl)-4,5,6,7-tetrahydrothieno[3,2-c]pyridine (Compound No. 125)

Following a procedure similar to that described in Example 6, except that an equivalent amount of 1-(2-chlorophenyl)-2-heptanone (prepared as described in Preparation 12) was used in place of the 1-(2-fluorophenyl)-2-butanone, the title compound was obtained as a yellow oil in a yield of 10%.

Nuclear Magnetic Resonance Spectrum (CDCl$_3$) δ ppm: 0.90 (3H, triplet, J=7.6 Hz); 1.10–1.60 (6H, multiplet); 2.40 (2H, triplet, J=8.0 Hz); 2.75–3.00 (4H, multiplet); 3.50 (1H, doublet, J=14.5 Hz); 3.70 (1H, doublet, J=14.5 Hz); 5.00 (1H, singlet); 6.65 (1H, doublet, J=6.0 Hz); 7.05 (1H, doublet, J=6.0 Hz); 7.10–7.60 (4H, multiplet).

Mass spectrum (CI, m/z): 362 (M$^+$+1), 262.

EXAMPLE 10

5-(α-Acetyl-2-fluorobenzyl)-4,5,6,7-tetrahydrothieno[3,2-c]pyridine and its maleate (Compound No. 9)

10(a) Following a procedure similar to that described in Example 6, except that an equivalent amount of 1-(2-fluorophenyl)-2-propanone was used in place of the 1-(2-fluorophenyl)-2-butanone, the title compound was obtained as a pale yellow oil in a yield of 55%.

Infrared Absorption Spectrum (thin film) $v_{max}$ cm$^{-1}$: 1715.

Nuclear Magnetic Resonance Spectrum (CDCl$_3$) δ ppm: 2.18 (3H, singlet); 2.80–2.95 (4H, multiplet); 3.55 (1H, doublet, J=12.0 Hz); 3.65 (1H, doublet, J=12.0

Hz); 4.72 (1H, singlet); 6.65 (1H, doublet, J=5.5 Hz); 7.05 (1H, doublet, J=5.5 Hz); 7.10–7.55 (4H, multiplet).

Mass spectrum (CI, m/z): 290 (M++1), 246.

10(b) A procedure similar to that described in Example 2(b) was repeated, using the title compound prepared as described in step (a) above, except that maleic acid was added in place of blowing hydrogen chloride gas through the mixture, to obtain the maleate of the title compound as a pale yellow powder, melting at 104°–106° C., in a yield of 61%.

Elemental analysis: Calculated for $C_{16}H_{16}FNOS \cdot C_4H_4O_4 \cdot \frac{1}{2}H_2O$: C, 57.96%; H, 5.10%; N, 3.38%. Found: C, 58.36%; H, 4.94%; N, 3.39%.

EXAMPLE 11

5-(α-Cyclobutylcarbonyl-2-fluorobenzyl)-4,5,6,7-tetrahydrothieno[3,2-c]pyridine and its maleate (Compound No. 106)

11(a) Following a procedure similar to that described in Example 6, except that an equivalent amount of cyclobutyl 2-fluorobenzyl ketone (prepared as described in Preparation 13) was used in place of the 1-(2-fluorophenyl)-2-butanone, the title compound was obtained as a pale yellow oil in a yield of 24%.

Nuclear Magnetic Resonance Spectrum (CDCl₃) δ ppm: 1.70–2.55 (6H, multiplet); 2.80–3.00 (4H, multiplet); 3.50 (1H, doublet, J=11.0 Hz); 3.62 (1H, doublet, J=11.0 Hz); 3.70–3.90 (1H, multiplet); 4.73 (1H, singlet); 6.65 (1H, doublet, J=6.0 Hz); 7.05 (1H, doublet, J=6.0 Hz); 7.10–7.50 (4H, multiplet).

Mass spectrum (CI, m/z): 330 (M++1), 246.

11(b) A procedure similar to that described in Example 2(b) was repeated, using the title compound prepared as described in step (a) above, except that maleic acid was added in place of blowing hydrogen chloride gas through the mixture, to obtain the maleate of the title compound as a colorless powder, melting at 99°–104° C., in a yield of 57%.

Elemental analysis: Calculated for $C_{16}H_{16}FNOS \cdot C_4H_4O_4 \cdot \frac{1}{2}H_2O$: C, 60.78%; H, 5.54%; N, 3.08%. Found: C, 60.97%; H, 5.48%; N, 2.94%.

Nuclear Magnetic Resonance Spectrum (CDCl₃) δ ppm: 1.70–2.30 (6H, multiplet); 3.10–3.30 (4H, multiplet); 3.68–3.82 (1H, multiplet); 4.30 (2H, broad singlet); 5.55 (1H, singlet); 6.30 (2H, singlet); 6.72 (1H, doublet, J=6.5 Hz); 7.20 (1H, doublet, J=6.5 Hz); 7.25–7.60 (4H, multiplet).

EXAMPLE 12

5-(α-Cyclopropylcarbonyl-2-fluorobenzyl)-4,5,6,7-tetrahydrothieno[3,2-c]pyridine and its hydrochloride (Compound No. 59)

12(a2) Following a procedure similar to that described in Example 6, except that an equivalent amount of cyclopropyl 2-fluorobenzyl ketone (prepared as described in Preparation 8) was used in place of the 1-(2-fluorophenyl)-2-butanone, the title compound was obtained as a colorless oil in a yield of 69%.

Nuclear Magnetic Resonance Spectrum (CDCl₃) δ ppm: 0.78–0.90 (2H, multiplet); 0.98–1.11 (2H, multiplet); 2.22–2.34 (1H, multiplet); 2.72–2.98 (4H, multiplet); 3.58 (1H, doublet, J=4.2 Hz); 3.68 (1H, doublet, J=4.2 Hz); 4.85 (1H, singlet); 6.68 (1H, doublet, J=4.9 Hz); 7.06 (1H, doublet, J=4.9 Hz); 7.20–7.60 (4H, multiplet).

Mass spectrum (CI, m/z): 316 (M++1), 246.

12(b) A procedure similar to that described in Example 2(b) was repeated, using the title compound prepared as described in step (a) above, to obtain the hydrochloride of the title compound as white crystals, melting at 171°–173° C., in a yield of 75%.

Elemental analysis: Calculated for $C_{18}H_{18}FNOS \cdot HCl$: C, 61.44%; H, 5.44%; N, 3.98%. Found: C, 61.37%; H, 5.74%; N, 3.85%.

EXAMPLE 13

5-(α-Butyryl-2-fluorobenzyl)-4,5,6,7-tetrahydrothieno[3,2-c]pyridine and its maleate (Compound No. 116)

13(a) Following a procedure similar to that described in Example 6, except that an equivalent amount of 1-(2-fluorophenyl)-2-pentanone (prepared as described in Preparation 5) was used in place of the 1-(2-fluorophenyl)-2-butanone, the title compound was obtained as a pale yellow oil in a yield of 41%.

Nuclear Magnetic Resonance Spectrum (CDCl₃) δ ppm: 0.82 (3H, triplet, J=9.5 Hz); 1.45–1.70 (2H, multiplet); 2.41 (2H, triplet, J=8.0 Hz); 2.75–2.95 (4H, multiplet); 3.55 (1H, doublet, J=13.0 Hz); 3.62 (1H, doublet, J=13.0 Hz); 4.75 (1H, singlet); 6.65 (1H, doublet, J=6.0 Hz); 7.05 (1H, doublet, J=6.0 Hz); 7.10–7.55 (4H, multiplet).

Mass spectrum (CI, m/z): 318 (M++1), 246.

13(b) A procedure similar to that described in Example 2(b) was repeated, using the title compound prepared as described in step (a) above, except that maleic acid was added in place of blowing hydrogen chloride gas through the mixture, to obtain the maleate of the title compound as a colorless powder, melting at 89°–90° C., in a yield of 36%.

Elemental analysis: Calculated for $C_{18}H_{20}FNOS \cdot C_4H_4O_4$: C, 60.96%; H, 5.58%; N, 3.23%. Found: C, 60.69%; H, 5.43%; N, 3.01%.

EXAMPLE 14

5-(2-Fluoro-α-valerylbenzyl)-4,5,6,7-tetrahydrothieno[3,2-c]pyridine and its maleate (Compound No. 120)

14(a) Following a procedure similar to that described in Example 6, except that an equivalent amount of 1-(2-fluorophenyl)-2-hexanone (prepared as described in Preparation 6) was used in place of the 1-(2-fluorophenyl)-2-butanone, the title compound was obtained as a pale yellow oil in a yield of 46%.

Nuclear Magnetic Resonance Spectrum (CDCl₃) δ ppm: 0.83 (3H, triplet, J=8.0 Hz); 1.12–1.35 (2H, multiplet); 1.40–1.70 (2H, multiplet); 2.45 (2H, triplet, J=8.2 Hz); 2.60–2.90 (4H, multiplet); 3.52 (1H, doublet, J=14.0 Hz); 3.65 (1H, doublet, J=14.0 Hz); 4.75 (1H, singlet); 6.65 (1H, doublet, J=6.0 Hz); 7.05 (1H, doublet, J=6.0 Hz); 7.10–7.50 (4H, multiplet).

Mass spectrum (CI, m/z): 332 (M++1), 246.

14(b) A procedure similar to that described in Example 2(b) was repeated, using the title compound prepared as described in step (a) above, except that maleic acid was added in place of blowing hydrogen chloride gas through the mixture, to obtain the maleate of the title compound as a colorless powder, melting at 92°–93° C., in a yield of 26%.

Elemental analysis: Calculated for $C_{19}H_{22}FNOS \cdot C_4H_4O_4$: C, 61.73%; H, 5.86%; N, 3.13%. Found: C, 61.38%; H, 5.88%; N, 2.59%.

EXAMPLE 15

5-(2-Fluoro-α-pivaloylbenzyl)-4,5,6,7-tetrahydrothieno[3,2-c]pyridine and its hydrochloride (Compound No. 122)

15(a) Following a procedure similar to that described in Example 6, except that an equivalent amount of 1-(2-fluorophenyl)-3,3-dimethyl-2-butanone (prepared as described in Preparation 7) was used in place of the 1-(2-fluorophenyl)-2-butatone, the title compound was obtained as a pale yellow oil in a yield of 87%.

Nuclear Magnetic Resonance Spectrum (CDCl$_3$) δ ppm: 1.10 (9H, singlet); 2.74–3.00 (4H, multiplet); 3.55 (1H, doublet, J=15.0 Hz); 3.66 (1H, doublet, J=15.0 Hz); 5.23 (1H, singlet); 6.63 (1H, doublet, J=6.0 Hz); 7.03 (1H, doublet, J=6.0 Hz); 7.10–7.55 (4H, multiplet).

Mass spectrum (CI, m/z): 332 (M$^+$ +1), 246.

15(b) A procedure similar to that described in Example 2(b) was repeated, using the title compound prepared as described in step (a) above, to obtain the hydrochloride of the title compound as a pale yellow powder, melting at 85°–90° C., in a yield of 34%.

Elemental analysis: Calculated for C$_{19}$H$_{22}$FNOS.HCl.H$_2$O: C, 59.14%; H, 6.23%; N, 3.63%. Found: C, 58.99%; H, 6.57%; N, 3.17%.

EXAMPLE 16

5-[2-Chloro-α-(4-fluorobenzoyl)benzyl]-4,5,6,7-tetrahydrothieno[3,2-c]pyridine and its hydrochloride (Compound No. 149)

16(a) Following a procedure similar to that described in Example 6, except that an equivalent amount of 2-chlorobenzyl 4-fluorophenyl ketone (prepared as described in Preparation 22) was used in place of the 1-(2-fluorophenyl)-2-butanone, the title compound was obtained as a pale yellow oil in a yield of 58%.

Nuclear Magnetic Resonance Spectrum (CDCl$_3$) δ ppm: 2.80–3.00 (4H, multiplet); 3.63 (1H, doublet, J=16.0 Hz); 3.80 (1H, doublet, J=16.0 Hz); 5.80 (1H, singlet); 6.63 (1H, doublet, J=6.0 Hz); 7.00–7.60 (6H, multiplet); 7.95–8.15 (2H, multiplet).

Mass spectrum (CI, m/z): 386 (M$^+$ +1), 262.

16(b) A procedure similar to that described in Example 2(b) was repeated, using the title compound prepared as described in step (a) above, to obtain the hydrochloride of the title compound as a yellowish brown powder, melting at 121°–130° C., in a yield of 40%.

Elemental analysis: Calculated for C$_{21}$H$_{17}$ClFNOS.HCl.½H$_2$O: C, 58.47%; H, 4.44%; N, 3.25%. Found: C, 58.25%; H, 4.86%; N, 3.48%.

EXAMPLE 17

5-(2-Fluoro-α-isobutyrylbenzyl)-4,5,6,7-tetrahydrothieno[3,2-c]pyridine and its maleate. (Compound No. 118).

17(a) Following a procedure similar to that described in Example 6, except that an equivalent amount of 2-fluorobenzyl isopropyl ketone (prepared as described in Preparation 23) was used in place of the 1-(2-fluorophenyl)-2-butanone, the title compound was obtained as a yellow oil in a yield of 44%.

Nuclear Magnetic Resonance Spectrum (CDCl$_3$) δ ppm: 0.95 (3H, doublet, J=7.0 Hz); 1.10 (3H, doublet, J=7.0 Hz); 2.60–2.80 (1H, multiplet); 2.80–2.95 (4H, multiplet); 3.50 (1H, doublet, J=11.0 Hz); 3.65 (1H, doublet, J=11.0 Hz); 4.90 (1H, singlet); 6.65 (1H, doublet, J=5.7 Hz); 7.05 (1H, doublet, J=5.7 Hz); 7.10–7.50 (4H, multiplet).

Mass spectrum (CI, m/z): 318 (M$^+$ +1), 246.

17(b) A procedure similar to that described in Example 2(b) was repeated, using the title compound prepared as described in step (a) above, except that maleic acid was added in place of blowing hydrogen chloride gas through the mixture, to obtain the maleate of the title compound as a colorless powder, melting at 96°–98° C., in a yield of 42%.

Elemental analysis: Calculated for C$_{18}$H$_{20}$FNOS.C$_4$H$_4$O$_4$: C, 61.02%; H, 5.59%; N, 3.23%. Found: C, 60.74%; H, 5.52%; N, 3.23%.

EXAMPLE 18

5-(α-Cyclopropylcarbonyl-2-fluorobenzyl)-2-nitro-4,5,6,7-tetrahydrothieno[3,2-c]pyridine and its hydrochloride (Compound No. 175)

18(a) Following a procedure similar to that described in Example 6, except that an equivalent amount of cyclopropyl 2-fluorobenzyl ketone (prepared as described in Preparation 8) was used in place of the 1-(2-fluorophenyl)-2-butanone and that 2-nitro-4,5,6,7-tetrahydrothieno[3,2-c]pyridine hydrochloride (prepared as described in Preparation 24) was used in place of the 4,5,6,7-tetrahydrothieno[3,2-c]pyridine hydrochloride, the title compound was obtained as a brown oil in a yield of 72%.

Nuclear Magnetic Resonance Spectrum (CDCl$_3$) δ ppm: 0.82–0.92 (2H, multiplet); 1.01–1.11 (2H, multiplet); 2.00–2.20 (1H, multiplet); 2.75–3.05 (4H, multiplet); 3.61 (2H, singlet); 4.91 (1H, singlet); 7.10–7.45 (4H, multiplet); 7.55 (1H, singlet).

Mass spectrum (CI, m/z): 361 (M$^+$ +1), 291.

18(b) A procedure similar to that described in Example 2(b) was repeated, using the title compound prepared as described in step (a) above, to obtain the hydrochloride of the title compound as white crystals, melting at 161°–168° C., in a yield of 79%.

Elemental analysis: Calculated for C$_{18}$H$_{17}$FN$_2$O$_3$S.HCl: C, 54.47%; H, 4.57%; N, 7.06%. Found: C, 54.47%; H, 4.63%; N, 6.89%.

EXAMPLE 19

5-(α-Cyclopropylcarbonyl-2-fluorobenzyl)-4,5,6,7-tetrahydrofuro[3,2-c]pyridine and its hydrochloride (Compound No. 168)

19(a) Following a procedure similar to that described in Example 12, except that an equivalent amount of 4,5,6,7-tetrahydrofuro[3,2-c]pyridine (prepared as described in Preparation 25) was used in place of the 4,5,6,7-tetrahydrothieno[3,2-c]pyridine hydrochloride, the title compound was obtained as a brown oil in a yield of 21%.

Nuclear Magnetic Resonance Spectrum (CDCl$_3$) δ ppm: 0.75–0.95 (2H, multiplet); 0.98–1.10 (2H, multiplet); 2.15–2.31 (1H, multiplet); 2.65–3.05 (4H, multiplet); 3.40–3.60 (2H, multiplet); 4.90 (1H, singlet); 6.15 (1H, doublet, J=5.0 Hz); 7.05–7.55 (5H, multiplet).

Mass spectrum (CI, m/z): 300 (M$^+$ +1), 230.

19(b) A procedure similar to that described in Example 2(b) was repeated, using the title compound prepared as described in step (a) above, to obtain the hydrochloride of the title compound as white crystals, melting at 154°–155° C., in a yield of 39%.

Elemental analysis: Calculated for C$_{18}$H$_{18}$FNO$_2$.HCl: C, 64.38%; H, 5.70%; N, 4.17%. Found: C, 64.37%; H, 5.80%; N, 4.19%.

EXAMPLE 20

5-(α-Cyclopropylcarbonyl-2-fluorobenzyl)-2-oxo-2,4,5,6,7,7a-hexahydrothieno[3,2-c]pyridine and its hydrochloride (Compound No. 235)

20(a) Following a procedure similar to that described in Example 12, except that an equivalent amount of 2-oxo-2,4,5,6,7,7a-hexahydrothieno[3,2-c]pyridine hydrochloride was used in place of the 4,5,6,7-tetrahydrothieno[3,2-c]pyridine hydrochloride, the title compound was obtained as a brown oil in a yield of 32%. Diisopropyl ether was added to this compound to cause crystallization, yielding white crystals, melting at 123°–125° C.

The resulting 5-(α-cyclopropylcarbonyl-2-fluorobenzyl)-2-oxo-2,4,5,6,7,7a-hexahydrothieno[3,2-c]pyridine (Compound No. 235) is believed to contain a small quantity of the tautomeric 5-(α-cyclopropylcarbonyl-2-fluorobenzyl)-2-hydroxy-4,5,6,7-tetrahydrothieno[3,2-c]pyridine (Compound No. 188), from which it was not separated.

Nuclear Magnetic Resonance Spectrum (CDCl$_3$) δ ppm: 0.75–0.96 (2H, multiplet); 0.99–1.14 (2H, multiplet); 1.83–2.01 (1H, multiplet); 2.02–2.17 (1H, multiplet); 2.25–2.45 & 2.47–2.62 (together 2H, each multiplet); 2.85 & 3.10 (together 2H, each doublet, J=12.0 Hz); 3.88–4.01 & 4.03–4.16 (together 2H, each multiplet); 4.85 & 4.89 (together 1H, each singlet); 6.03 & 6.06 (together 1H, each singlet); 7.10–7.45 (4H, multiplet).

Mass spectrum (CI, m/z): 332 (M$^+$+1), 262.

Elemental analysis: Calculated for C$_{18}$H$_{18}$FNO$_2$S: C, 65.23%; H, 5.48%; N, 4.23%. Found: C, 65.09%; H, 5.55%; N, 4.20%.

20(b) A procedure similar to that described in Example 2(b) was repeated, using the title compound prepared as described in step (a) above, to obtain the hydrochloride of the title compound as white crystals, melting at 104°–109° C., in a yield of 46%.

EXAMPLE 21

5-(2-Fluoro-α-propionylbenzyl)-2-oxo-2,4,5,6,7,7a-hexahydrothieno[3,2-c]pyridine and its hydrochloride (Compound No. 234)

21(a) Following a procedure similar to that described in Example 20, except that an equivalent amount of 1-(2-fluorophenyl)-2-butanone (prepared as described in Preparation 9) was used in place of the cyclopropyl 2-fluorobenzyl ketone, the title compound was obtained as a brown oil in a yield of 36%.

The resulting 5-(2-fluoro-α-propionylbenzyl)-2-oxo-2,4,5,6,7,7a-hexahydrothieno[3,2-c]pyridine (Compound No. 234) is believed to contain a small quantity of the tautomeric 5-(2-fluoro-α-propionylbenzyl)-2-hydroxy-4,5,6,7-tetrahydrothieno[3,2-c]pyridine (Compound No. 187).

Nuclear Magnetic Resonance Spectrum (CDCl$_3$) δ ppm: 1.00 (3H, triplet, J=9.1 Hz); 1.82–1.98 (1H, multiplet); 2.25–2.50 (4H, multiplet); 2.85 & 3.05 (together 2H, each doublet, J=14.0 Hz); 3.84–3.95 & 4.04–4.17 (together 2H, each multiplet); 4.72 & 4.76 (together 1H, each singlet); 6.03 & 6.07 (together 1H, each singlet); 7.15–7.40 (4H, multiplet).

Mass spectrum (CI, m/z): 320 (M$^+$+1), 262.

21(b) A procedure similar to that described in Example 2(b) was repeated, using the title compound prepared as described in step (a) above, to obtain the hydrochloride of the title compound as white crystals, melting at 110°–115° C., in a yield of 78%.

EXAMPLE 22

5-(2-Chloro-α-cyclopropylcarbonylbenzyl)-2-oxo-2,4,5,6,7,7a-hexahydrothieno[3,2-c]pyridine (Compound No. 233)

Following a procedure similar to that described in Example 5, except that an equivalent amount of 2-oxo-2,4,5,6,7,7a-hexahydrothieno[3,2-c]pyridine hydrochloride was used in place of the 4,5,6,7-tetrahydrothieno[3,2-c]pyridine hydrochloride, a yellow oil was obtained. The oil was crystallized from diisopropyl ether to give the title compound as pale brown crystals, melting at 119°–123° C. in a yield of 8%.

The resulting 5-(2-chloro-α-cyclopropylcarbonylbenzyl)-2-oxo-2,4,5,6,7,7a-hexahydrothieno[3,2-c]pyridine (Compound No. 233) is believed to contain a small quantity of the tautomeric 5-(2-chloro-α-cyclopropylcarbonylbenzyl)-2-hydroxy-4,5,6,7-tetrahydrothieno[3,2-c]pyridine (Compound No. 186).

Nuclear Magnetic Resonance Spectrum (CDCl$_3$) δ ppm: 0.75–1.10 (4H, multiplet); 1.75–2.10 (2H, multiplet); 2.25–2.70 (2H, multiplet); 2.90–3.30 (2H, multiplet); 3.75–4.20 (2H, multiplet); 5.09 & 5.10 (together 1H, each singlet); 5.98 & 6.07 (together 1H, each singlet); 7.10–7.50 (4H, multiplet).

Mass spectrum (CI, m/z): 348 (M$^+$+1), 278.

EXAMPLE 23

2-Acetoxy-5-(α-cyclopropylcarbonyl-2-fluorobenzyl)-4,5,6,7-tetrahydrothieno[3,2-c]pyridine (Compound No. 190)

2.6 g (7.8 mmole) of 5-(α-cyclopropylcarbonyl-2-fluorobenzyl)-2-oxo-2,4,5,6,7,7a-hexahydrothieno[3,2-c]pyridine (prepared as described in Example 20) were dissolved in a mixture of 10 ml of dimethylformamide and 5 ml of acetic anhydride, and then 0.35 g (8.6 mmole) of a 60% w/w dispersion of sodium hydride in mineral oil was added to the resulting solution, whilst ice-cooling; the mixture was then stirred for 20 minutes at the same temperature, after which it was stirred for a further 3 hours at room temperature. At the end of this time, 300 ml of ethyl acetate were added to the mixture, which was then washed four times, each time with 50 ml of a saturated aqueous solution of sodium chloride. The organic layer was separated and dried over anhydrous sodium sulfate, and the solvent was removed by evaporation under reduced pressure. The resulting residue was subjected to silica gel column chromatography, using a 100:3 by volume mixture of toluene and ethyl acetate as the eluent, to give a yellow oil. This oil was crystallized from diisopropyl ether, to obtain the title compound as white crystals, melting at 120°–121.5° C., in a yield of 65%.

Infrared Absorption Spectrum (KBr) $\nu_{max}$ cm$^{-1}$: 1758, 1704.

Nuclear Magnetic Resonance Spectrum (CDCl$_3$) δ ppm: 0.80–0.95 (2H, multiplet); 0.99–1.16 (2H, multiplet); 2.27 (3H, singlet); 2.21–2.34 (1H, multiplet); 2.70–2.95 (4H, multiplet); 3.47 (1H, doublet, J=15.0 Hz); 3.57 (1H, doublet, J=15.0 Hz); 4.83 (1H, singlet); 6.27 (1H, singlet); 7.10–7.55 (4H, multiplet).

Mass spectrum (CI, m/z): 374 (M$^+$+1), 304.

Elemental analysis: Calculated for C$_{20}$H$_{20}$FNO$_3$S: C, 64.32%; H, 5.40%; N, 3.75%. Found: C, 64.46%; H, 5.39%; N, 3.73%.

EXAMPLE 24

5-(α-Cyclopropylcarbonyl-2-fluorobenzyl)-2-propionyloxy-4,5,6,7-tetrahydrothieno[3,2-c]pyridine (Compound No. 192)

Following a procedure similar to that described in Example 23, except that an equivalent amount of propionic anhydride was used in place of the acetic anhydride, the title compound was obtained as white crystals, melting at 101°–102° C., in a yield of 16%.

Infrared Absorption Spectrum (KBr) $\nu_{max}$ cm$^{-1}$: 1705, 1760.

Nuclear Magnetic Resonance Spectrum (CDCl$_3$) δ ppm: 0.75–0.90 (2H, multiplet); 0.90–1.10 (2H, multiplet); 1.21 (3H, triplet, J=6.7 Hz); 2.15–2.37 (1H, multiplet); 2.55 (2H, quartet, J=6.7 Hz); 2.65–2.95 (4H, multiplet); 3.40–3.60 (2H, multiplet); 4.80 (1H, singlet); 6.25 (1H, singlet); 7.05–7.55 (4H, multiplet).

Mass spectrum (CI, m/z): 388 (M$^+$ +1), 318.

Elemental analysis: Calculated for C$_{21}$H$_{22}$FNO$_3$S: C, 65.10%; H, 5.72%; N, 3.61%. Found: C, 64.80%; H, 5.72%; N, 3.61%.

EXAMPLE 25

2-Butyryloxy-5-(α-cyclopropylcarbonyl-2-fluorobenzyl)-4,5,6,7-tetrahydrothieno[3,2-c]pyridine (Compound No. 194)

Following a procedure similar to that described in Example 23, except that an equivalent amount of butyric anhydride was used in place of the acetic anhydride, the title compound was obtained as white crystals, melting at 84°–85° C., in a yield of 39%.

Infrared Absorption Spectrum (KBr) $\nu_{max}$ cm$^{-1}$: 1756, 1706.

Nuclear Magnetic Resonance Spectrum (CDCl$_3$) δ ppm: 0.75–1.10 (7H, multiplet); 1.65–1.85 (2H, multiplet); 2.21–2.34 (1H, multiplet); 2.49 (2H, triplet, J=7.0 Hz); 2.70–3.00 (4H, multiplet); 3.52 (2H, broad triplet, J=16.0 Hz); 4.82 (1H, singlet); 6.25 (1H, singlet); 7.05–7.55 (4H, multiplet).

Mass spectrum (CI, m/z): 402 (M$^+$ +1), 332.

Elemental analysis: Calculated for C$_{22}$H$_{24}$FNO$_3$S: C, 65.81%; H, 6.03%; N, 3.49%. Found: C, 65.92%; H, 5.91%; N, 3.41%.

EXAMPLE 26

5-(α-Cyclopropylcarbonyl-2-fluorobenzyl)-2-pivaloyloxy-4,5,6,7-tetrahydrothieno[3,2-c]pyridine (Compound No. 196)

Following a procedure similar to that described in Example 23, except that an equivalent amount of pivalic anhydride was used in place of the acetic anhydride, the title compound was obtained as white crystals, melting at 91°–94° C., in a yield of 44%.

Infrared Absorption Spectrum (KBr) $\nu_{max}$ cm$^{-1}$: 1749, 1700.

Nuclear Magnetic Resonance Spectrum (CDCl$_3$) δ ppm: 0.79–0.92 (2H, multiplet); 0.98–1.09 (2H, multiplet); 1.31 (9H, singlet); 2.23–2.36 (1H, multiplet); 2.70–2.95 (4H, multiplet); 3.47 (1H, doublet, J=14.5 Hz); 3.58 (1H, doublet, J=14.5 Hz); 4.83 (1H, singlet); 6.26 (1H, singlet); 7.05–7.55 (4H, multiplet).

Mass spectrum (CI, m/z): 416 (M$^+$ +1), 346.

Elemental analysis: Calculated for C$_{23}$H$_{26}$FNO$_3$S: C, 66.48%; H, 6.31%; N, 3.37%. Found: C, 66.21%; H, 6.40%; N, 3.38%.

EXAMPLE 27

5-(α-Cyclopropylcarbonyl-2-fluorobenzyl)-2-nonanoyloxy-4,5,6,7-tetrahydrothieno[3,2-c]pyridine (Compound No. 199)

1.0 g (3.0 mmole) of 5-(α-cyclopropylcarbonyl-2-fluorobenzyl)-2-oxo-2,4,5,6,7,7a-hexahydrothieno[3,2-c]pyridine (prepared as described in Example 20) was dissolved in 15 ml of dimethylformamide, and then 0.18 g (4.5 mmole) of a 60% w/w dispersion of sodium hydride in mineral oil and 0.82 ml (4.5 mmole) of nonanoyl chloride were added, in that order, to the resulting mixture, whilst ice-cooling. The resulting reaction mixture was then stirred at the same temperature for 30 minutes, after which it was stirred at room temperature for a further 5 hours. 300 ml of ethyl acetate were then added to the mixture, which was then washed with a saturated aqueous solution of sodium hydrogencarbonate and with a saturated aqueous solution of sodium chloride, in that order. The organic layer was separated and dried over anhydrous sodium sulfate, and the solvent was removed by evaporation under reduced pressure. The resulting residue was subjected to silica gel column chromatography, using a 100:2 by volume mixture of toluene and ethyl acetate as the eluent, to give a yellow oil. The oil was crystallized from petroleum ether to obtain the title compound as white crystals, melting at 45°–48° C., in a yield of 40%.

Nuclear Magnetic Resonance Spectrum (CDCl$_3$) δ ppm: 0.80–1.80 (19H, multiplet); 2.21–2.32 (1H, multiplet); 2.53 (2H, triplet, J=7.5 Hz); 2.70–2.95 (4H, multiplet); 3.48 (1H, doublet, J=15.0 Hz); 3.57 (1H, doublet, J=15.0 Hz); 4.84 (1H, singlet); 6.27 (1H, singlet); 7.05–7.55 (4H, multiplet).

Mass spectrum (CI, m/z): 472 (M$^+$ +1), 402.

Elemental analysis: Calculated for C$_{27}$H$_{34}$FNO$_3$S: C, 68.76%; H, 7.27%; N, 2.97%. Found: C, 68.56%; H, 7.49%; N, 2.97%.

EXAMPLE 28

5-(α-Cyclopropylcarbonyl-2-fluorobenzyl)-2-decanoyloxy-4,5,6,7-tetrahydrothieno[3,2-c]pyridine and its hydrochloride (Compound No. 200)

28(a) Following a procedure similar to that described in Example 27, except that an equivalent amount of decanoyl chloride was used in place of the nonanoyl chloride, the title compound was obtained as a yellow oil in a yield of 40%.

Nuclear Magnetic Resonance Spectrum (CDCl$_3$) δ ppm: 0.80–1.80 (21H, multiplet); 2.18–2.32 (1H, multiplet); 2.52 (2H, triplet, J=7.5 Hz); 2.70–2.97 (4H, multiplet); 3.50 (1H, doublet, J=14.5 Hz); 3.59 (1H, doublet, J=14.5 Hz); 4.85 (1H, singlet); 6.26 (1H, singlet); 7.20–7.55 (4H, multiplet).

Mass spectrum (CI, m/z): 486 (M$^+$ +1), 416.

28 (b) A procedure similar to that described in Example 2(b) was repeated, using the title compound prepared as described in step (a) above, except that diisopropyl ether was used as a solvent in place of the diethyl ether, to give the hydrochloride of the title compound as yellow crystals, melting at 62°–64° C., in a yield of 81%.

Elemental analysis: Calculated for C$_{28}$H$_{36}$FNO$_3$S.HCl: C, 64.41%; H, 7.14%; N, 2.68%. Found: C, 64.12%; H, 7.05%; N, 2.63%.

EXAMPLE 29

5-(α-Cyclopropylcarbonyl-2-fluorobenzyl)-2-palmitoyloxy-4,5,6,7-tetrahydrothieno[3,2-c]pyridine (Compound No. 201)

Following a procedure similar to that described in Example 27, except that an equivalent amount of palmitoyl chloride was used in place of the nonanoyl chloride, the title compound was obtained as white crystals, melting at 66°–68° C., in a yield of 21%.

Nuclear Magnetic Resonance Spectrum (CDCl$_3$) δ ppm: 0.80–1.80 (33H, multiplet); 2.20–2.32 (1H, multiplet); 2.51 (2H, triplet, J=7.5 Hz); 2.70–2.95 (4H, multiplet); 3.48 (1H, doublet, J=15.0 Hz); 3.58 (1H, doublet, J=15.0 Hz); 4.84 (1H, singlet); 6.26 (1H, singlet); 7.10–7.55 (4H, multiplet).

Mass spectrum (CI, m/z): 570 (M+ +1), 500.

Elemental analysis: Calculated for $C_{34}H_{48}FNO_3S$: C, 71.66%; H, 8.49%; N, 2.46%. Found: C, 71.72%; H, 8.62%; N, 2.43%.

EXAMPLE 30

2-t-Butoxycarbonyloxy-5-(α-cyclopropylcarbonyl-2-fluorobenzyl)-4,5,6,7-tetrahydrothieno[3,2-c]pyridine (Compound No. 203)

Following a procedure similar to that described in Example 23, except that an equivalent amount of di-t-butyl dicarbonate was used in place of the acetic anhydride, the title compound was obtained as white crystals, melting at 98°–99° C., in a yield of 15%.

Nuclear Magnetic Resonance Spectrum (CDCl₃) δ ppm: 0.80–0.90 (2H, multiplet); 0.98–1.09 (2H, multiplet); 1.55 (9H, singlet); 2.20–2.34 (1H, multiplet); 2.70–2.95 (4H, multiplet); 3.40–3.60 (2H, multiplet); 4.83 (1H, singlet); 6.27 (1H, singlet); 7.07–7.52 (4H, multiplet).

Mass spectrum (CI, m/z): 432 (M+ +1), 362.

Elemental analysis: Calculated for $C_{23}H_{26}FNO_4S$: C, 64.02%; H, 6.07%; N, 3.25%. Found: C, 63.57%; H, 6.03%; N, 3.27%.

EXAMPLE 31

2-Amino-5-(α-Cyclopropylcarbonyl-2-fluorobenzyl)-4,5,6,7-tetrahydrothieno[3,2-c]pyridine (Compound No. 177)

5 ml of hydrochloric acid were added to 0.4 g of 5-(α-cyclopropylcarbonyl-2-fluorobenzyl)-2-nitro-4,5,6,7-tetrahydrothieno[3,2-c]pyridine hydrochloride (prepared as described in Example 18), and then 0.23 g of tin powder was added to the resulting mixture, whilst stirring, after which the mixture was stirred at room temperature for a further hour. 10 ml of water were added to the reaction mixture, which was then extracted with methylene chloride. The methylene chloride layer was removed, and the aqueous layer was concentrated to dryness by evaporation under reduced pressure, and then crystallized from diethyl ether, to give a complex of the title compound with stannic chloride as a pale yellow powder in a yield of 72%.

Nuclear Magnetic Resonance Spectrum (CD₃OD) δ ppm: 0.95–1.05 (2H, multiplet); 1.20–1.35 (2H, multiplet); 1.85–1.99 (1H, multiplet); 3.60–3.80 (2H, multiplet); 6.07 (1H, singlet); 7.35–7.80 (4H, multiplet).

EXAMPLE 32

2-Acetylamino-5-(α-cyclopropylcarbonyl-2-fluorobenzyl)-4,5,6,7-tetrahydrothieno[3,2-c]pyridine (Compound No. 179)

1.85 g (5.13 mmole) of 5-(α-cyclopropylcarbonyl-2-fluorobenzyl)-2-nitro-4,5,6,7-tetrahydrothieno[3,2-c]pyridine (prepared as described in Example 18) were dissolved in a mixture of 20 ml of acetic acid and 2 ml of acetic anhydride, and then 1.85 g of iron powder were added to the solution, whilst stirring at room temperature; the mixture was then stirred at the same temperature for 90 minutes. At the end of this time, water and chloroform were added to the reaction mixture, and the mixture was neutralized with sodium carbonate. The inorganic salt thus precipitated was filtered off, the remaining organic layer was separated and the aqueous layer was extracted with chloroform. The organic layer and the extract were combined and dried over anhydrous magnesium sulfate, and then the solvent was removed by distillation under reduced pressure. The resulting residue was then subjected to silica gel column chromatography, using a 6:4 by volume mixture of toluene and ethyl acetate as the eluent, to give 1.86 g of the title compound. This was crystallized from diisopropyl ether to obtain 1.37 g of the title compound as white crystals, melting at 155°–159° C.

Nuclear Magnetic Resonance Spectrum (CDCl₃) δ ppm: 0.78–0.94 (2H, multiplet); 0.98–1.12 (2H, multiplet); 2.17 (3H, singlet); 2.15–2.32 (1H, multiplet); 2.70–2.99 (4H, multiplet); 3.50 (1H, doublet, J=11.4 Hz); 3.60 (1H, doublet, J=11.4 Hz); 4.86 (1H, singlet); 6.27 (1H, singlet); 7.10–7.55 (4H, multiplet); 7.80–8.00 (1H, broad singlet).

Mass spectrum (CI, m/z): 373 (M+ +1), 303.

Elemental analysis: Calculated for $C_{20}H_{21}FN_2O_2S$: C, 64.49%; H, 5.68%; N, 7.52%. Found: C, 64.38%; H, 5.50%; N, 7.38%.

EXAMPLE 33

2-Butyrylamino-5-(α-cyclopropylcarbonyl-2-fluorobenzyl)-4,5,6,7-tetrahydrothieno[3,2-c]pyridine (Compound No. 181)

Following a procedure similar to that described in Example 32, except that equivalent amounts of butyric acid and butyric anhydride were used in place of the acetic acid and acetic anhydride, the title compound was obtained as white crystals, melting at 154°–157° C., in a yield of 61%.

Nuclear Magnetic Resonance Spectrum (CDCl₃) δ ppm: 0.78–0.94 (2H, multiplet); 0.90–1.10 (5H, multiplet); 1.65–1.82 (2H, multiplet); 2.21–2.39 (3H, multiplet); 2.69–2.95 (4H, multiplet); 3.47 (1H, doublet, J=11.4 Hz); 3.56 (1H, doublet, J=11.4 Hz); 4.81 (1H, singlet); 6.25 (1H, singlet); 7.10–7.60 (4H, multiplet); 7.70 (1H, singlet).

Mass spectrum (CI m/z): 401 (M+ +1), 331.

Elemental analysis: Calculated for $C_{22}H_{25}FN_2O_2S$: C, 65.97%; H, 6.29%; N, 6.99%. Found: C, 65.95%; H, 6.36%; N, 6.95%.

EXAMPLE 34

Optically active 5-(α-cyclopropylcarbonyl-2-fluorobenzyl)-4,5,6,7-tetrahydrothieno[3,2-c]pyridine (Compound No. 59)

0.3 g of 5-(α-cyclopropylcarbonyl-2-fluorobenzyl)-4,5,6,7-tetrahydrothieno[3,2-c]pyridine (prepared as described in Example 12) was separated into fractions by liquid chromatography [column: DAICEL CHIRALPAC AD (trade name), 1 cm×25 cm); eluent: a 1000:40:1 by volume mixture of hexane, isopropanol and diethylamine; column temperature: 35° C.; flow rate: 4 ml/minute], to obtain an optically active isomer A [retention time: 8.3 minutes; specific rotation angle $[α]_D^{25}$: 109.4° (C=1.80, CHCl₃)] and an isomer B [retention time: 9.9 minutes; specific rotation angle $[α]_D^{25}$: +100.1° (C=1.90, CHCl₃)].

Isomers A and B were separately dissolved in diethyl ether, and then hydrogen chloride gas was allowed to act upon the resulting solutions to obtain 0.13 g and 0.12 g of the hydrochlorides of isomer A and isomer B, respectively, as white crystals.

Hydrochloride of isomer A melting at 106°–110° C.

Elemental analysis: Calculated for C$_{18}$H$_{18}$FNOS.HCl.$\frac{3}{4}$H$_2$O: C, 59.17%; H, 5.65%; N, 3.83%. Found: C, 59.06%; H, 5.74%; N, 3.90%.

Hydrochloride of isomer B melting at 105°–110° C.

Elemental analysis: Calculated for C$_{18}$H$_{18}$FNOS.HCl.$\frac{1}{2}$H$_2$O: C, 59.91%; H, 5.59%; N, 3.88%. Found: C, 59.80%; H, 5.84%; N, 3.79%.

EXAMPLE 35

5-(α-Cyclopropylcarbonyl-2-fluorobenzyl)-2-pivaloyloxymethoxy-4,5,6,7-tetrahydrothieno[3,2-c]pyridine (Compound No. 207)

1.0 g (3.0 mmole) of 5-(α-cyclopropylcarbonyl-2-fluorobenzyl)-2-oxo-2,4,5,6,7,7a-hexahydrothieno[3,2-c]pyridine (prepared as described in Example 20) was dissolved in 20 ml of dimethylformamide, and then 100 mg (0.6 mmole) of potassium iodide and 0.13 g (3.3 mmole) of a 60% dispersion of sodium hydride in mineral oil were added to the solution at room temperature; the mixture was then stirred at the same temperature for 10 minutes. At the end of this time, a solution of 0.43 ml (3.0 mmole) of pivaloyloxymethyl chloride in 5 ml of dimethylformamide was added dropwise to the resulting mixture over a period of 10 minutes, and the resulting mixture was stirred at room temperature for 30 minutes. 300 ml of ethyl acetate were added to the reaction mixture, and the mixture was washed three times, each time with 50 ml of a saturated aqueous solution of sodium hydrogen-carbonate. The organic layer was dried over anhydrous sodium sulfate, and the solvent was removed by evaporation under reduced pressure. The resulting residue was subjected to silica gel column chromatography, using a 100:3 by volume mixture of toluene and ethyl acetate as the eluent, to give the title compound as a colorless oil in a yield of 15%.

Infrared Absorption Spectrum (thin film) $\nu_{max}$ cm$^{-1}$: 1715, 1702.

Nuclear Magnetic Resonance Spectrum (CDCl$_3$) δ ppm: 0.79–0.93 (2H, multiplet); 0.99–1.14 (2H, multiplet); 1.22 (9H, singlet); 2.18–2.31 (1H, multiplet); 2.65–2.95 (4H, multiplet); 3.44 (1H, doublet, J=15.5 Hz); 3.55 (1H, doublet, J=15.5 Hz); 4.84 (1H, singlet); 5.57 (2H, singlet); 6.04 (1H, singlet); 7.05–7.50 (4H, multiplet).

Mass spectrum (CI, m/z): 446 (M$^+$+1), 376.

EXAMPLE 36

5-(α-Cyclopropylcarbonyl-2-fluorobenzyl)-2-methoxy-4,5,6,7-tetrahydrothieno[3,2-c]pyridine and its hydrochloride (Compound No. 210)

36(a) A procedure similar to than described in Example 35 was repeated, except that an equivalent amount of methyl iodide was used in place of the pivaloyloxymethyl chloride and potassium iodide, to give the title compound as a yellow oil in a yield of 45%.

Nuclear Magnetic Resonance Spectrum (CDCl$_3$) δ ppm: 0.80–0.92 (2H, multiplet); 1.00–1.10 (2H, multiplet); 2.20–2.36 (1H, multiplet); 2.65–2.96 (4H, multiplet); 3.42 (1H, doublet, J=14.5 Hz); 3.55 (1H, doublet, J=14.5 Hz); 3.80 (3H, singlet); 4.82 (1H, singlet); 5.80 (1H, singlet); 7.10–7.60 (4H, multiplet).

Mass spectrum (CI, m/z): 346 (M$^+$+1), 276.

36(b) Following a procedure similar to that described in Example 2(b), using the whole of the title compound prepared as described in step (a) above, the hydrochloride of the title compound was obtained as white crystals, melting at 102°–106° C., in a yield of 78%.

Elemental analysis: Calculated for C$_{19}$H$_{20}$FNO$_2$S.HCl.$\frac{1}{2}$H$_2$O: C, 58.38%; H, 5.67%; N, 3.58%. Found: C, 58.08%; H, 5.77%; N, 3.53%.

EXAMPLE 37

5-[α-(2-Fluorocyclopropylcarbonyl-2-fluorobenzyl]-2-oxo-2,4,5,6,7,7a-hexahydrothieno[3,2-c]pyridine (Compound No. 275)

Following a procedure similar to that described in Example 1, except that equivalent amounts of 2-oxo-2,4,5,6,7,7a-hexahydrothieno[3,2-c]pyridine hydrochloride and 2-fluoro-α-(2-fluorocyclopropylcarbonyl)benzyl bromide (prepared as described in Preparation 27) were used in place of the 4,5,6,7-tetrahydrothieno[3,2-c]pyridine hydrochloride and 2-chloro-α-trifluoroacetylbenzyl bromide, the title compound was obtained as a yellow oil in a yield of 31%.

The resulting 5-[α-(2-fluorocyclopropylcarbonyl-2-fluorobenzyl]-2-oxo-2,4,5,6,7,7a-hexahydrothieno[3,2-c]pyridine (Compound No. 275) is believed to contain a small quantity of the tautomeric 5-[α-(2-fluorocyclopropylcarbonyl-2-fluorobenzyl]-2-hydroxy-4,5,6,7-tetrahydrothieno[3,2-c]pyridine (Compound No. 274), from which it was not separated.

Infrared Absorption Spectrum (thin film) $\nu_{max}$ cm$^{-1}$: 1680.

Nuclear Magnetic Resonance Spectrum (CDCl$_3$) δ ppm: 1.48–1.55 (2H, multiplet); 3.85–2.01 (1H, multiplet); 2.30–2.51 (2H, multiplet); 2.53–2.90 (1H, multiplet); 3.00–3.20 (2H, multiplet); 3.83–4.01 & 4.03–4.18 (together 2H, each multiplet); 4.46–4.60 & 4.79–4.92 (together 2H, each multiplet); 6.05 & 6.09 (together 1H, each singlet); 7.10–7.45 (4H, multiplet).

Mass spectrum (CI, m/z): 350 (M$^+$+1), 262.

PREPARATION 1

3-(2-Chlorobenzyl)-5,6-dihydro-1,4,2-dioxazine

A solution of 5.0 g (29.3 mmole) of o-chlorophenylacetic acid and 0.3 g of p-toluenesulfonic acid monohydrate in 50 ml of methanol was heated under reflux for 6 hours. At the end of this time, 3.1 g (44 mmole) of hydroxylamine hydrochloride were added to the reaction mixture, followed by 2.1 g of sodium methoxide. The resulting reaction mixture was then heated under reflux for 10 hours. 14.2 g (103 mmole) of potassium carbonate and 5.1 ml of 1,2-dibromoethane were then added to the resulting reaction mixture, followed by 15 ml of water. The reaction mixture was then heated under reflux for a further 10 hours. At the end of this time, 200 ml of ethyl acetate were added to the reaction mixture, and the organic layer was separated, washed with a saturated aqueous solution of sodium hydrogen-carbonate and dried over anhydrous sodium sulfate; the solvent was then removed by distillation under reduced pressure. The residue thus obtained was subjected to silica gel column chromatography, using a 9:1 by volume mixture of toluene and ethyl acetate as the eluent, to give 4.9 g of the title compound as an oil.

Nuclear Magnetic Resonance Spectrum (CDCl$_3$) δ ppm: 3.67 (2H, singlet); 4.05 (2H, triplet, J=4.2 Hz); 4.29 (2H, triplet, J=4.2 Hz); 7.10–7.40 (4H, multiplet).

Mass spectrum (CI, m/z): 212 (M$^+$+1), 176.

PREPARATION 2

3-(2-Fluorobenzyl)-5,6-dihydro-1,4,2-dioxazine

A procedure similar to that described in Preparation 1 was repeated, except that an equivalent amount of o-fluorophenylacetic acid was used in place of the o-chlorophenylacetic acid, to give the title compound as a colorless oil in a yield of 45%.

Mass spectrum (CI, m/z): 196 (M+ +1), 109.

PREPARATION 3

3-(2,6-Difluorobenzyl)-5,6-dihydro-1,4,2-dioxazine

A procedure similar to that described in Preparation 1 was repeated, except that an equivalent amount of 2,6-difluorophenylacetic acid was used in place of the o-chlorophenylacetic acid, to give the title compound as a colorless oil in a yield of 45%.

Nuclear Magnetic Resonance Spectrum (CDCl₃) δ ppm: 3.61 (2H, singlet); 4.04 (2H, triplet, J=4.1 Hz); 4.30 (2H, triplet, J=4.1 Hz); 6.80–7.30 (4H, multiplet).

Mass spectrum (CI, m/z): 214 (M+ +1), 127.

PREPARATION 4

2-Chlorobenzyl cyclopropyl ketone 10 ml of anhydrous diethyl ether were added to 0.45 g (18.5 mmole) of metallic magnesium, and then a solution of 2.0 ml (15.4 mmole) of 2-chlorobenzyl bromide in 10 ml of diethyl ether was slowly added dropwise to the resulting mixture, whilst stirring; the mixture was then stirred at room temperature for one hour. The resulting solution was slowly added dropwise to a solution of 1.1 ml of cyclopropyl cyanide in 10 ml of diethyl ether over a period of 30 minutes, and then the mixture was stirred at room temperature for 2 hours. At the end of this time, a saturated aqueous solution of ammonium chloride was added to the reaction mixture, and the mixture was stirred at room temperature for 15 minutes. 200 ml of ethyl acetate were then added to the reaction mixture, and the organic layer was separated, washed with water, with a saturated aqueous solution of sodium hydrogencarbonate and with a saturated aqueous solution of sodium chloride, in that order, and dried over anhydrous sodium sulfate; the solvent was then removed by distillation under reduced pressure. The residue thus obtained was subjected to silica gel column chromatography, using a 9:1 by volume mixture of toluene and ethyl acetate as the eluent, to give 2.0 g of the title compound as a colorless oil.

Infrared Absorption Spectrum (thin film) $\nu_{max}$ cm⁻¹: 1695.

Nuclear Magnetic Resonance Spectrum (CDCl₃) δ ppm: 0.86–0.92 (2H, multiplet); 1.06–1.12 (2H, multiplet); 1.96–2.02 (1H, multiplet); 3.98 (2H, singlet); 7.10–7.50 (4H, multiplet).

Mass spectrum (CI, m/z): 195 (M+ +1), 159.

PREPARATION 5

1-(2-Fluorophenyl)-2-pentanone

A procedure similar to that described in Preparation 4 was repeated, except that equivalent amounts of 2-fluorobenzyl bromide and butyl cyanide were used in place of the 2-chlorobenzyl bromide and cyclopropyl cyanide, to give the title compound as a colorless oil in a yield of 36%.

Nuclear Magnetic Resonance Spectrum (CDCl₃) δ ppm: 0.90 (3H, triplet, J=8.0 Hz); 1.52–1.73 (2H, multiplet); 2.45 (2H, triplet, J=8.0 Hz); 3.70 (2H, singlet); 7.00–7.30 (4H, multiplet).

Mass spectrum (CI m/z): 181 (M+ +1), 109.

PREPARATION 6

1-(2-Fluorophenyl)-2-hexanone

A procedure similar to that described in Preparation 4 was repeated, except that equivalent amounts of 2-fluorobenzyl bromide and pentyl cyanide were used in place of the 2-chlorobenzyl bromide and cyclopropyl cyanide, to give the title compound as a colorless oil in a yield of 46%.

Nuclear Magnetic Resonance Spectrum (CDCl₃) δ ppm: 0.90 (3H, triplet, J=8.0 Hz); 1.20–1.39 (2H, multiplet); 1.50–1.65 (2H, multiplet); 2.50 (2H, triplet, J=8.0 Hz); 3.70 (2H, singlet); 7.00–7.30 (4H, multiplet).

Mass spectrum (CI, m/z): 195 (M+ +1), 109.

PREPARATION 7

1-(2-Fluorophenyl)-3,3-dimethyl-2-butanone

A procedure similar to that described in Preparation 4 was repeated, except that equivalent amounts of 2-fluorobenzyl bromide and t-butyl cyanide were used in place of the 2-chlorobenzyl bromide and cyclopropyl cyanide, to give the title compound as a colorless oil in a yield of 42%.

Nuclear Magnetic Resonance Spectrum (CDCl₃) δ ppm: 1.25 (9H, singlet); 3.80 (2H, singlet); 7.00–7.30 (4H, multiplet).

Mass spectrum (CI, m/z): 195 (M+ +1), 109.

PREPARATION 8

Cyclopropyl 2-fluorobenzyl ketone

A procedure similar to that described in Preparation 4 was repeated, except that equivalent amounts of 2-fluorobenzyl bromide and cyclopropyl cyanide were used in place of the 2-chlorobenzyl bromide and cyclopropyl cyanide, to give the title compound as a colorless oil in a yield of 70%.

Nuclear Magnetic Resonance Spectrum (CDCl₃) δ ppm: 0.82–0.98 (2H, multiplet); 1.03–1.17 (2H, multiplet); 1.92–2.06 (1H, multiplet); 3.86 (2H, singlet); 7.10–7.30 (4H, multiplet).

Mass spectrum (CI, m/z): 179 (M+ +1).

PREPARATION 9

1-(2-Fluorophenyl)-2-butanone

9(a) 1-(2-Fluorophenyl)-2-nitro-1-butene 30 ml of acetic acid were added to 4.73 g (38.11 mmole) of 2-fluorobenzaldehyde, 4.41 g (49.49 mmole) of nitropropane and 3.23 g (41.90 mmole) of ammonium acetate, and the resulting mixture was heated under reflux, whilst stirring, for 4 hours. At the end of this time, the reaction mixture was cooled to room temperature, neutralized with an aqueous solution of sodium hydrogencarbonate and extracted with diethyl ether. The extract was dried over anhydrous magnesium sulfate, and then xylene was added to the solution. The mixture was concentrated by evaporation under reduced pressure, to give 7.4 g of the title compound as a pale yellow oil.

Nuclear Magnetic Resonance Spectrum (CDCl₃) δ ppm: 1.25 (3H, triplet, J=6.5 Hz); 2.80 (2H, quartet, J=6.5 Hz); 7.00–7.60 (4H, multiplet); 8.03 (1H, singlet).

Mass spectrum (CI, m/z): 196 (M+ +1), 149.

9(b) 1-(2-Fluorophenyl)-2-butanone 100 ml of 90% v/v aqueous acetic acid were added to 7.4 g of 1-(2-fluorophenyl)-2-nitro-1-butene [prepared as described in step (a) above], and then 12.11 g (190 mmole) of a zinc powder were added in portions to the resulting solution, whilst heating. The mixture was then heated under reflux, whilst stirring, for 4 hours. At the end of this time, the reaction mixture was left to stand overnight, and then the crystals which had precipitated were filtered off and washed with toluene. The filtrate was combined with the toluene washings, and the mixture was concentrated by evaporation under reduced pressure. The residue thus obtained was subjected to silica gel column chromatography, using toluene as the eluent, to give 1.85 g of the title compound as a pale brown oil.

Nuclear Magnetic Resonance Spectrum (CDCl$_3$) δ ppm: 1.05 (3H, triplet, J=7.0 Hz); 2.53 (2H, quartet, J=7.0 Hz); 3.73 (2H, singlet); 7.00–7.40 (4H, multiplet).

Mass spectrum (CI, m/z): 167 (M$^+$+1), 109.

PREPARATION 10

1-(2-Chlorophenyl)-2-propanone

Following a procedure similar to that described in Preparation 9, except that equivalent amounts of 2-chlorobenzaldehyde and nitroethane were used in place of the 2-fluorobenzaldehyde and nitropropane, the title compound was obtained as a brown oil in a yield of 27%.

Nuclear Magnetic Resonance Spectrum (CDCl$_3$) δ ppm: 2.20 (3H, singlet); 3.85 (2H, singlet); 7.15–7.45 (4H, multiplet).

Mass spectrum (CI, m/z): 169 (M$^+$+1), 125.

PREPARATION 11

1-(2-chlorophenyl)-2-butanone

Following a procedure similar to that described in Preparation 9, except that an equivalent amount of 2-chlorobenzaldehyde was used in place of the 2-fluorobenzaldehyde, the title compound was obtained as a pale yellow oil in a yield of 17%.

Mass spectrum (CI, m/z): 183 (M$^+$+1), 125.

PREPARATION 12

1-(2-Chlorophenyl)-2-heptanone

Following a procedure similar to that described in Preparation 9, except that equivalent amounts of 2-chlorobenzaldehyde and nitrohexane were used in place of the 2-fluorobenzaldehyde and nitropropane, the title compound was obtained as a pale yellow oil in a yield of 17%.

Nuclear Magnetic Resonance Spectrum (CDCl$_3$) δ ppm: 0.90 (3H, triplet, J=8.0 Hz); 1.20–1.40 (4H, multiplet); 1.50–1.70 (2H, multiplet); 2.50 (2H, triplet, J=10.0 Hz); 3.80 (2H, singlet); 7.20–7.60 (4H, multiplet).

Mass spectrum (CI, m/z): 225 (M$^+$+1), 125.

PREPARATION 13

Cyclobutyl 2-fluorobenzyl ketone 20 ml of anhydrous diethyl ether were added to 1.06 g (44 mmole) of metallic magnesium, and then a solution of 7.56 g (40 mmole) of 2-fluorobenzyl bromide in 10 ml of diethyl ether was slowly added dropwise to the resulting mixture, whilst stirring; the mixture was then stirred at room temperature for 1 hour. The resulting solution was slowly added dropwise to a solution of 4.74 g (40 mmole) of cyclobutanecarbonyl chloride in 30 ml of tetrahydrofuran, whilst cooling in a methanol-dry ice bath, over a period of 2 hours, and then the mixture was allowed to return to room temperature, whilst stirring, over a period of 2 hours. At the end of this time, 100 ml of water and 150 ml of diethyl ether were added to the reaction mixture, and the organic layer was separated, dried over anhydrous magnesium sulfate and concentrated by evaporation under reduced pressure. The residue thus obtained was subjected to silica gel column chromatography, using a 9:1 by volume mixture of toluene and hexane as the eluent, to give 2.97 g of the title compound as a pale yellow oil.

Nuclear Magnetic Resonance Spectrum (CDCl$_3$) δ ppm: 1.65–2.40 (6H, multiplet); 3.31–3.48 (1H, multiplet); 3.67 (2H, singlet); 7.00–7.30 (4H, multiplet).

Mass spectrum (CI, m/z): 193 (M$^+$+1), 137.

PREPARATION 14

5-Chloro-1-(2-chlorophenyl)-2-pentanone

Following a procedure similar to that described in Preparation 13, except that equivalent amounts of 2-chlorobenzyl bromide and 4-chlorobutyryl chloride were used in place of the 2-fluorobenzyl bromide and cyclobutanecarbonyl chloride, the title compound was obtained as a yellow oil in a yield of 79%.

Nuclear Magnetic Resonance Spectrum (CDCl$_3$) δ ppm: 1.96–2.15 (2H, multiplet); 2.69 (2H, triplet, J=7.7 Hz); 3.56 (2H, triplet, J=7.7 Hz); 3.86 (2H, singlet); 7.10–7.50 (4H, multiplet).

PREPARATION 15

1-(2-Chlorophenyl)-3,3,3-trifluoro-2-propanone 10 ml of anhydrous diethyl ether were added to 0.9 g (37.0 mmole) of metallic magnesium, and then a solution of 3.9 ml (30.8 mmole) of 2-chlorobenzyl chloride in 10 ml of diethyl ether was slowly added dropwise to the resulting mixture, with vigorous stirring, over a period of 30 minutes; the mixture was then stirred at room temperature for 1 hour. The resulting solution was slowly added dropwise to a solution of 4.3 ml (30.8 mmole) of trifluoroacetic anhydride in 40 ml of tetrahydrofuran, whilst cooling to about −70° C., and then the mixture was allowed to return to room temperature, whilst stirring, over a period of about 1 hour; after this, the mixture was left to stand overnight. At the end of this time, 200 ml of ethyl acetate were added to the resulting reaction mixture, and the organic layer was separated, washed with 1N aqueous hydrochloric acid and with a saturated aqueous solution of sodium chloride, in that order, dried over anhydrous sodium sulfate and concentrated by evaporation under reduced pressure. The residue thus obtained was subjected to silica gel column chromatography, using a 10:2 by volume mixture of toluene and ethyl acetate as the eluent, to give 5.7 g of the title compound as a yellow oil.

Nuclear Magnetic Resonance Spectrum (CDCl$_3$) δ ppm: 4.16 (2H, singlet); 7.10–7.50 (4H, multiplet).

Mass spectrum (CI, m/z): 223 (M$^+$+1), 125.

PREPARATION. 16

2-Chloro-α-trifluoroacetylbenzyl bromide 2.0 g (9.0 mmole) of 1-(2-chlorophenyl)-3,3,3-trifluoro-2-propanone were dissolved in 30 ml of carbon tetrachloride, and then 0.46 ml (9.0 mmole) of bromine was added to the solution, which was then stirred at room temperature for 10 hours. At the end of this time, sodium hydrogensulfite was added to the reaction mixture, and the mixture was stirred at room temperature for 15 minutes, after which insolubles were removed by filtration. The filtrate was concentrated by evaporation under reduced pressure, and the residue was subjected to silica gel column chromatography, using a 10:2 by volume mixture of toluene and ethyl acetate as the eluent, to give 0.87 g of the title compound as a yellow oil.

Nuclear Magnetic Resonance Spectrum (CDCl$_3$) δ ppm: 6.39 (1H, singlet); 7.30–7.70 (4H, multiplet).

Mass spectrum (CI, m/z): 302 (M$^+$+2), 300 (M$^+$), 221.

PREPARATION 17

2-Chloro-α-(4-chlorobutyryl)benzyl bromide

Following a procedure similar to that described in Preparation 16, except that an equivalent amount of 1-(2-chlorophenyl)-5-chloro-2-pentanone was used in place of the 1-(2-chlorophenyl)-3,3,3-trifluoro-2-propanone, the title compound was obtained as a yellow oil in a yield of 72%.

Nuclear Magnetic Resonance Spectrum (CDCl$_3$) δ ppm: 2.01–2.14 (2H, multiplet); 2.40–2.90 (2H, multiplet); 3.49–3.61 (2H, multiplet); 5.98 (1H, singlet); 7.20–7.60 (4H, multiplet).

Mass spectrum (CI, m/z): 311 (M$^+$+1), 231.

PREPARATION 18

2-Chloro-α-(5,6-dihydro-1,4,2-dioxazin-3-yl)benzyl bromide 4.0 g (19 mmole) of 3-(2-chlorobenzyl)-5,6-dihydro-1,4,2-dioxazine (prepared as described in Preparation 1) were dissolved in 40 ml of carbon tetrachloride, and then 4.1 g (23 mmole) of N-bromosuccinimide and 0.2 g of benzoyl peroxide were added to the solution, which was then stirred, whilst heating, for 8 hours. At the end of this time, 100 ml of ethyl acetate and 100 ml of hexane were added to the solution, and the mixture was stirred at room temperature for 30 minutes; insolubles were then removed by filtration. The filtrate was concentrated by evaporation under reduced pressure, to give 4.8 g of the title compound as a yellow oil.

Mass spectrum (CI, m/z): 292 (M$^+$+3), 290 (M$^+$+1), 212.

PREPARATION 19

2-Fluoro-α-(5,6-dihydro-1,4,2-dioxazin-3-yl)benzyl bromide

Following a procedure similar to that described in Preparation 18, except that an equivalent amount of 3-(2-fluorobenzyl)-5,6-dihydro-1,4,2-dioxazine (prepared as described in Preparation 2) was used in place of the 3-(2-chlorobenzyl)-5,6-dihydro-1,4,2-dioxazine, the title compound was obtained as a red oil in a yield of 98%.

Mass spectrum (CI, m/z): 276 (M$^+$+3), 194.

PREPARATION 20

2,6-Difluoro-α-(5,6-dihydro-1,4,2-dioxazin-3-yl)benzyl bromide

Following a procedure similar to that described in Preparation 18, except that an equivalent amount of 3-(2,6-difluorobenzyl)-5,6-dihydro-1,4,2-dioxazine (prepared as described in Preparation 3) was used in place of the 3-(2-chlorobenzyl)-5,6-dihydro-1,4,2-dioxazine, the title compound was obtained as a red oil in a yield of 57%.

Mass spectrum (CI, m/z): 294 (M$^+$+3), 214.

PREPARATION 21

2-Chloro-α-cyclopropylcarbonylbenzyl bromide

Following a procedure similar to that described in preparation 18, except that an equivalent amount of 2-chlorobenzyl cyclopropylketone (prepared as described in Preparation 4) was used in place of the 3-(2-chlorobenzyl)-5,6-dihydro-1,4,2-dioxazine, the title compound was obtained as a red oil in a yield of 83%.

Nuclear Magnetic Resonance Spectrum (CDCl$_3$) δ ppm: 0.80–1.20 (4H, multiplet); 2.04–2.16 (1H, multiplet); 6.18 (1H, singlet); 7.20–7.60 (4H, multiplet).

Mass spectrum (CI, m/z): 275 (M$^+$+3), 193.

PREPARATION 22

2-Chlorobenzyl 4-fluorophenyl ketone

Following a procedure similar to that described in Preparation 13, except that equivalent amounts of 2-chlorobenzyl bromide and 4-fluorobenzoyl chloride were used in place of the 2-fluorobenzyl bromide and cyclobutanecarbonyl chloride, the title compound was obtained as a colorless powder in a yield of 34%.

Nuclear Magnetic Resonance Spectrum (CDCl$_3$) δ ppm: 4.40 (2H, singlet); 7.10–7.45 (6H, multiplet); 8.04–8.10 (2H, multiplet).

Mass spectrum (CI, m/z): 249 (M$^+$+1), 213.

PREPARATION 23

2-Fluorobenzyl isopropyl ketone

Following a procedure similar to that described in Preparation 4, except that equivalent amounts of 2-fluorobenzyl chloride and isobutyronitrile were used in place of the 2-chlorobenzyl bromide and cyclopropyl cyanide, the title compound was obtained as a colorless oil in a yield of 25%.

Nuclear Magnetic Resonance Spectrum (CDCl$_3$) δ ppm: 1.15 (6H, doublet, J=7.5 Hz); 2.75 (1H, septet, J=7.5 Hz); 3.78 (2H, singlet); 6.97–7.30 (4H, multiplet).

Mass spectrum (CI, m/z): 181 (M$^+$+1), 109.

PREPARATION 24

2-Nitro-4,5,6,7-tetrahydrothieno[3,2-c]pyridine hydrochloride

24(a) 5-Acetyl-4,5,6,7-tetrahydrothieno[3,2-c]pyridine 35.1 g (200 mmole) of 4,5,6,7-tetrahydrothieno[3,2-c]pyridine hydrochloride and 38.57 g (200 mmole) of 28% w/v sodium methoxide in methanol were added to 200 ml of ethanol, and the resulting mixture was stirred at room temperature for 1 hour. The inorganic salt thus precipitated was filtered off, and the filtrate was concentrated to dryness by evaporation under reduced pressure. 50 ml of acetic anhydride were added all at once, whilst stirring, to the residue, and the resulting mixture was stirred at room temperature for 1 hour. The reaction mixture was then concentrated to dryness by evaporation under reduced pressure, and the residue thus obtained was subjected to silica gel column chromatography, using a 6:4 by volume mixture of toluene and ethyl acetate as the eluent, to give 29.32 g of the title compound as a yellow oil.

24(b) 5-Acetyl-2-nitro-4,5,6,7-tetrahydrothieno[3,2-c]pyridine 20 ml of an acetic anhydride solution containing 5.43 g (30 mmole) of 5-acetyl-4,5,6,7-tetrahydrothieno[3,2-c]pyridine [prepared as described in step (a) above] were added dropwise at 10° to 18° C. over a period of one hour to 30 ml of an acetic acid solution containing 4.2 g (60 mmole) of 90% fuming nitric acid, and the mixture was then stirred at a temperature not greater than 18° C. for 1 hour. The reaction mixture was then poured into ice-water and extracted with methylene chloride. The organic layer was separated, washed with a saturated aqueous solution of sodium hydrogencarbonate and with water, in that order, and dried over anhydrous magnesium sulfate. The solvent was then removed by distillation under reduced pressure, and the resulting residue was crystallized from a mixture of hexane and toluene, to give 4.46 g of the title compound as yellow crystals.

Nuclear Magnetic Resonance Spectrum (CDCl₃) δ ppm: 2.19 & 2.21 (together 3H, each singlet); 2.82–3.05 (2H, multiplet); 3.80 & 3.95 (together 2H, each triplet, J=5.7 Hz); 4.55 & 4.66 (together 2H, each singlet); 7.66 (1H, singlet ).

Mass spectrum (CI, m/z): 227 (M⁺ +1).

24(c) 2-Nitro-4,5,6,7-tetrahydrothieno[3,2-c]pyridine hydrochloride 2.38 g (10.53 mmole) of 5-acetyl-2-nitro-4,5,6,7-tetrahydrothieno[3,2-c]pyridine [prepared as described in step (b) above] were heated under reflux for 2 hours in 60 ml of 10% w/v aqueous hydrochloric acid. The reaction mixture was then concentrated to dryness by evaporation under reduced pressure, to give 2.19 g of the title compound as brown crystals.

Nuclear Magnetic Resonance Spectrum (CD₃OD) δ ppm: 3.22 (2H, triplet, J=6.2 Hz); 3.60 (2H, triplet, J=6.2 Hz); 4.31 (2H, singlet); 7.87 (1H, singlet).

Mass spectrum (CI, m/z): 185 (M⁺ +1).

PREPARATION 25

4,5,6,7-Tetrahydrofuro[3,2-c]pyridine 3.7 g (46 mmole) of a 37% aqueous formaldehyde solution were added dropwise at room temperature to 5.1 g (46 mmole) of 2-furylethylamine [the compound described, for example, in Brit., J. Pharmacol., 9, 376 (1954)], and the resulting mixture was stirred for about 15 minutes, after which it was extracted with diethyl ether. The organic extract was washed with water and dried over anhydrous sodium sulfate, and then the diethyl ether was removed by distillation under reduced pressure. 5 ml of dimethylformamide were added to the residue, and the resulting solution was added dropwise to 15 ml of dimethylformamide containing 3.6 g (100 mmole) of dry hydrogen chloride at room temperature. The resulting mixture was then stirred for 3 hours. At the end of this time, the greater part of the dimethylformamide was removed by distillation under reduced pressure, and then water and a 0.1N aqueous solution of sodium hydroxide were added to the residue so as to adjust its pH to a value of about 11; the mixture was then extracted with chloroform. The organic extract was washed with water and dried over anhydrous sodium sulfate. The chloroform was then removed by evaporation under reduced pressure, and the resulting residue was purified by silica gel column chromatography, using a 50:1 by volume mixture of chloroform and methanol as the eluent, to give the title compound as a brown oil in a yield of 27%.

Nuclear Magnetic Resonance Spectrum (CDCl₃) δ ppm: 3.10–3.20 (4H, multiplet); 3.70–3.80 (2H, multiplet); 6.20 (1H, singlet); 7.27 (1H, singlet).

Mass spectrum (CI, m/z): 124 (M⁺ +1).

PREPARATION 26

2-Fluorobenzyl 2-fluorocyclopropyl ketone

A procedure similar to that described in Preparation 13 was repeated, except that an equivalent amount of 2-fluorocyclopropylcarbonyl chloride was used in place of the cyclobutylcarbonyl chloride, to give the title compound as a colorless oil in a yield of 27%.

Nuclear Magnetic Resonance Spectrum (CDCl₃) δ ppm: 1.38–1.58 (2H, multiplet); 2.34–2.56 (1H, multiplet); 3.90 (2H, singlet); 4.54–4.61 & 4.86–4.93 (together 1H, each multiplet); 7.05–7.35 (4H, multiplet).

Mass spectrum (CI, m/z): 197 (M⁺ +1), 109.

PREPARATION 27

2-Fluoro-α-(2-fluorocyclopropylcarbonyl)benzyl bromide

A procedure similar to that described in Preparation 18 was repeated, except that an equivalent amount of 2-fluorobenzyl 2-fluorocyclopropyl ketone was used in place of the 3-(2-chlorobenzyl)-5,6-dihydro-1,4,2-dioxazine, to give the title compound as a colorless oil in a yield of 76%.

Nuclear Magnetic Resonance Spectrum (CDCl₃) δ ppm: 1.44–1.73 (2H, multiplet); 2.54–2.76 (1H, multiplet); 4.54–4.68 & 4.85–4.99 (together 1H, each multiplet); 5.93 (1H, singlet); 7.05–7.60 (4H, multiplet).

Mass spectrum (CI, m/z): 277 (M⁺ +2), 275 (M⁺), 195.

We claim:

1. A compound of formula (I):

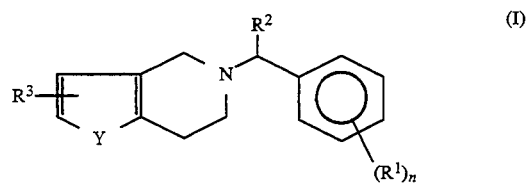

wherein:

R¹ represents a hydrogen atom, an alkyl group having from 1 to 4 carbon atoms, a halogen atom, a haloalkyl group having from 1 to 4 carbon atoms and at least one halogen atom, a hydroxy group, an alkoxy group having from 1 to 4 carbon atoms, a haloalkoxy group having from 1 to 4 carbon atoms and at least one halogen atom, an alkylthio group having from 1 to 4 carbon atoms, a haloalkylthio group having from 1 to 4 carbon atoms and at least one halogen atom, an amino group, an alkanoyl group having from 1 to 5 carbon atoms, a haloalkanoyl group having from 2 to 5 carbon atoms and at least one halogen atom, a carboxy group, an alkoxycarbonyl group having from 2 to 5 carbon atoms, a carbamoyl group, a cyano group, a nitro group, an alkanesulfonyl group having from 1 to 4 carbon atoms, a haloalkanesulfonyl group having from 1 to 4 carbon atoms and at least one halogen atom, or a sulfamoyl group;

R² represents a 5,6-dihydro-1,4,2-dioxazin-3-yl group; and

Y represents a group of formula —NH—, sulfur or oxygen;

R³ represents a hydrogen atom, a hydroxy group, an alkoxy group having from 1 to 4 carbon atoms, a substituted alkoxy group which has from 1 to 4 carbon atoms and which is substituted by at least one substituent selected from the group consisting of substituents C, defined below, an aralkyloxy group in which the aralkyl part is as defined below, an alkanoyloxy group having from 1 to 18 carbon atoms, an alkenoyloxy group having from 3 to 6 carbon atoms, a cycloalkylcarbonyloxy group having from 4 to 8 carbon atoms, an arylcarbonyloxy group in which the aryl part is as defined below, an alkoxycarbonyloxy group having from 2 to 5 carbon atoms, an aralkyloxycarbonyloxy group in which the aralkyl part is as defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula —NR$^a$R$^b$ wherein R$^a$ and R$^b$ are independently selected from the group consisting of hydrogen atoms, alkyl groups having from 1 to 4 carbon atoms and substituted alkyl groups which have from 1 to 4 carbon atoms and which are substituted by at least one substituent selected from the group consisting of substituents C, defined below, an aralkylamino group in which the aralkyl part is as defined below, an alkanoylamino group having from 1 to 18 carbon atoms, an alkenoylamino group having from 3 to 6 carbon atoms, a cycloalkylcarbonylamino group having from 4 to 8 carbon atoms, an arylcarbonylamino group in which the aryl part is as defined below, an alkoxycarbonylamino group having from 2 to 5 carbon atoms, an aralkyloxycarbonylamino group in which the aralkyl part is as defined below, a phthalidylamino group, a (5-methyl-2-oxo-1,3-dioxolen-4-yl)methylamino group, a (5-phenyl-2-oxo-1,3-dioxolen-4-yl)methylamino group or a nitro group; and n is an integer from 1 to 5, and, when n is an integer from 2 to 5, the groups represented by R$^1$ may be the same as or different from each other;

said substituents C are selected from the group consisting of alkoxy groups having from 1 to 4 carbon atoms, alkanoyloxy groups having from 1 to 6 carbon atoms and arylcarbonyloxy groups in which the aryl part is as defined below;

said aralkyl parts of said aralkyloxy, aralkyloxycarbonyloxy, aralkylamino and aralkyloxycarbonylamino groups are alkyl groups which have from 1 to 4 carbon atoms and which are substituted by at least one aryl group as defined below;

said aryl groups and said aryl parts of said arylcarbonyloxy groups and of said arylcarbonylamino groups have from 6 to 10 carbon atoms in a carbocyclic ring which is unsubstituted or is substituted by at least one substituent selected from the group consisting of substituents D, defined below; and said substituents D are selected from the group consisting of the groups and atoms defined above for R$^1$, other than said hydrogen atom;

or a tautomer thereof, or a pharmaceutically acceptable salt of said compound of formula (I) and of said tautomer.

2. The compound of claim 1, wherein said tautomer has the formula (Ia) or (Ib):

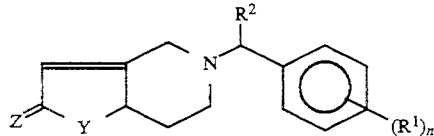

(Ia)

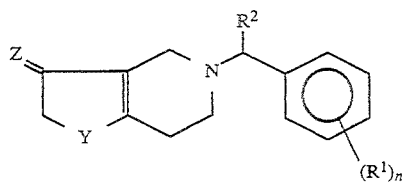

(Ib)

wherein R$^1$, R$^2$, Y and n are as defined above and Z represents group of formula =NH or an oxygen atom.

3. The compound of claim 1, wherein R$^1$ represents a hydrogen atom, an alkyl group having from 1 to 4 carbon atoms, a halogen atom, a fluoroalkyl group having from 1 to 4 carbon atoms and at least one fluorine atom, a hydroxy group, an alkoxy group having from 1 to 4 carbon atoms, a fluoroalkoxy group having from 1 to 4 carbon atoms and at least one fluorine atom, an alkylthio group having from 1 to 4 carbon atoms, a fluoroalkylthio group having from 1 to 4 carbon atoms and at least one fluorine atom, an amino group, an alkanoyl group having from 1 to 5 carbon atoms, a fluoroalkanoyl group having from 2 to 5 carbon atoms and at least one fluorine atom, an alkoxycarbonyl group having from 2 to 5 carbon atoms, a carbamoyl group, a cyano group, a nitro group, an alkanesulfonyl group having from 1 to 4 carbon atoms, a fluoroalkanesulfonyl group having from 1 to 4 carbon atoms and at least one fluorine atom, or a sulfamoyl group.

4. The compound of claim 1, wherein R$^3$ represents a hydrogen atom, a hydroxy group, an alkoxy group having from 1 to 4 carbon atoms, an alkoxymethoxy group in which the alkoxy part has from 1 to 4 carbon atoms, an alkanoyloxymethoxy group in which the alkanoyl part has from 1 to 5 carbon atoms, a benzyloxy group which is unsubstituted or is substituted by at least one substituent selected from the group consisting of substituents D, defined below, an alkanoyloxy group having from 1 to 18 carbon atoms, an alkenoyloxy group having 3 or 4 carbon atoms, a cycloalkylcarbonyloxy group having from 4 to 7 carbon atoms, a benzoyloxy group which is unsubstituted or is substituted by at least one substituent selected from the group consisting of substituents D, defined below, an alkoxycarbonyloxy group having from 2 to 5 carbon atoms, a benzyloxycarbonyloxy group which is unsubstituted or is substituted by at least one substituent selected from the group consisting of substituents D, defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula —NR$^a$R$^b$ wherein R$^a$ and R$^b$ are independently selected from the group consisting of hydrogen atoms, methyl and ethyl groups or R$^a$ represents a hydrogen atom and R$^b$ represents an alkanoyloxymethyl group in which the alkanoyl part has from 1 to 5 carbon atoms, a benzylamino group, an alkanoylamino group having from 1 to 18 carbon atoms, an alkenoylamino group having 3 or 4 carbon atoms, a cycloalkylcarbonylamino group having 6 or 7 carbon atoms, a benzoylamino group which is unsubstituted or is substituted by at least one substituent selected from the group consisting of substituents D, defined below, an alkoxycarbonylamino group having from 2 to 5 carbon atoms or a benzyloxycarbonylamino group which is unsubstituted or is substituted from the group consisting of substituents D, defined below; and said substituents D are selected from the group consisting of fluorine atoms, chlorine atoms, methyl groups and methoxy groups.

5. The compound of claim 1, wherein Y represents an oxygen atom.

6. The compound of claim 1, wherein:

$R^1$ represents a hydrogen atom, an alkyl group having from 1 to 4 carbon atoms, a halogen atom, a fluoroalkyl group having from 1 to 4 carbon atoms and at least one fluorine atom, a hydroxy group, an alkoxy group having from 1 to 4 carbon atoms, a fluoroalkoxy group having from 1 to 4 carbon atoms and at least one fluorine atom, an alkylthio group having from 1 to 4 carbon atoms, a fluoroalkylthio group having from 1 to 4 carbon atoms and at least one fluorine atom, an amino group, an alkanoyl group having from 1 to 5 carbon atoms, a fluoroalkanoyl group having from 2 to 5 carbon atoms and at least one fluorine atom, an alkoxycarbonyl group having from 2 to 5 carbon atoms, a carbamoyl group, a cyano group, a nitro group, an alkanesulfonyl group having from 1 to 4 carbon atoms, a fluoroalkanesulfonyl group having from 1 to 4 carbon atoms and at least one fluorine atom, or a sulfamoyl group;

$R^3$ represents a hydrogen atom, a hydroxy group, an alkoxy group having from 1 to 4 carbon atoms, an alkoxymethoxy group in which the alkoxy part has from 1 to 4 carbon atoms, an alkanoyloxymethoxy group in which the alkanoyl part has from 1 to 5 carbon atoms, a benzyloxy group which is unsubstituted or is substituted by at least one substituent selected from the group consisting of substituents D, defined below, an alkanoyloxy group having from 1 to 18 carbon atoms, an alkenoyloxy group having 3 or 4 carbon atoms, a cycloalkylcarbonyloxy group having from 4 to 7 carbon atoms, a benzoyloxy group which is unsubstituted or is substituted by at least one substituent selected from the group consisting of substituents D, defined below, an alkoxycarbonyloxy group having from 2 to 5 carbon atoms, a benzyloxycarbonyloxy group which is unsubstituted or is substituted by at least one substituent selected from the group consisting of substituents D, defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula —$NR^aR^b$ wherein $R^a$ and $R^b$ are independently selected from the group consisting of hydrogen atoms, methyl groups and ethyl groups or $R^a$ represents a hydrogen atom and $R^b$ represents an alkanoyloxymethyl group in which the alkanoyl part has from 1 to 5 carbon atoms, a benzylamino group, an alkanoylamino group having from 1 to 18 carbon atoms, an alkenoylamino group having 3 or 4 carbon atoms, a cycloalkylcarbonylamino group having 6 or 7 carbon atoms, a benzoylamino group which is unsubstituted or is substituted by at least one substituent selected from the group consisting of substituents D, defined below, an alkoxycarbonylamino group having from 2 to 5 carbon atoms or a benzyloxycarbonylamino group which is unsubstituted or is substituted by at least one substituent selected from the group consisting of substituents D, defined below;

Y represents an oxygen or sulfur atom;

said substituents D are selected from the group consisting of fluorine atoms, chlorine atoms, methyl groups and methoxy groups.

7. The compound of claim 6, wherein n is from 1 to 3.

8. The compound of claim 6, wherein n is 1.

9. The compound of claim 1, wherein $R^1$ represents a hydrogen atom, a methyl group, an ethyl group, a halogen atom, a methyl group substituted by at least one fluorine atom, a hydroxy group, a methoxy group, an ethoxy group, a methoxy group substituted by at least one fluorine atom, a methylthio group, a methylthio group substituted by at least one fluorine atom, a formyl group, an acetyl group, an acetyl group substituted by at least one fluorine atom, an alkoxycarbonyl group having from 2 to 4 carbon atoms, a carbamoyl group, a cyano group, a nitro group, a methanesulfonyl group, an ethanesulfonyl group, a methanesulfonyl group substituted by at least one fluorine atom, or a sulfamoyl group.

10. The compound of claim 1, wherein $R^3$ represents a hydrogen atom, a hydroxy group, a methoxy group, an ethoxy group, a t-butoxy group, a methoxymethoxy group, an alkanoyloxymethoxy group in which the alkanoyl part has from 1 to 5 carbon atoms, a benzyloxy group, an alkanoyloxy group having from 1 to 12 carbon atoms, an alkenoyloxy group having 3 or 4 carbon atoms, a cycloalkylcarbonyloxy group having from 4 to 7 carbon atoms, a benzoyloxy group, an alkoxycarbonyloxy group having from 2 to 5 carbon atoms, a benzyloxycarbonyloxy group, a phthalidyloxy group, a (5-methyl-2-oxo-1,3-dioxolen-4-yl)methoxy group, a (5-phenyl-2-oxo-1,3-dioxolen-4-yl)methoxy group, an amino group or a t-butoxycarbonylamino group.

11. The compound of claim 1, wherein:

$R^1$ represents a hydrogen atom, a methyl group, an ethyl group, a halogen atom, a methyl group substituted by at least one fluorine atom, a hydroxy group, a methoxy group, an ethoxy group, a methoxy group substituted by at least one fluorine atom, a methylthio group, a methylthio group substituted by at least one fluorine atom, a formyl group, an acetyl group, an acetyl group substituted by at least one fluorine atom, an alkoxycarbonyl group having from 2 to 4 carbon atoms, a carbamoyl group, a cyano group, a nitro group, a methanesulfonyl group, an ethanesulfonyl group, a methanesulfonyl group substituted by at least one fluorine atom, or a sulfamoyl group;

$R^3$ represents a hydrogen atom, a hydroxy group, a methoxy group, an ethoxy group, a t-butoxy group, a methoxymethoxy group, an alkanoyloxymethoxy group in which the alkanoyl part has from 1 to 5 carbon atoms, a benzyloxy group, an alkanoyloxy group having from 1 to 12 carbon atoms, an alkenoyloxy group having 3 or 4 carbon atoms, a cycloalkylcarbonyloxy group having from 4 to 7 carbon atoms, a benzoyloxy group, an alkoxycarbonyloxy group having from 2 to 5 carbon atoms, a benzyloxycarbonyloxy group, a phthalidyloxy group, a (5-methyl-2-oxo-1,3-dioxolen-4-yl)methoxy group, a (5-phenyl-2-oxo-1,3-dioxolen-4-yl)methoxy group, an amino group or a t-butoxycarbonylamino group; and Y represents an oxygen.

12. The compound of claim 11, wherein n is from 1 to 3.

13. The compound of claim 11, wherein n is 1.

14. The compound of claim 1, wherein $R^1$ represents a halogen atom, a trifluoromethyl group, a hydroxy group, a difluoromethoxy group, a trifluoromethoxy group, a difluoromethylthio group, a trifluoromethylthio group, a formyl group, an acetyl group, a trifluoroacetyl group, a cyano group or a nitro group.

15. The compound of claim 1, wherein $R^3$ represents a hydrogen atom, a hydroxy group, a pivaloyloxymethoxy group, an alkanoyloxy group having from 2 to 10 carbon atoms, an alkoxycarbonyloxy group having from 2 to 5 carbon atoms or a (5-methyl-2-oxo-1,3-dioxolen-4-yl)methoxy group.

16. The compound of claim 1, wherein Y represents a sulfur atom.

17. The compound of claim 1, wherein:
$R^1$ represents a halogen atom, a trifluoromethyl group, a hydroxy group, a difluoromethoxy group, a trifluoromethoxy group, a difluoromethylthio group, a trifluoromethylthio group, a formyl group, an acetyl group, a trifluoroacetyl group, a cyano group or a nitro group;
$R^3$ represents a hydrogen atom, a hydroxy group, a pivaloyloxymethoxy group, an alkanoyloxy group having from 2 to 10 carbon atoms, an alkoxycarbonyloxy group having from 2 to 5 carbon atoms or a (5-methyl-2-oxo-1,3-dioxolen-4-yl)methoxy group; and
Y represents a sulfur atom.

18. The compound of claim 17, wherein n is from 1 to 3.

19. The compound of claim 17, wherein n is 1.

20. The compound of claim 1, wherein $R^1$ represents a fluorine or chlorine atom.

21. The compound of claim 1, wherein $R^3$ represents a hydrogen atom, a hydroxy group, a pivaloyloxymethoxy group, an alkanoyloxy group having from 2 to 6 carbon atoms or an alkoxycarbonyloxy group having from 2 to 5 carbon atoms.

22. The compound of claim 1, wherein:
$R^1$ represents a fluorine or chlorine atom;
$R^3$ represents a hydrogen atom, a hydroxy group, a pivaloyloxymethoxy group, an alkanoyloxy group having from 2 to 6 carbon atoms or an alkoxycarbonyloxy group having from 2 to 5 carbon atoms.

23. The compound of claim 22, wherein n is from 1 to 3.

24. The compound of claim 22, wherein n is 1.

25. The compound of claim 1 wherein
Y represents sulfur.

26. The compound of claim 1 wherein
Y represents a group of formula —NH—.

27. The compound of claim 1 selected from the group consisting of
5-[2-chloro-α-(5,6-dihydro-1,4,2-dioxazin-3-yl)-benzyl]-4,5,6,7-tetrahydrothieno[3,2-c]pyridine;
5-[2-fluoro-α-(5,6-dihydro-1,4,2-dioxazin-3-yl)-benzyl]-4,5,6,7-tetrahydrothieno[3,2-c]pyridine; and
5-[2,6-difluoro-α-(5,6-dihydro-1,4,2-dioxazin-3-yl)-benzyl]-4,5,6,7-tetrahydrothieno[3,2-c]pyridine
or a pharmaceutically acceptable salt thereof.

28. The compound of claim 27 which is 5-[2-fluoro-α(5,6-dihydro-1,4,2-dioxazin-3-yl)-benzyl]-4,5,6,7-tetrahydrothieno[3,2-c]pyridine or a pharmaceutically acceptable salt thereof.

29. A pharmaceutical composition for the treatment of thrombosis or embolisms, comprising an effective amount of a blood platelet aggregation inhibitor in admixture with a pharmaceutically acceptable carrier or diluent, wherein said inhibitor is at least one compound of formula (I), or a tautomer or pharmaceutically acceptable salt thereof, as claimed in claim 1.

30. The composition of claim 29, wherein:
$R^1$ represents a hydrogen atom, an alkyl group having from 1 to 4 carbon atoms, a halogen atom, a fluoroalkyl group having from 1 to 4 carbon atoms and at least one fluorine atom, a hydroxy group, an alkoxy group having from 1 to 4 carbon atoms, a fluoroalkoxy group having from 1 to 4 carbon atoms and at least one fluorine atom, an alkylthio group having from 1 to 4 carbon atoms, a fluoroalkylthio group having from 1 to 4 carbon atoms and at least one fluorine atom, an amino group, an alkanoyl group having from 1 to 5 carbon atoms, a fluoroalkanoyl group having from 2 to 5 carbon atoms and at least one fluorine atom, an alkoxycarbonyl group having from 2 to 5 carbon atoms, a carbamoyl group, a cyano group, a nitro group, an alkanesulfonyl group having from 1 to 4 carbon atoms, a fluoroalkanesulfonyl group having from 1 to 4 carbon atoms and at least one fluorine atom, or a sulfamoyl group;
$R^3$ represents a hydrogen atom, a hydroxy group, an alkoxy group having from 1 to 4 carbon atoms, an alkoxymethoxy group in which the alkoxy part has from 1 to 4 carbon atoms, an alkanoyloxymethoxy group in which the alkanoyl part has from 1 to 5 carbon atoms, a benzyloxy group which is unsubstituted or is substituted by at least one substituent selected from the group consisting of substituents D, defined below, an alkanoyloxy group having from 1 to 18 carbon atoms, an alkenoyloxy group having 3 or 4 carbon atoms, a cycloalkylcarbonyloxy group having from 4 to 7 carbon atoms, a benzoyloxy group which is unsubstituted or is substituted by at least one substituent selected from the group consisting of substituents D, defined below, an alkoxycarbonyloxy group having from 2 to 5 carbon atoms, a benzyloxycarbonyloxy group which is unsubstituted or is substituted by at least one substituent selected from the group consisting of substituents D, defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula —$NR^aR^b$ wherein $R^a$ and $R^b$ are independently selected from the group consisting of hydrogen atoms, methyl groups and ethyl groups or $R^a$ represents a hydrogen atom and $R^b$ represents an alkanoyloxymethyl group in which the alkanoyl part has from 1 to 5 carbon atoms,
a benzylamino group, an alkanoylamino group having from 1 to 18 carbon atoms, an alkenoylamino group having 3 or 4 carbon atoms, a cycloalkylcarbonylamino group having 6 or 7 carbon atoms, a benzoylamino group which is unsubstituted or is substituted by at least one substituent selected from the group consisting of substituents D, defined below, an alkoxycarbonylamino group having from 2 to 5 carbon atoms or a benzyloxycarbonylamino group which is unsubstituted or is substituted by at least one substituent selected from the group consisting of substituents D, defined below;

Y represents an oxygen or sulfur atom; and said substituents D are selected from the group consisting of fluorine atoms, chlorine atoms, methyl groups and methoxy groups.

31. The composition of claim 29 wherein:

$R^1$ represents a hydrogen atom, a methyl group, an ethyl group, a halogen atom, a methyl group substituted by at least one fluorine atom, a hydroxy group, a methoxy group, an ethoxy group, a methoxy group substituted by at least one fluorine atom, a methylthio group, a methylthio group substituted by at least one fluorine atom, a formyl group, an acetyl group, an acetyl group substituted by at least one fluorine atom, an alkoxycarbonyl group having from 2 to 4 carbon atoms, a carbamoyl group, a cyano group, a nitro group, a methanesulfonyl group, an ethanesulfonyl group, a methanesulfonyl group substituted by at least one fluorine atom, or a sulfamoyl group;

$R^3$ represents a hydrogen atom, a hydroxy group, a methoxy group, an ethoxy group, a t-butoxy group, a methoxymethoxy group, an alkanoyloxymethoxy group in which the alkanoyl part has from 1 to 5 carbon atoms, a benzyloxy group, an alkanoyloxy group having from 1 to 12 carbon atoms, an alkenoyloxy group having 3 or 4 carbon atoms, a cycloalkylcarbonyloxy group having from 4 to 7 carbon atoms, a benzoyloxy group, an alkoxycarbonyloxy group having from 2 to 5 carbon atoms, a benzyloxycarbonyloxy group, a phthalidyloxy group, a (5-methyl-2-oxo-1,3-dioxolen-4-yl)methoxy group, a (5-phenyl-2-oxo-1,3-dioxolen-4-yl)methoxy group, an amino group or a t-butoxycarbonylamino group; and Y represents an oxygen.

32. The composition of claim 29, wherein:

$R^1$ represents a halogen atom, a trifluoromethyl group, a hydroxy group, a difluoromethoxy group, a trifluoromethoxy group, a difluoromethylthio group, a trifluoromethylthio group, a formyl group, an acetyl group, a trifluoroacetyl group, a cyano group or a nitro group;

$R^3$ represents a hydrogen atom, a hydroxy group, a pivaloyloxymethoxy group, an alkanoyloxy group having from 2 to 10 carbon atoms, an alkoxycarbonyloxy group having from 2 to 5 carbon atoms or a (5-methyl-2-oxo-1,3-dioxolen-4-yl)methoxy group.

33. The composition of claim 29, wherein:

$R^1$ represents a fluorine or chlorine atom;

$R^3$ represents a hydrogen atom, a hydroxy group, a pivaloyloxymethoxy group, an alkanoyloxy group having from 2 to 6 carbon atoms or an alkoxycarbonyloxy group having from 2 to 5 carbon atoms.

34. The composition of claim 29 wherein said blood platelet aggregation inhibitor is selected from the group consisting of 5-[2-chloro-α-(5,6-dihydro-1,4,2-dioxazin-3-yl)-benzyl]-4,5,6,7-tetrahyrothieno[3,2-c]pyridine;

5-[2-fluoro-α-(5,6-dihydro-1,4,2-dioxazin-3-yl)-benzyl]-4,5,6,7-tetrahydrothieno[3,2-c]pyridine; and 5-[2,6-difluoro-α-(5,6-dihydro-1,4,2-dioxazin-3-yl)-benzyl]-4,5,6,7-tetrahydrothieno[3,2-c]pyridine or a pharmaceutically acceptable salt thereof.

35. A method for the treatment of thrombosis or embolisms, comprising administering to a mammal an effective amount of a blood platelet aggregation inhibitor, wherein said inhibitor is at least one compound of formula (I), or a tautomer or pharmaceutically acceptable salt thereof, as claimed in claim 1.

36. The method of claim 35, wherein:

$R^1$ represents a hydrogen atom, an alkyl group having from 1 to 4 carbon atoms, a halogen atom, a fluoroalkyl group having from 1 to 4 carbon atoms and at least one fluorine atom, a hydroxy group, an alkoxy group having from 1 to 4 carbon atoms, a fluoroalkoxy group having from 1 to 4 carbon atoms and at least one fluorine atom, an alkylthio group having from 1 to 4 carbon atoms, a fluoroalkylthio group having from 1 to 4 carbon atoms and at least one fluorine atom, an amino group, an alkanoyl group having from 1 to 5 carbon atoms, a fluoroalkanoyl group having from 2 to 5 carbon atoms and at least one fluorine atom, an alkoxycarbonyl group having from 2 to 5 carbon atoms, a carbamoyl group, a cyano group, a nitro group, an alkanesulfonyl group having from 1 to 4 carbon atoms, a fluoroalkanesulfonyl group having from 1 to 4 carbon atoms and at least one fluorine atom, or a sulfamoyl group;

$R^3$ represents a hydrogen atom, a hydroxy group, an alkoxy group having from 1 to 4 carbon atoms, an alkoxymethoxy group in which the alkoxy part has from 1 to 4 carbon atoms, an alkanoyloxymethoxy group in which the alkanoyl part has from 1 to 5 carbon atoms, a benzyloxy group which is unsubstituted or is substituted by at least one substituent selected from the group consisting of substituents D, defined below, an alkanoyloxy group having from 1 to 18 carbon atoms, an alkenoyloxy group having 3 or 4 carbon atoms, a cycloalkylcarbonyloxy group having from 4 to 7 carbon atoms, a benzoyloxy group which is unsubstituted or is substituted by at least one substituent selected from the group consisting of substituents D, defined below, an alkoxycarbonyloxy group having from 2 to 5 carbon atoms, a benzyloxycarbonyloxy group which is unsubstituted or is substituted by at least one substituent selected from the group consisting of substituents D, defined below, a phthalidyloxy group, a (5-methyl-2-oxo-1,3-dioxolen-4-yl)methoxy group, a (5-phenyl-2-oxo-1,3-dioxolen-4-yl)methoxy group, a group of formula —NR$^a$R$^b$ wherein R$^a$ and R$^b$ are independently selected from the group consisting of hydrogen atoms, methyl groups and ethyl groups or R$^a$ represents a hydrogen atom and R$^b$ represents an alkanoyloxymethyl group in which the alkanoyl part has from 1 to 5 carbon atoms, a benzylamino group, an alkanoylamino group having from 1 to 18 carbon atoms, an alkenoylamino group having 3 or 4 carbon atoms, a cycloalkylcarbonylamino group having 6 or 7 carbon atoms, a benzoylamino group which is unsubstituted or is substituted by at least one substituent selected from the group consisting of substituents D, defined below, an alkoxycarbonylamino group having from 2 to 5 carbon atoms or a benzyloxycarbonylamino group which is unsubstituted or is substituted by at least one substituent selected from the group consisting of substituents D, defined below;

Y represents an oxygen; and said substituents D are selected from the group consisting of fluorine atoms, chlorine atoms, methyl group and methoxy groups.

37. The method of claim 35, wherein:

$R^1$ represents a hydrogen atom, a methyl group, an ethyl group, a halogen atom, a methyl group substituted by at least one fluorine atom, a hydroxy group, a methoxy group, an ethoxy group, a methoxy group substituted by at least one fluorine atom, a methylthio group, a methylthio group substituted by at least one fluorine atom, a formyl group, an acetyl group, an acetyl group substituted by at least one fluorine atom, an alkoxycarbonyl group having from 2 to 4 carbon atoms, a carbamoyl group, a cyano group, a nitro group, a methanesulfonyl group, an ethanesulfonyl group, a methanesulfonyl group substituted by at least one fluorine atom, or a sulfamoyl group;

$R^3$ represents a hydrogen atom, a hydroxy group, a methoxy group, an ethoxy group, a t-butoxy group, a methoxymethoxy group, an alkanoyloxymethoxy group in which the alkanoyl part has from 1 to 5 carbon atoms, a benzyloxy group, an alkanoyloxy group having from 1 to 12 carbon atoms, an alkenoyloxy group having 3 or 4 carbon atoms, a cycloalkylcarbonyloxy group having from 4 to 7 carbon atoms, a benzoyloxy group, an alkoxycarbonyloxy group having from 2 to 5 carbon atoms, a benzyloxycarbonyloxy group, a phthalidyloxy group, a (5-methyl-2-oxo-1,3-dioxolen-4-yl)methoxy group, a (5-phenyl-2-oxo-1,3-dioxolen-4-yl)methoxy group, an amino group or a t-butoxycarbonylamino group; and Y represents an oxygen.

38. The method of claim 35, wherein:

$R^1$ represents a halogen atom, a trifluoromethyl group, a hydroxy group, a difluoromethoxy group, a trifluoromethoxy group, a difluoromethylthio group, a trifluoromethylthio group, a formyl group, an acetyl group, a trifluoroacetyl group, a cyano group or a nitro group;

$R^3$ represents a hydrogen atom, a hydroxy group, a pivaloyloxymethoxy group, an alkanoyloxy group having from 2 to 10 carbon atoms, an alkoxycarbonyloxy group having from 2 to 5 carbon atoms or a (5-methyl-2-oxo-1,3-dioxolen-4-yl)methoxy group.

39. The method of claim 35, wherein:

$R^1$ represents a fluorine or chlorine atom;

$R^3$ represents a hydrogen atom, a hydroxy group, a pivaloyloxymethoxy group, an alkanoyloxy group having from 2 to 6 carbon atoms or an alkoxycarbonyloxy group having from 2 to 5 carbon atoms.

40. The method of claim 35 wherein the inhibitor is selected from the group consisting of:

5-[2-chloro-α-(5,6-dihydro-1,4,2-dioxazin-3-yl)-benzyl]-4,5,6,7-tetrahyrothieno[3,2-c]pyridine;

5-[2-fluoro-α-(5,6-dihydro-1,4,2-dioxazin-3-yl)-benzyl]-4,5,6,7-tetrahydrothieno[3,2-c]pyridine; and 5-[2,6-difluoro-α-(5,6-dihydro-1,4,2-dioxazin-3-yl)-benzyl]-4,5,6,7-tetrahydrothieno[3,2-c]pyridine or a pharmaceutically acceptable salt thereof.

* * * * *

UNITED STATES PATENT AND TRADEMARK OFFICE
CERTIFICATE OF CORRECTION

PATENT NO. : 5,436,242
DATED : July 25, 1995
INVENTOR(S) : KOIKE et al

It is certified that error appears in the above-indentified patent and that said Letters Patent is hereby corrected as shown below:

Column 36, line 56: Before "Conversion" delete "(b 3)" and insert --(3)--.

Column 73, line 25: Delete "hydrogen atom, a hydroxy group, a".

Column 73, lines 26-28: Delete in entirety.

Column 73, line 29: delete "or".

Signed and Sealed this

Thirteenth Day of August, 1996

Attest:

BRUCE LEHMAN

Attesting Officer    Commissioner of Patents and Trademarks